US012559795B2

(12) United States Patent
Teo et al.

(10) Patent No.: US 12,559,795 B2
(45) Date of Patent: Feb. 24, 2026

(54) COMPOSITIONS, METHODS, KITS, CARTRIDGES, AND SYSTEMS FOR SEQUENCING REAGENTS

(71) Applicant: ILLUMINA, INC., San Diego, CA (US)

(72) Inventors: Yin Nah Teo, Singapore (SG); Karen Goh, Singapore (SG); Dorry Poa, Singapore (SG); Oliver Miller, Linton (GB); Sergio Peisajovich, San Diego, CA (US); Trina Osothprarop, San Diego, CA (US); Youna Ro, San Diego, CA (US); Sébastien Ricoult, Sawston (GB); Dale Weekes, Haverhill (GB)

(73) Assignee: Illumina, Inc., San Diego, CA (US)

( * ) Notice: Subject to any disclaimer, the term of this patent is extended or adjusted under 35 U.S.C. 154(b) by 11 days.

(21) Appl. No.: 17/808,161

(22) Filed: Jun. 22, 2022

(65) Prior Publication Data

US 2022/0411864 A1 Dec. 29, 2022

Related U.S. Application Data

(60) Provisional application No. 63/213,995, filed on Jun. 23, 2021.

(51) Int. Cl.
C12Q 1/6869 (2018.01)

(52) U.S. Cl.
CPC .................................. C12Q 1/6869 (2013.01)

(58) Field of Classification Search
CPC ................ C12Q 1/6869; C12Q 1/6806; C12Q 2525/186; C12Q 2565/629
See application file for complete search history.

(56) References Cited

U.S. PATENT DOCUMENTS

| | | | | |
|---|---|---|---|---|
| 5,861,251 | A * | 1/1999 | Park ......................... | C07H 3/02 |
| | | | | 435/6.12 |
| 6,153,412 | A | 11/2000 | Park et al. | |
| 7,541,444 | B2 | 6/2009 | Milton et al. | |
| 7,754,429 | B2 | 7/2010 | Rigatti et al. | |
| 8,178,360 | B2 | 5/2012 | Barnes et al. | |
| 8,426,134 | B2 * | 4/2013 | Piepenburg .......... | C12N 9/1252 |
| | | | | 435/6.12 |
| 8,431,348 | B2 | 4/2013 | Rigatti et al. | |
| 8,895,249 | B2 | 11/2014 | Shen et al. | |
| 9,012,184 | B2 | 4/2015 | Rigatti et al. | |
| 9,328,378 | B2 | 5/2016 | Earnshaw et al. | |
| 9,453,258 | B2 | 9/2016 | Kain et al. | |
| 9,593,373 | B2 | 3/2017 | Liu et al. | |
| 9,868,944 | B2 | 1/2018 | Martinez et al. | |
| 9,902,994 | B2 | 2/2018 | Gormley et al. | |
| 10,167,505 | B2 * | 1/2019 | Shen .................... | C12Q 1/6874 |
| 10,563,254 | B2 * | 2/2020 | Lee ...................... | C12Q 1/6865 |
| 2005/0069898 | A1 | 3/2005 | Moon et al. | |
| 2009/0291427 | A1 * | 11/2009 | Muller-Cohn ........... | A01N 1/02 |
| | | | | 435/5 |

| | | | | |
|---|---|---|---|---|
| 2010/0159531 | A1 * | 6/2010 | Gordon .................. | G16B 25/00 |
| | | | | 435/91.5 |
| 2013/0338042 | A1 | 12/2013 | Shen et al. | |
| 2019/0226018 | A1 * | 7/2019 | Andruzzi ............. | C12Q 1/6876 |
| 2021/0069254 | A1 * | 3/2021 | Görgens ................. | A61K 47/02 |

FOREIGN PATENT DOCUMENTS

| | | | | |
|---|---|---|---|---|
| WO | | 2005103277 A1 | 11/2005 | |
| WO | | 2006064199 A1 | 6/2006 | |
| WO | | WO-2012106081 A2 * | 8/2012 | ......... C12N 15/1003 |
| WO | | WO-2016165831 A1 * | 10/2016 | ......... A61K 31/7105 |

OTHER PUBLICATIONS

Andre et al. (Int J Cosmet Sci . Aug. 2017;39(4):355-360. doi: 10.1111/ics.12386. Epub Feb. 17, 2017. (Year: 2017).*
Milano et al. (Radiat Res. Aug. 1999; 152(2): 196-201.) (Year: 1999).*
Roman et al., "Relationship of the Physical and Enzymatic Properties of *Escherichia coli* RecA Protein to Its Strand Exchange Activity", Biochemistry, vol. 25, pp. 7375-7385. 1986.
Piepenburg et al., "DNA Detection Using Recombination Proteins", PLOS Biology, vol. 4, issue 7, pp. 1115-1121. Jul. 2006.
Telikepalli et al., "Characterization of the Physical Stability of a Lyophilized IgG1 mAb after Accelerated Shipping-Like Stress", Pharmaceutical Biotechnology, Journal of Pharmaceutical Sciences, vol. 104, pp. 495-507. Dec. 17, 2014.
Kim et al., "RecA requires two molecules of Mg2+ ions for its optimal strand exchange activity in vitro", Nucleic Acids Research, vol. 46, No. 5, pp. 2548-2559. Jan. 30, 2018.
Challener, "For Lyophilization, Excipients Really Do Matter", BioPharm International, vol. 30, issue 1, pp. 32-35. Jan. 1, 2017.
Illumina, "Quality Scores for Next-Generation Sequencing Assessing sequencing accuracy using Phred quality scoring", 2 pages. Oct. 31, 2011.

(Continued)

*Primary Examiner* — Fereydoun G Sajjadi
*Assistant Examiner* — Joel D Levin
(74) *Attorney, Agent, or Firm* — Heslin Rothenberg Farley & Mesiti P.C.

(57) ABSTRACT

The present disclosure relates to a composition including one or more modified nucleotide, wherein the modified nucleotide comprises a purine or pyrimidine base and a sugar moiety having a 3'-hydroxy blocking group, and a radical scavenger, wherein the composition is lyophilised. The present disclosure further relates to a composition including one or more functional protein; one or more functional protein activator; and one or more non-reducing sugar, wherein the composition is lyophilised. Also disclosed are methods of rehydration of one or more compositions described herein and kits including one or more compositions described herein. Further disclosed are cartridges including a flow cell comprising one or more reagent reservoirs, where the one or more reagent reservoirs include one or more compositions described herein.

19 Claims, 50 Drawing Sheets

(56) References Cited

OTHER PUBLICATIONS

Patel et al., "Research Note: In Pursuit of a Ready-To-Use, Shelf-Stable qPCR Mix", OPS Diagnostics, LLC., 5 pages. date unknown.
McCartney, "Mechanical characterisation of freeze-dried biopharmaceuticals", A dissertation submitted to Imperial College London for the degree of Doctor of Philosophy Department of Chemical Engineering Imperial College London, 346 pages. Apr. 2014.

* cited by examiner

FIG. 6

Catechin

PCA

2-HEG

Gallic acid

FIG. 10A $R^{\cdot} + ArOH \rightarrow RH + ArO^{\cdot}$

FIG. 10B

Intensity Scale

Lane: 1 2 3 4 5 6 7 8

Lane: 1  2  3  4  5  6  7  8

200mM trehalose
120mM mannitol ⟹ Residual moisture: 0.23%

300mM trehalose
120mM mannitol ⟹ Residual moisture: 0.17%

COMPOSITIONS, METHODS, KITS, CARTRIDGES, AND SYSTEMS FOR SEQUENCING REAGENTS

CROSS-REFERENCE TO RELATED APPLICATIONS

This application claims benefit of priority from U.S. Provisional Patent Application No. 63/213,995, filed Jun. 23, 2021, the entire contents of which is incorporated herein by reference in its entirety.

FIELD

The present disclosure relates generally to compositions, methods, kits, and systems for sequencing reagents.

BACKGROUND

Many current sequencing platforms use "sequencing by synthesis" ("SBS") technology and fluorescence based methods for detection. Alternative sequencing methods and improved sample preparation processes that allow for more cost effective, rapid, and convenient sequencing and nucleic acid detection are desirable as complements to SBS.

Current protocols for SBS technology routinely employ a sample preparation process that converts DNA or RNA into a library of fragmented, sequenceable templates. Sample preparation methods often involve multiple steps, material transfers, and expensive instruments to effect fragmentation, and, therefore, are often difficult, tedious, expensive, and inefficient.

Libraries including polynucleotides are generally prepared in any suitable manner to attach oligonucleotide adapters to target polynucleotides. Sequencing may result in determination of the sequence of the whole, or a part of the target polynucleotides. The number of steps involved to transform nucleic acids into adapter-modified templates in solution ready for cluster formation and sequencing can be reduced, or in some instances even minimized, by the use of transposase mediated fragmentation and tagging. This process, referred to as "tagmentation," involves the modification of nucleic acids by a transposome complex comprising transposase enzyme complexed with adapters comprising transposon end sequence, as described in, for example, WO 2016/130704. Methods for immobilizing and amplifying prior to sequencing are described in, for instance, U.S. Pat. No. 8,053,192, WO 2016/130704, U.S. Pat. Nos. 8,895,249, and 9,309,502. A library of templates may be used to prepare clustered arrays of nucleic acid colonies, as described in U.S. Pat. Publ. No. 2005/0100900, U.S. Pat. No. 7,115,400, WO 00/18957, and WO 98/44151, by solid-phase amplification and more particularly solid phase isothermal amplification.

Sequencing can be carried out using any suitable sequencing technique, and methods for determining the sequence of immobilized and amplified adapter-target-adapter molecules, including strand re-synthesis, are known in the art and are described in, for instance, U.S. Pat. No. 8,053,192, WO2016/130704, U.S. Pat. Nos. 8,895,249, and 9,309,502. SBS techniques generally involve the enzymatic extension of a nascent nucleic acid strand through the iterative addition of nucleotides against a template strand. In traditional methods of SBS, a single nucleotide monomer may be provided to a target nucleotide in the presence of a polymerase in each delivery. Exemplary SBS systems and methods are described in U.S. Pat. Publ. Nos. 2007/0166705, 2006/

0188901, 2006/0240439, 2006/0281109, 2012/0270305, and 2013/0260372, U.S. Pat. No. 7,057,026, WO 05/065814, U.S. Pat. Publ. No. 2005/0100900, WO 06/064199, and WO 07/010,251, U.S. Pat. Publ. No. 2013/0079232.

The stability of the reagents involved with sample preparation including, for example, PCR, varies depending on a variety of factors. Historically, reagents have been wet thereby requiring freezing for ship and storage. Moving to dry reagents allows for ambient transport and storage, but dry reagents are more sensitive than wet reagents to environmental conditions. If reagents are exposed on manufacture, transport, storage, or during library preparation, quality and efficiency of the resulting library is affected. Likewise, pH of reagents like SBS buffers varies during sequencing and there is a need for improved stabilization of these buffers to increase SBS performance. Reagents involved with sample preparation may be highly sensitive to changes in humidity, light, and moisture and, as a result, are notoriously difficult to keep stable.

Moreover, lyophilised microspheres which may be used in sample preparation often degrade upon exposure to mechanical stress during transport and storage and may unfavorably shed their outer covering. The resulting powder may be problematic in clogging membranes used in sample preparation and might result in variations in the desired end concentration after rehydration has been achieved. Static charge is also a risk for dispensing and dry compounding microspheres.

Therefore, there is a need for improved sample preparation compositions and processes. In particular, there is a need for sequencing reagents with improved stability and associated compositions, methods, systems, kits, and cartridges that demonstrate improved efficiency of workflow and tagmented library production and, in turn, increased read enrichment for the resulting libraries and simplified workflows.

The present disclosure is directed to overcoming these and other deficiencies in the art.

SUMMARY

A first aspect relates to a composition. The composition includes one or more modified nucleotide, wherein the modified nucleotide comprises a purine or pyrimidine base and a sugar moiety having a 3'-hydroxy blocking group, and a radical scavenger, wherein the composition is lyophilised.

In one implementation, the radical scavenger is a phenolic antioxidant. In one implementation, the radical scavenger comprises gallic acid (GA), hydroxyethyl gallate (HEG), protocatechuic acid (PCA), catechin, or a combination thereof.

In one implementation, the composition further includes one or more non-reducing sugar. In one implementation, the one or more non-reducing sugar is trehalose, sucrose, inositol, maltodextrin, dextran, mannitol, raffinose, cyclodextrin, melezitose, sorbitol, or a combination thereof. In one implementation, the composition includes at least about 5 wt. % non-reducing sugar. In one implementation, the composition includes about 5 wt % or less non-reducing sugar.

In one implementation, the composition further includes a polymerase. In another implementation, the composition further includes a functional protein activator. In one implementation, the functional protein activator is magnesium, a magnesium salt or other magnesium derivative, or a combination thereof.

In one implementation, the 3'-hydroxy blocking group is a reversible blocking group. In one implementation, the modified nucleotide is linked to a detectable label. In one implementation, the detectable label comprises a fluorophore. In one implementation, the modified nucleotide is linked to a detectable label via a cleavable linker.

In one implementation, the composition is a microsphere, a cake, or a combination thereof. In one implementation, the composition has a cross-section of between about 0.1 mm and about 25 mm. In one implementation, wherein, when the composition is a microsphere, the microsphere is spherical, elliptical, or toroidal.

In one implementation, the composition comprises less than about 1 wt. % glycerol. In one implementation, the composition comprises about 5 wt. % or less of a crowding agent. In one implementation, the crowding agent comprises polyethylene glycol (PEG), polyvinyl pyrrolidone, dextran, maltodextrin, ficoll, polyacrylamide, or any combination thereof. In one implementation, the composition has a moisture content below about 10 wt. %.

A second aspect relates to a method of rehydration. The method includes providing a composition including one or more modified nucleotide, wherein the modified nucleotide comprises a purine or pyrimidine base and a sugar moiety having a 3'-hydroxy blocking group, and a radical scavenger, wherein the composition is lyophilised; and mixing said composition with a rehydration solution under conditions effective to rehydrate the composition.

In one implementation, the rehydration solution is water, ethanolamine, or a combination thereof.

In one implementation, the method further includes using the rehydrated composition in a sequencing by synthesis process. In another implementation, the method further includes exposing the rehydrated composition to a sequencing primer, wherein incorporation of the one or more modified nucleotide in the sequencing primer generates an extended sequencing primer. In another implementation, the method further includes applying the rehydrated composition to a solid support comprising a nucleotide cluster, wherein the nucleotide cluster comprises a target polynucleotide.

A third aspect relates to a composition. The composition includes one or more functional protein; one or more functional protein activator; and one or more non-reducing sugar, wherein the composition is lyophilised.

In one implementation, the functional protein comprises a polymerase, a recombinase, a DNA binding protein, or a combination thereof. In one implementation, the functional protein activator is magnesium, a magnesium salt, or other magnesium derivative, or a combination thereof.

In one implementation, the one or more non-reducing sugar is trehalose, sucrose, inositol, maltodextrin, or dextran, mannitol, raffinose, cyclodextrin, melezitose, sorbitol, or a combination thereof. In one implementation, the composition comprises at least about 5 wt. % non-reducing sugar. In one implementation, the composition includes about 5 wt. % or less non-reducing sugar.

In one implementation, the composition is a microsphere, a cake, a powder, or a combination thereof. In one implementation, the composition has a cross-section of between about 0.1 mm and about 25 mm. In one implementation, when the composition is a microsphere, the microsphere is spherical, elliptical, or toroidal.

In one implementation, the composition comprises less than about 1 wt. % glycerol. In one implementation, the composition comprises about 5 wt. % or less of a crowding agent. In one implementation, the crowding agent comprises polyethylene glycol (PEG), polyvinyl pyrrolidone, dextran, maltodextrin, ficoll, polyacrylamide, or any combination thereof.

In one implementation, the composition further includes one or more recombinase loading protein, nucleotide triphosphate (dNPT), ATP, ATP analog, buffer, reducing agent, creatine kinase, or a combination thereof. In one implementation, the polymerase is a DNA polymerase. In one implementation, the DNA binding protein is a single-stranded DNA binding protein. In one implementation, the composition has a moisture content below about 10 wt. %.

A fourth aspect relates to a method of rehydration. The method of rehydration includes providing a composition including one or more functional protein; one or more functional protein activator; and one or more non-reducing sugar, wherein the composition is lyophilised; and mixing said composition with a rehydration solution under conditions effective to rehydrate the composition.

In one implementation, the rehydration solution is water, ethanolamine, or a combination thereof. In one implementation, the method further includes using the rehydrated composition in an exclusion amplification process.

A fifth aspect relates to a kit. The kit includes a composition including one or more modified nucleotide, wherein the modified nucleotide comprises a purine or pyrimidine base and a sugar moiety having a 3'-hydroxy blocking group, and a radical scavenger, wherein the composition is lyophilised; and a composition including one or more functional protein; one or more functional protein activator; and one or more non-reducing sugar, wherein the composition is lyophilised.

A sixth aspect relates to a cartridge. The cartridge includes a flow cell comprising: a reagent reservoir, wherein the reagent reservoir comprises a composition including one or more modified nucleotide, wherein the modified nucleotide comprises a purine or pyrimidine base and a sugar moiety having a 3'-hydroxy blocking group, and a radical scavenger, wherein the composition is lyophilised.

A seventh aspect relates to a cartridge. The cartridge includes a flow cell comprising: a reagent reservoir, wherein the reagent reservoir comprises a composition including one or more functional protein; one or more functional protein activator; and one or more non-reducing sugar, wherein the composition is lyophilised.

An eighth aspect relates to a cartridge. The cartridge includes a flow cell comprising: a first reagent reservoir, wherein the first reagent reservoir comprises a composition including one or more modified nucleotide, wherein the modified nucleotide comprises a purine or pyrimidine base and a sugar moiety having a 3'-hydroxy blocking group, and a radical scavenger, wherein the composition is lyophilised; and a second reagent reservoir, wherein the second reagent reservoir comprises a composition including one or more functional protein; one or more functional protein activator; and one or more non-reducing sugar, wherein the composition is lyophilised.

In accordance with the present disclosure, the compositions, methods, kits, and cartridges described herein have many advantages.

The problem of deblocking during lyophilisation is solved by addition of specific excipients as described herein such as radical scavengers.

Likewise, the problem of high dry ice usage and freight cost is solved by ambient temperature shipping through stabilized and lyophilised reagents as described herein. The problem of short reagent shelf life is solved by increasing the stability of reagents through stabilization and lyophilisation.

Current sequencing reagents are shipped in dry ice, and have varying stabilities at room temperature. To realize ambient shipping of the sequencing reagents, their stabilities were investigated and several of the unstable SBS reagents were stabilized using lyophilisation, or freeze drying.

The most unstable component of SBS sequencing reagents is the incorporation mix. Specifically, the fully functional nucleotides (ffNs) constitute the most unstable component of the incorporation mix. In this disclosure, the use of lyophilisation to stabilize incorporation mix as well as individual components of incorporation mix are disclosed. In addition, several other reagents were also stabilized using lyophilisation. The present disclosure also discusses the lyophilisation of linearization mix 2, resynthesis mix, scan mix, cleavage mix, and primers.

Current exclusion amplification process (ExAmp) or Recombinase Polymerase Amplification-RCA mixtures in solution require a separation of reagents into two or three tubes with Mg/PEG always separated from the protein components to achieve at least one year stability at −20° C. storage. Furthermore, the instability of the liquid-formulated reagent requires shipping at −20° C. as well, with the associated high shipping costs and far from ideal customer experience.

The present disclosure develops inter alia an ExAmp formulation and lyophilisation process that would enable a single tube formulation that can be lyophilised and resuspended with little to no impact on sequencing metrics. Here, an excipient reformulation is described using a non-reducing sugar and lyophilisation in the presence of Mg that produces a stable lyophilised cake that remains fully functional upon re-solubilization.

The lyophilised ExAmp single tube formulation enables ambient temperature shipping, eliminating the costs of dry ice shipments and improving customer experience by reducing the complexity of receiving and unpacking consumables. It also provides an all-in-one mix that minimizes complexity in cartridge design. The simplicity of a single tube ExAmp mix cannot be currently achieved with liquid formulations. Furthermore, the single tube ExAmp formulation presented here can be resuspended in water, which would ideally be the common solvent used for resuspension of all other lyophilised reagents on cartridge. Moreover, it increases stability of lyophilised reagent at high temperatures, allowing room temperature storage.

Moreover, cake lyophilisation possesses several drawbacks that could be overcome through lyophilisation into microspheres of raw components and dry compounding the components into a complex reagent mixture. One limitation of the traditional cake format is that it ties the lyophilised formulation to the vessel it will be lyophilised in. Variables like reagent volume (that may change due to low-throughput or high-throughput kit versions), excipient content, and active component concentration (which varies by platform) will change how the product lyophilises. Therefore, the process to produce lyophilised cakes depends on locking the complex reagent formulation and cartridge designs before lyophilisation cycle development can begin. This extends the development timeline since lyophilisation cycle optimization has to occur in series and makes formulation changes inflexible.

The adjustment from cakes to complex reagent microspheres as described herein decouples the formulation from the cartridge. This enables flexible cartridge design as well as variable fill volumes, but this still has the drawback of requiring complex formulation development to be locked before lyophilisation cycle development for a particular complex reagent can occur.

Lyophilising microspheres at the component level solves this issue since components for a reagent are known early on and lyophilisation cycle development for each individual component can start in parallel or even before reagent and cartridge development. The dry component microspheres can then be compounded (mixed together) and filled into the same container with the flexibility of varying the amounts (concentration) of each individual component that is appropriate for the application.

Another drawback with complex reagent cakes and microspheres is that the formulation conditions have to be a compromise so that each component will remain functional, but this formulation is not optimal for each component stability or activity. Lyophilising raw components into microspheres as described herein allows each component to be formulated in its optimized stable conditions. The dry components can then be combined into the same container with other microspheres that may have a different lyophilisation formulation optimized for storage stability. Due to the lyophilisation state, minimal molecular interaction should occur so that each component will remain in its optimal lyophilisation storage formulation until resuspension. Additionally, a microsphere of optimal reaction conditions could be added to change the resuspended liquid environment so conditions now match those for optimal activity.

As described above, current sequencing reagents are temperature sensitive and shipped in dry ice. The use of freeze drying is the gentlest method to stabilize multiple reagents for sequencing, to enable ambient shipping and storage. Traditional lyophilisation employs lyophilisation-in-place technique or more commonly known as cake lyophilisation. Despite being a common and widespread form of lyophilisation, cake lyophilisation possesses several drawbacks and could be overcome through lyophilisation in a bulk format. In this disclosure, bulk format of lyophilisation into microbeads and microspheres is demonstrated.

One key problem in cake lyophilisation is the need to have consumables and reagents in lockstep before lyophilisation development. This limits the timeline for lyophilisation development. However, in bulk lyophilisation into microspheres, consumables and reagent development are decoupled from lyophilisation development as raw materials can be lyophilised before other processing. Any reformulation will not require a redevelopment of lyophilisation process. Bulk lyophilisation of individual raw materials also eliminates the need for multiple well in cartridges as reagents can be combined into one well during filling step. This allows fewer wells in the cartridge and offers flexibility in cartridge design.

Another drawback in cake lyophilisation is long lyophilisation cycle. Generally, to achieve an elegant and dry lyophilised cake, a lyophilisation cycle for cake requires a minimum period of two to seven days. However, lyophilisation into microspheres generally takes one to two days to complete.

Cake is the most common format for lyophilisation. However, cake lyophilisation possesses several limitations that could be overcome through lyophilisation in the bead format. The problem of having individual vials for each reagent when lyophilising in the cake format is solved by lyophilising in the bead format, where several reagents such as ffNs and Pol beads can be combined into one vial. This allows both the flexibility in formulation, cartridge design and reduction in number of vials, which could potentially bring down the cost of goods sold.

The problem of a long lyophilisation cycle can be solved by lyophilising in the bead format. Large reagent volume in a cake format takes longer time to lyophilise as compared to the bead format. Lyophilising in the factory platform scale where reagent volumes are high would help save time and money in reducing the lyophilisation cycle. Lyophilisation in the bead format has also exhibited better performance as compared to the cake format for some reagents.

BRIEF DESCRIPTION OF THE DRAWINGS

FIG. 6 shows the formation of radicals in blue fully functionalized nucleotides (ffNs).

FIGS. 10A-10B show details of radical scavengers. FIG. 10A shows examples of phenolic antioxidants as radical scavengers. FIG. 10B shows the mechanism of phenolic antioxidant's ability to scavenge radicals.

FIG. 24 also shows the flexibility of varying concentration amounts of an active component or even combining several active components that are traditionally separated in individual vials due to storage formulation incompatibility.

DETAILED DESCRIPTION

Figure 1:
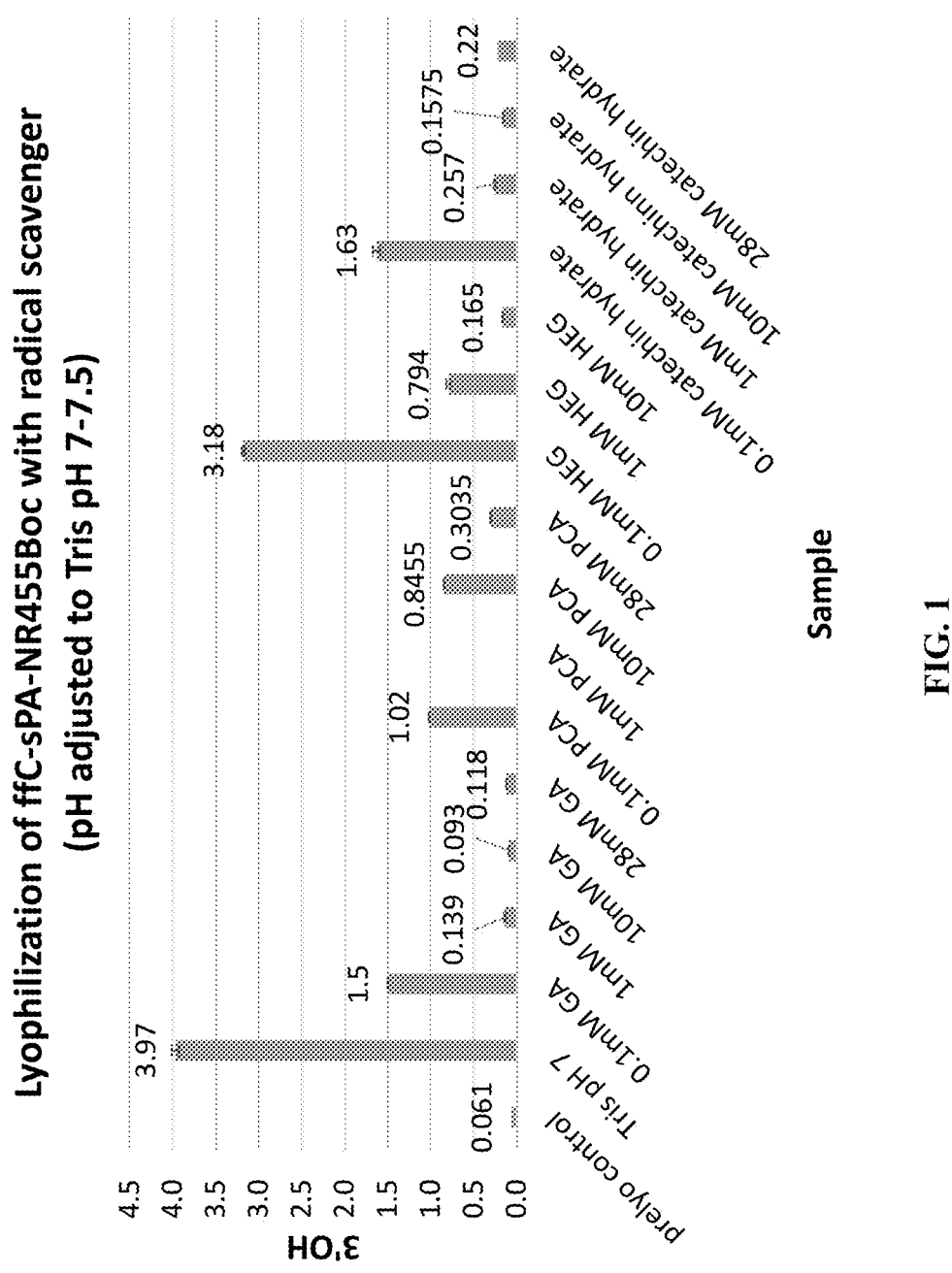
FIG. 1 shows lyophilisation of functionalized nucleotides with radical scavengers gallic acid (GA), protocatechuic acid (PCA), hydroxyethyl gallate (HEG), and catechin at various concentrations.

A first aspect relates to a composition. The composition includes one or more modified nucleotide, wherein the modified nucleotide comprises a purine or pyrimidine base and a sugar moiety having a 3'-hydroxy blocking group, and a radical scavenger, wherein the composition is lyophilised.

It is to be appreciated that certain aspects, modes, implementations, variations, and features of the present disclosure are described below in various levels of detail in order to provide a substantial understanding of the present technology. Unless otherwise noted, all technical and scientific terms used herein generally have the same meaning as commonly understood by one of ordinary skill in the art. The use of the term "including" as well as other forms is not limiting. The use of the term "having" as well as other forms is not limiting. As used in this disclosure, whether in a transitional phrase or in the body of the claim, the terms "comprise(s)" and "comprising" are to be interpreted as having an open-ended meaning. That is, the terms are to be interpreted synonymously with the phrases "having at least" or "including at least."

The terms "substantially", "approximately", "about", "relatively", or other such similar terms that may be used throughout this disclosure, including the claims, are used to describe and account for small fluctuations, such as due to variations in processing, from a reference or parameter. Such small fluctuations include a zero fluctuation from the reference or parameter as well. For example, fluctuations can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

It is further appreciated that certain features described herein, which are, for clarity, described in the context of separate implementations, can also be provided in combination in a single implementation. Conversely, various features which are, for brevity, described in the context of a single implementation, can also be provided separately or in any suitable sub-combination.

The terms "connect", "contact", and/or "coupled" include a variety of arrangements and assemblies. These arrangements and techniques include, but are not limited to, (1) the direct joining of one component and another component with no intervening components therebetween (i.e., the components are in direct physical contact); and (2) the joining of one component and another component with one or more components therebetween, provided that the one component being "connected to" or "contacting" or "coupled to" the other component is somehow in operative communication (e.g., electrically, fluidly, physically, optically, etc.) with the other component (optionally with the presence of one or more additional components therebetween). Components that are in direct physical contact with one another may or may not be in electrical contact and/or fluid contact with one another. Moreover, two components that are electrically connected, electrically coupled, optically connected, optically coupled, fluidly connected, or fluidly coupled may or may not be in direct physical contact, and one or more other components may be positioned between those two connected components.

As described herein, the term "array" may include a population of conductive channels or molecules that may attach to one or more solid-phase substrates such that the conductive channels or molecules can be differentiated from one another based on their location. An array as described herein may include different molecules that are each located at a different identifiable location (e.g., at different conductive channels) on a solid-phase substrate. Alternatively, an array may include separate solid-phase substrates each bearing a different molecule, where the different probe molecules can be identified according to the locations of the solid-phase substrates on a surface to which the solid-phase substrates attach or based on the locations of the solid-phase substrates in a liquid such as a fluid stream. Examples of arrays where separate substrates are located on a surface include wells having beads as described in U.S. Pat. No. 6,355,431, U.S. Pat. Publ. No. 2002/0102578, and WO 00/63437, all of which are hereby incorporated by reference in their entirety. Molecules of the array can be nucleic acid primers, nucleic acid probes, nucleic acid templates, or nucleic acid enzymes such as polymerases and exonucleases.

As described herein, the term "attached" may include when two things are joined, fastened, adhered, connected, or bound to one another. A reaction component, like a polymerase, can be attached to a solid phase component, like a conductive channel, by a covalent or a non-covalent bond. As described herein, the phrase "covalently attached" or "covalently bonded" refers to forming one or more chemical bonds that are characterized by the sharing of pairs of electrons between atoms. A non-covalent bond is one that does not involve the sharing of pairs of electrons and may include, for example, hydrogen bonds, ionic bonds, van der Waals forces, hydrophilic interactions, and hydrophobic interactions.

As described herein, the terms "polynucleotide" or "nucleic acids" refer to deoxyribonucleic acid (DNA), ribonucleic acid (RNA), or analogs of either DNA or RNA made from nucleotide analogs. The terms as used herein also encompasses cDNA, that is complementary, or copy DNA produced from an RNA template, for example by the action of reverse transcriptase. In one implementation, the nucleic acid to be analyzed, for example by sequencing through use of the described systems, is immobilized on a substrate (e.g., a substrate within a flow cell or one or more beads upon a substrate such as a flow cell, etc.). The term immobilized as used herein is intended to encompass direct or indirect, covalent, or non-covalent attachment, unless indicated otherwise, either explicitly or by context. The analytes (e.g., nucleic acids) may remain immobilized or attached to the support under conditions in which it is intended to use the support, such as in applications requiring nucleic acid sequencing. In one implementation, the template polynucleotide is one of a plurality of template polynucleotides attached to a substrate. In one implementation, the plurality of template polynucleotides attached to the substrate include a cluster of copies of a library polynucleotide as described herein.

Nucleic acids include naturally occurring nucleic acids or functional analogs thereof. Particularly useful functional analogs are capable of hybridizing to a nucleic acid in a sequence specific fashion or capable of being used as a template for replication of a particular nucleotide sequence. Naturally occurring nucleic acids generally have a backbone containing phosphodiester bonds. An analog structure can have an alternate backbone linkage including any of a variety of those known in the art such as peptide nucleic acid (PNA) or locked nucleic acid (LNA). Naturally occurring nucleic acids generally have a deoxyribose sugar (e.g. found in deoxyribonucleic acid (DNA)) or a ribose sugar (e.g. found in ribonucleic acid (RNA)).

In RNA, the sugar is a ribose, and in DNA a deoxyribose, i.e., a sugar lacking a hydroxyl group that is present in ribose. The nitrogen containing heterocyclic base can be purine or pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose may be bonded to N-1 of a pyrimidine or N-9 of a purine.

A nucleic acid can contain any of a variety of analogs of these sugar moieties that are known in the art. A nucleic acid can include native or non-native bases. A native deoxyribonucleic acid can have one or more bases selected from the group consisting of adenine, thymine, cytosine, or guanine and a ribonucleic acid can have one or more bases selected from the group consisting of uracil, adenine, cytosine or guanine. Useful non-native bases that can be included in a nucleic acid are known in the art.

The term nucleotide as described herein may include natural nucleotides, analogs thereof, ribonucleotides, deoxyribonucleotides, dideoxyribonucleotides and other molecules known as nucleotides. As described herein, a nucleotide may include a nitrogen containing heterocyclic base, a sugar, and one or more phosphate groups. Nucleotides may be monomeric units of a nucleic acid sequence, for example to identify a subunit present in a DNA or RNA strand. A nucleotide may also include a molecule that is not necessarily present in a polymer, for example, a molecule that is capable of being incorporated into a polynucleotide in a template dependent manner by a polymerase. A nucleotide may include a nucleoside unit having, for example, 0, 1, 2, 3 or more phosphates on the 5' carbon. Tetraphosphate nucleotides, pentaphosphate nucleotides, and hexaphosphate nucleotides may be useful, as may be nucleotides with more than 6 phosphates, such as 7, 8, 9, 10, or more phosphates, on the 5' carbon. Examples of naturally occurring nucleotides include, without limitation, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP.

Non-natural nucleotides include nucleotide analogs, such as those that are not present in a natural biological system or not substantially incorporated into polynucleotides by a polymerase in its natural milieu, for example, in a non-recombinant cell that expresses the polymerase. Non-natural nucleotides include those that are incorporated into a polynucleotide strand by a polymerase at a rate that is substantially faster or slower than the rate at which another nucleotide, such as a natural nucleotide that base-pairs with the same Watson-Crick complementary base, is incorporated into the strand by the polymerase. For example, a non-natural nucleotide may be incorporated at a rate that is at least 2 fold different, 5 fold different, 10 fold different, 25 fold different, 50 fold different, 100 fold different, 1000 fold different, 10000 fold different, or more when compared to the incorporation rate of a natural nucleotide. A non-natural nucleotide can be capable of being further extended after being incorporated into a polynucleotide. Examples include, nucleotide analogs having a 3' hydroxyl or nucleotide analogs having a reversible terminator moiety at the 3' position that can be removed to allow further extension of a polynucleotide that has incorporated the nucleotide analog. Examples of reversible terminator moieties are described, for example, in U.S. Pat. Nos. 7,427,673, 7,414,116, and 7,057,026, as well as WO 91/06678 and WO 07/123744, each of which is hereby incorporated by reference in its entirety. It will be understood that in some implementations a nucleotide analog having a 3' terminator moiety or lacking a 3' hydroxyl (such as a dideoxynucleotide analog) can be used under conditions where the polynucleotide that has incorporated the nucleotide analog is not further extended. In some implementations, nucleotide(s) may not include a reversible terminator moiety, or the nucleotides(s) will not include a non-reversible terminator moiety or the nucleotide(s) will not include any terminator moiety at all. In one implementation, the 3'-hydroxy blocking group is a reversible blocking group.

As used herein, the term "amplicon," when used in reference to a nucleic acid, means the product of copying the nucleic acid, wherein the product has a nucleotide sequence that is the same as or complementary to at least a portion of the nucleotide sequence of the nucleic acid. An amplicon may be produced by any of a variety of amplification methods that use the nucleic acid, or an amplicon thereof, as a template including, for example, polymerase extension, polymerase chain reaction (PCR), rolling circle amplification, ligation extension, or ligation chain reaction. An amplicon may be a nucleic acid molecule having a single copy of a particular nucleotide sequence (e.g., a PCR product) or multiple copies of the nucleotide sequence (e.g., a concatameric product of rolling circle amplification). A first amplicon of a target nucleic acid is typically a complementary copy. Subsequent amplicons are copies that are created, after generation of the first amplicon, from the target nucleic acid or from the first amplicon. A subsequent amplicon can have a sequence that is substantially complementary to the target nucleic acid or substantially identical to the target nucleic acid.

As described herein, the phrase "amplification site" refers to a site in or on an array where one or more amplicons can be generated. An amplification site can be further configured to contain, hold or attach at least one amplicon that is generated at the site.

The term "capacity" as used herein, when used in reference to a site and nucleic acid material, means the maximum amount of nucleic acid material that can occupy the site. For example, the term may refer to the total number of nucleic acid molecules that can occupy the site in a particular condition. Other measures can be used including, for example, the total mass of nucleic acid material or the total number of copies of a particular nucleotide sequence that can occupy the site in a particular condition. Typically, the capacity of a site for a target nucleic acid will be substantially equivalent to the capacity of the site for amplicons of the target nucleic acid.

The term "clonal population" as described herein includes a population of nucleic acids that is homogeneous with respect to a particular nucleotide sequence. The homogenous sequence is typically at least 10 nucleotides long, but can be even longer including for example, at least 50, at least 100, at least 250, at least 500, or at least 1000 nucleotides long. A clonal population can be derived from a single target nucleic acid or template nucleic acid. Typically, all of the nucleic acids in a clonal population will have the same nucleotide sequence. It will be understood that a small number of mutations (e.g., due to amplification artifacts) can occur in a clonal population without departing from clonality. It will also be understood that a small number of different target nucleic acid or template nucleic acid (e.g., due to a target nucleic acid that was not amplified) can occur in a clonal population without departing from clonality.

The term "cluster" refers to a discrete site on a solid support comprised of a plurality of identical immobilized nucleic acid strands and a plurality of identical immobilized complementary nucleic acid strands. The term "clustered array" refers to an array formed from such clusters or colonies. In this context, the term "array" is not to be understood as requiring an ordered arrangement of clusters.

As used herein, the term "different," when used in reference to nucleic acids, means that the nucleic acids have nucleotide sequences that are not the same as each other. Two or more nucleic acids can have nucleotide sequences that are different along their entire length. Alternatively, two or more nucleic acids can have nucleotide sequences that are different along a substantial portion of their length. For example, two or more nucleic acids can have target nucleotide sequence portions that are different from each other while also having a universal sequence region that are the same as each other.

As used herein, a protein can be "homologous" to a protein if the amino acid sequence of the protein possesses a specified amount of sequence similarity and/or sequence identity compared to the protein. Structural similarity of two amino acid sequences can be determined by aligning the residues of the two sequences (e.g., a candidate protein and the protein) to optimize the number of identical amino acids along the lengths of their sequences; gaps in either or both sequences are permitted in making the alignment in order to optimize the number of identical amino acids, although the amino acids in each sequence must nonetheless remain in their proper order. A candidate protein is the protein being compared to the protein.

In a comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions. A conservative substitution for an amino acid in a protein may be selected from other members of the class to which the amino acid belongs. For example, it is known in the art of protein biochemistry that an amino acid belonging to a grouping of amino acids having a particular size or characteristic (such as charge, hydrophobicity, or hydrophilicity) can be substituted for another amino acid without altering the activity of a protein, particularly in regions of the protein that are not directly associated with biological activity.

Thus, as used herein, homology to a protein as described herein, including, for example, homology to a DNA binding protein, may include a protein with at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to the protein.

As used herein, a "library" is a population of polynucleotides from a given source or sample. A library comprises a plurality of target polynucleotides.

A modified nucleotide as described herein includes one that has a purine or pyrimidine base and a sugar moiety having a 3'-hydroxy blocking group. In one implementation, the modified nucleotide is linked to a detectable label. In one implementation, the detectable label comprises a fluorophore. This disclosure encompasses nucleotides including a fluorescent label (or any other detection tag) that may be used in any method disclosed herein, on its own or incorporated into or associated with a larger molecular structure or conjugate. Additional examples of detectable labels are described in U.S. Pat. Nos. 7,541,444; 9,593,373; and 9,410, 199, all of which are hereby incorporated by reference in their entirety.

The fluorescent label can include compounds selected from any known fluorescent species, for example rhodamines or cyanines. A fluorescent label as disclosed herein may be attached to any position on a nucleotide base, and may optionally include a linker. In one implementation, the modified nucleotide is linked to a detectable label via a cleavable linker. The function of the linker is generally to aid chemical attachment of the fluorescent label to the nucleotide. In particular implementations, Watson-Crick base pairing can still be carried out for the resulting analogue. A linker group may be used to covalently attach a dye to the nucleoside or nucleotide. A linker moiety may be of sufficient length to connect a nucleotide to a compound such that the compound does not significantly interfere with the overall binding and recognition of the nucleotide by a nucleic acid replication enzyme. Thus, the linker can also include a spacer unit. The spacer distances, for example, the nucleotide base from a cleavage site or label.

The linker may be cleavable and the cleavage site may be located at a position on the linker that results in part of the linker remaining attached to the nucleotide base after cleavage or that results in the whole linker being removed from the nucleotide base. Exemplary linkers include azide- and allyl-containing cleavable moieties, disulfide linkers, acid labile moieties (including dialkoxybenzyl moieties, Sieber linkers, indole moieties, t-butyl Sieber moieties), electrophilically cleavable moieties, nucleophilically cleavable moieties, photocleavable moieties, cleavage under reductive conditions, oxidative conditions, cleavage via use of safety-catch moieties, and cleavage by elimination mechanisms. Examples of such moieties are described in WO03/048387 and U.S. Pat. No. 9,127,314, both of which are hereby incorporated by reference in their entirety.

The composition may include different modified nucleotides linked to different detectable labels. In some implementations, four different modified nucleotides may be linked to four different detectable labels. Alternatively, four different modified nucleotides may be labeled with two different detectable labels (for example, for two-channel sequencing by synthesis) or with a single detectable label (for example, for one-channel sequencing by synthesis).

As used herein, a "nucleoside" is structurally similar to a nucleotide, but is missing the phosphate moieties. An example of a nucleoside analogue is one in which the label is linked to the base and there is no phosphate group attached to the sugar molecule. The term "nucleoside" is used herein in its ordinary sense as understood by those skilled in the art. Examples include, but are not limited to, a ribonucleoside including a ribose moiety and a deoxyribonucleoside including a deoxyribose moiety. A modified pentose moiety is a pentose moiety in which an oxygen atom has been replaced with a carbon and/or a carbon has been replaced with a sulfur or an oxygen atom. A "nucleoside" is a monomer that may have a substituted base and/or sugar moiety.

The term "purine base" is used herein in its ordinary sense as understood by those skilled in the art, and includes its tautomers. Similarly, the term "pyrimidine base" is used herein in its ordinary sense as understood by those skilled in the art, and includes its tautomers. A non-limiting list of optionally substituted purine-bases includes purine, adenine, guanine, hypoxanthine, xanthine, alloxanthine, 7-alkylguanine (e.g. 7-methylguanine), theobromine, caffeine, uric acid and isoguanine. Examples of pyrimidine bases include, but are not limited to, cytosine, thymine, uracil, 5,6-dihydrouracil and 5-alkylcytosine (e.g., 5-methylcytosine).

The term substrate (or solid support), as described herein, may include any inert substrate or matrix to which nucleic acids can be attached, such as for example glass surfaces, plastic surfaces, latex, dextran, polystyrene surfaces, polypropylene surfaces, polyacrylamide gels, gold surfaces, and silicon wafers. For example, a substrate may be a glass surface (e.g., a planar surface of a flow cell channel). In one implementation, a substrate may include an inert substrate or matrix which has been "functionalized," such as by applying a layer or coating of an intermediate material including reactive groups which permit covalent attachment to molecules such as polynucleotides. Supports may include polyacrylamide hydrogel supported on an inert substrate such as glass. Molecules (e.g., polynucleotides) may be directly covalently attached to an intermediate material (e.g., a hydrogel). A support may include a plurality of particles or beads each having a different attached analyte.

As used herein, "derivative" or "analogue" means a synthetic nucleotide or nucleoside derivative having modified base moieties and/or modified sugar moieties. Such derivatives and analogs are discussed in, for example, Bucher, N. "Nucleotide Analogs. Synthesis and Biological Function," *Angewandte Chemie* 97:564 (1980) and Uhlmann et al., "Antisense Oligonucleotides: A New Therapeutic Principle," *Chemical Reviews* 90:543-584 (1990), both of which are hereby incorporated by reference in their entirety. Nucleotide analogs may also include modified phosphodiester linkages, including phosphorothioate, phosphorodithioate, alkyl-phosphonate, phosphoranilidate and phosphoramidate linkages. "Derivative", "analog", and "modified" as used herein, may be used interchangeably, and are encompassed by the terms "nucleotide" and "nucleoside" as described herein.

As used herein, the terms "solid phase" or "surface" are used to mean either a planar array wherein primers are attached to a flat surface, for example, glass, silica or plastic microscope slides or similar flow cell devices; beads, wherein either one or two primers are attached to the beads and the beads are amplified; or an array of beads on a surface after the beads have been amplified.

As used herein, "substantially free of" a material (including, for example, a crowding agent or a nucleic acid) refers to compositions having less than 10% of the material, less than 5% of the material, less than 4% of the material, less than 3% of the material, less than 2% of the material, or less than 1% of the material.

The composition described in the present aspect includes a radical scavenger. The term scavenger as used herein, refers to any molecule and/or compound that reacts with, and/or neutralizes, unwanted molecules that may have the capability of causing DNA photodamage and/or scission. For example, a scavenger may include, but is not limited to, a radical scavenger. A radical scavenger as described herein includes a substances, such as an antioxidant, that helps protect from damage caused by free radicals. Free radicals as described herein include unstable molecules that exist in an environment. In one implementation, the radical scavenger is a phenolic antioxidant. In one implementation, the radical scavenger comprises gallic acid (GA), hydroxyethyl gallate (HEG), protocatechuic acid (PCA), catechin, or a combination thereof.

In one implementation, the composition further includes one or more non-reducing sugar. The term "non-reducing sugar" as described herein may include any carbohydrate that is not oxidized by a weak oxidizing agent (an oxidizing agent that oxidizes aldehydes but not alcohols) in basic aqueous solution such as, but not limited to, water. A property of a non-reducing sugar includes that, in basic aqueous medium, the non-reducing sugar does not generate any compound containing an aldehyde group. In one implementation, the one or more non-reducing sugar is trehalose, sucrose, inositol, maltodextrin, or dextran, mannitol, raffinose, cyclodextrin, melezitose, sorbitol, or any combination thereof. The wt. % of the non-reducing sugar, when present, may range from about 0.001 wt. % to about 50 wt. % of the composition. For example, the wt. % of the non-reducing sugar may be between about 0.01 wt. % and about 99 wt. %. Alternatively, the wt. % of the non-reducing sugar, when present, may be between about 0.01 wt. % and about 75 wt. %, or between about 0.01 wt. % and about 65 wt. %, or between about 0.01 wt. % and about 55 wt. %, or between about 0.01 wt. % and about 50 wt. %, or between about 0.01 wt. % and about 45 wt. %, or between about 0.01 wt. % and about 35 wt. %, or between about 0.01 wt. % and about 25 wt. %, or between about 0.01 wt. % and about 15 wt. %, between about 0.01 wt. % and about 5 wt. %, or any range therebetween. In one implementation, the composition include at least about 5 wt. % non-reducing sugar. For example, the composition may include about 5 wt. %, about 6 wt. %, about 7 wt. %, about 8 wt. %, about 8 wt. %, about 8.5 wt. %, about 9 wt. %, about 9.5 wt. %, about 10 wt. %, about 11 wt. %, about 12 wt. %, about 13 wt. %, about 14 wt. %, about 15 wt. %, about 19 wt. %, about 19.5 wt. %, about 20 wt. %, about 25 wt. %, about 30 wt. %, about 35 wt. %, about 40 wt. %, about 45 wt. %, about 50 wt. %, or above 50 wt. %, or any amount therebetween of non-reducing sugar. In another implementation, the composition includes about 5 wt % or less non-reducing sugar. For example, the composition may include about 4.5 wt. %, about 4 wt. %, about 3.5 wt. %, about 3 wt. %, about 2.5 wt. %, about 2 wt. %, about 1.5 wt. %, about 1 wt. %, about 0.5 wt. %, about 0.4 wt. %, about 0.3 wt. %, about 0.2 wt. %, about 0.1 wt. %, about 0.05 wt. %, about 0.01 wt. %, about 0.001 wt. %, below 0.001 wt. %, or any amount therebetween of non-reducing sugar. The non-reducing sugar may be added in any amount suitable to produce a desired effect.

In some implementations, the composition is stable when stored at 37° C. a period of time that is less than 7 days, or more than 7 days. For example the composition may be stable for months and even more than a year. The composition may be stable, in certain examples, for a period of 5 days, 7 days, 10 days, 14 days, 30 days, 31 days, 50 days, 100 days, 200 days, 300 days, 365 days, 400 days, 500 days, 600 days, 700 days, 800 days, 900 days, 1,000 days, or any period of time therebetween. A DNA polymerase is considered "stable" when the DNA polymerase, after being stored at up to 37° C. for a period of, for example, 7 days or 26 days or more, retains at least 75%, more preferably at least 80% of the activity of the same quantity of DNA polymerase prior to storage. In some implementations, the activity of a DNA polymerase may be measured using a FRET assay. A modified nucleotide is considered as "stable" when at least 99.8% of each of the modified nucleotides maintain the 3'-hydroxy protecting groups, after being stored at up to 37° C. for a period of 7 days or 26 days or more, when the modified nucleotides prior to storage included 99.92% % having 3'-hydroxy protecting groups, as measured by HPLC.

Achieving a composition that includes one or both modified nucleotides and a DNA polymerase, wherein both the modified nucleotides and the DNA polymerase are stable after being stored at up to 37° C. for a period of 7 days or 26 days or more is not trivial. Indeed, possible interactions between the components was thought to contraindicate mixing the components prior to lyophilisation. Moreover, the conditions that allow for the stability of the modified nucleotides may be contrary to the conditions that allow for the stability of the DNA polymerase.

The compositions described herein may be lyophilised. In one implementation, the composition includes a cake, a bead, or a powder. In another implementation, the composition may be a microsphere, a cake, or a combination thereof.

When the composition is in the form of a cake or a bead (e.g., a microsphere), the composition may exhibit mechanical rigidity. "Mechanical rigidity" of a bulk composition (for example, of a cake or bead) as used herein refers to a bulk composition that exhibits a loss of mass of up to 5%, more preferably up to 1%, even more preferably up to 0.5%, and most preferably up to 0.1% from the bulk composition after the bulk composition is subjected to mechanical stress such as vibration or shock stress. Maintaining mechanical rigidity of a bulk composition helps to prevent the loss of a lyophilised material during shipping. If, for example, a cake or a bead lacks mechanical stability, incomplete rehydration may occur, resulting in a loss of efficiency in a sequencing reaction. Incomplete rehydration could be caused by the unpredictable position of the lyophilized material where lyo fragments or shed powders might be located beyond the line of rehydration.

As used herein, "microsphere" includes spherical particles or beads that have a diameter of 0.1 μm to 25,000 μm. For example, a microsphere may have a diameter of about 0.1 μm, 0.5 μm, 1 μm, 10 μm, 20 μm, 25 μm, 30 μm, 35 μm, 40 μm, 50 μm, 60 μm, 70 μm, 80 μm, 90 μm, 100 μm, 150 μm, 200 μm, 300 μm, 400 μm, 500 μm, 600 μm, 700 μm, 800 μm, 900 μm, 1000 μm, 10,000 μm, 25,000 μm, or any diameter between about 0.1 μm and about 25,000 μm. In one implementation, the encapsulated microsphere has a diameter between about 100 μm and about 1000 μm. In one implementation, the microsphere has a cross-section of between about 0.1 mm and about 25 mm. In one implementation, the microsphere has a cross-section of between about 0.1 mm and about 1 mm. In one implementation, the composition has a cross-section of greater than about 1 mm. In one implementation, the composition has a diameter of about 0.1 mm, 1 mm, 2 mm, 3 mm, 4 mm, 5 mm, 6 mm, 7 mm, 8 mm, 9 mm, 10 mm, 50 mm, 100 mm, 200 mm, 300 mm, 400 mm 500 mm, 600 mm, 700 mm, 800 mm, 900 mm, 1,000 mm, or any diameter between about 0.1 mm and about 1,000 mm.

In one implementation, the microsphere is spherical, elliptical, or toroidal. Microspheres are generally comprised of a polymer shell, for example, biodegradable polymers. Microspheres in accordance with the present disclosure include those prepared by conventional techniques, which are known to those skilled in the art. For example, microspheres may be prepared by freezing a liquid into frozen pellets, followed by placing frozen microspheres in a dryer, for example, a rotary dryer.

Macrospheres in accordance with the present disclosure include those prepared by conventional techniques, which are known to those skilled in the art. The compositions, methods, kits, cartridges, and systems described herein may include a single microsphere, or may include a plurality of microspheres and may thereby form a macrosphere. For example, the composition described herein may include anywhere between 1 and over 1,000,000 microspheres. In one implementation, the composition includes 1 microsphere, or less than 100 microspheres, or less than 500 microspheres, or any number of microspheres between about 1 and about 1,000,000. In one implementation, for example in a macrosphere, compositions and/or reagents are different.

Lyophilisation in accordance with the present disclosure includes methods in accordance with conventional techniques, which are known to those skilled in the art. Lyophilisation is also referred to herein as freeze-drying. In the present disclosure, the term "lyophilize" or "lyophilizate" will be used as equivalent terms of "lyophilised", "lyophilizate", or "freeze-dried" e.g., with respect to a compositions, systems, or methods described herein.

Lyophilisable formulations can be reconstituted into solutions, suspensions, emulsions, or any other suitable form for administration or use. Lyophilisable formulations are typically first prepared as liquids, then frozen and lyophilised. The total liquid volume before lyophilisation can be less than, equal to, or more than, the final reconstituted volume of the lyophilised formulation. The final reconstituted volume of the lyophilised formulation may be less than the total liquid volume before lyophilisation, or may be greater than the total liquid volume before lyophilisation, or may be the same total liquid volume before lyophilisation. The lyophilisation process is known to those of ordinary skill in the art, and typically includes sublimation of water from a frozen formulation under controlled conditions.

Lyophilised formulations can be stored at a wide range of temperatures. Lyophilised formulations may be stored below 25° C., for example, refrigerated at 2-8° C., or at room temperature (e.g., approximately 25° C.). Lyophilised formulations may be stored at about 0° C., 5° C., 10° C., 15° C., 20° C., 25° C., 30° C., 35° C., 37° C., or any temperature between 37° C. and −80° C. For example, they compositions may be stored between about 15° C. and about 37° C., below about 25° C., at about 4-20° C.; below about 4° C.; below about −20° C.; about −40° C.; about −70° C., or about −80° C. Stability of the lyophilised formulation may be determined in a number of ways known in the art, for example, by visual appearance of the microsphere and/or cake and/or by moisture content. The compositions of the present disclosure can also withstand temperature excursions that might occur during shipping, for example, up to 70° C. The compositions, methods, kits, cartridges, and systems described herein, in one implementation, exhibit stability when stored for a period of time, for example, 10 days, 14 days, 20 days, 26 days, 30 days, 60 days, 100 days, 200 days, 300 days, 365 days, or more when stored at a temperature of 37° C. for example.

Lyophilised formulations are typically rehydrated (interchangeably referred to herein as "reconstituted") for use by addition of an aqueous solution to dissolve the lyophilised formulation. A wide variety of aqueous solutions can be used to reconstitute a lyophilised formulation including water, saline, or another electrolyte or non-electrolyte diluent.

Preferably, the lyophilised compositions described herein are reconstituted using water. Lyophilised formulations may be rehydrated with a solution comprising water (e.g., USP WFI, or water for injection) or bacteriostatic water (e.g., USP WFI with 0.9% benzyl alcohol). However, solutions comprising additives, buffers, excipients, and/or carriers can also be used and are described herein.

Freeze-dried or lyophilised formulations are typically prepared from liquids, that is, from solutions, suspensions, emulsions, and the like. Thus, the liquid that is to undergo freeze-drying or lyophilisation preferably comprises all components desired in a final reconstituted liquid formulation. As a result, when rehydrated or reconstituted, the freeze-dried or lyophilised formulation will render a desired liquid formulation upon reconstitution.

In one implementation, the compositions described herein, when lyophilised, include a moisture content of below about 10 wt. %. For example, the moisture content may be less than about 9.5 wt. %, less than about 9 wt. %, less than about 8.5 wt. %, less than about 8 wt. %, less than about 7.5 wt. %, less than about 7 wt. %, less than about 6.5 wt. %, less than about 6 wt. %, less than about 5.5 wt. %, less than about 5 wt. % water, less than about 4.5 wt. %, less than about 4 wt. %, less than about 3.5 wt. %, less than about 3 wt. %, less than about 2.5 wt. %, less than about 2 wt. %, less than about 1.5 wt. %, less than about 1 wt. %, less than about 0.5 wt. %, less than about 0.1 wt. % water, or any amount therebetween. In one implementation, there is no measurable content of water in the lyophilised composition.

In one implementation, the composition further includes, but is not limited to, one or more additional reagents, for example, one or more enzyme, salt, surfactant, buffering agent, enzyme inhibitor, primer, nucleotide, organic osmolite, magnetic bead, molecular probe, crowding agent, small molecule, labelled-nucleotide, or any combination thereof. In a preferred implementation, the composition does not contain and/or is not surrounded by an aqueous medium.

As used herein, the term "reagent" describes a single agent or a mixture of two or more agents useful for reacting with, interacting with, diluting, or adding to a sample, and may include the compositions described herein as well as agents used in nucleic acid reactions, including, for example buffers, chemicals, enzymes, polymerase, primers including those having a size of less than 50 base pairs, template nucleic acids, nucleotides, labels, dyes, or nucleases. In one implementation, the reagent includes a polymerase, for example, Pol 812, 129 DNA polymerase, Taq polymerase, Bsu polymerase, or any combination thereof. In some implementations, the reagent may further or alternatively include a lysozyme, proteinase K, random hexamers, transposase (for example, Tn5), primers (for example, P5 and P7 adaptor sequences), ligase, catalyzing enzyme, deoxynucleotide triphosphates, buffers, or divalent cations. The reagent may further or alternatively include, for example, bead-linked transposomes (BLT), Tris pH7, MgCl$_2$, Mg acetate, Mg sulfate, indexed primers, Q5 polymerase, Bst3.0, Tris pH9, dNTPs, NaCl, betaine, or any combination thereof. A reagent as described herein may, in certain implementations, include enzymes such as polymerases, ligases, recombinases, or transposases; binding partners such as antibodies, epitopes, streptavidin, avidin, biotin, lectins or carbohydrates; or other biochemically active molecules. Other examples reagents include reagents for a biochemical protocol, such as a nucleic acid amplification protocol, an affinity-based assay protocol, an enzymatic assay protocol, a sequencing protocol, and/or a protocol for analyses of biological fluids. According to some implementations disclosed herein, a reagent may include one or more beads, in particular magnetic beads, depending on specific workflows and/or downstream applications.

In one implementation, a reagent in accordance with the present disclosure is a polymerase. As used herein, the term "polymerase" is intended to be consistent with its use in the art and includes, for example, an enzyme that produces a complementary replicate of a nucleic acid molecule using the nucleic acid as a template strand. Typically, DNA polymerases bind to the template strand and then move down the template strand sequentially adding nucleotides to the free hydroxyl group at the 3' end of a growing strand of nucleic acid. DNA polymerases typically synthesize complementary DNA molecules from DNA templates and RNA polymerases typically synthesize RNA molecules from DNA templates (transcription). Polymerases can use a short RNA or DNA strand, called a primer, to begin strand growth. Some polymerases can displace the strand upstream of the site where they are adding bases to a chain. Such polymerases are said to be strand displacing, meaning they have an activity that removes a complementary strand from a template strand being read by the polymerase. Exemplary polymerases having strand displacing activity include, without limitation, the large fragment of Bst (*Bacillus stearothermophilus*) polymerase, exo-Klenow polymerase or sequencing grade T7 exo-polymerase. Some polymerases may degrade the strand in front of them, effectively replacing it with the growing chain behind (5' exonuclease activity). Some polymerases have an activity that may degrade the strand behind them (3' exonuclease activity). Some useful polymerases have been modified, either by mutation or otherwise, to reduce or eliminate 3' and/or 5' exonuclease activity.

Polymerase in accordance with the present disclosure may include any polymerase that can tolerate incorporation of a phosphate-labeled nucleotide. Examples of polymerases that may be useful in accordance with the present disclosure include but are not limited to phi29 polymerase, a klenow fragment, DNA polymerase I, DNA polymerase III, GA-1, PZA, phi15, Nf, G1, PZE, PRD1, B103, GA-1, 9oN polymerase, Bst, Bsu, T4, T5, T7, Taq, Vent, RT, pol beta, pol gamma, and combinations thereof. Polymerases engineered to have specific properties may be used. In one implementation, the polymerase may be useful for sequencing ("sequencing polymerase").

A primer as disclosed herein includes a nucleic acid molecule that can hybridize to a target sequence of interest. In several implementations, a primer may function as a substrate onto which nucleotides can be polymerized by a polymerase. However, in some examples, the primer can become incorporated into the synthesized nucleic acid strand and provide a site to which another primer can hybridize to prime synthesis of a new strand that is complementary to the synthesized nucleic acid molecule. The primer can include any combination of nucleotides or analogs thereof. In one implementation, the primer is a single-stranded oligonucleotide or polynucleotide.

Non-limiting examples of nucleic acid molecules that may be included in the compositions described above also include, DNA, such as genomic or cDNA; RNA, such as mRNA, sRNA or rRNA; or a hybrid of DNA and RNA. The composition may further comprise a labelled-nucleotide.

The term "salt" may include salts prepared from toxic or non-toxic acids or bases including inorganic acids and bases and organic acids and bases. Salts may be prepared from, for example, pharmaceutically acceptable non-toxic acids including inorganic and organic acids.

Any surfactant known to one skilled in the art may be also be included in the composition, particularly, when the composition is lyophilised. The surfactant may be non-ionic or ionic (specifically cationic or anionic) or may be zwitterionic. A surfactant as described herein includes Tween-20, Tween 80, CHAPS, or other detergent such as Brij-L23, Pluronic-F127, or a combination thereof. Examples of suitable surfactants include but are not limited to polyacrylate surfactants, silicone surfactants, and/or other commercially available surfactants or detergents. The composition described herein may include an anionic surfactant which contains an anionic functional group at one end, such as a sulfate, sulfonate, phosphate, and carboxylate functional group. The reagent may comprise a neutral surfactant, for example, a polyethelene glycol lauryl ether.

The composition may further, or in the alternative, include an enzyme inhibitor, a molecular probe, a crowding agent, organic osmolite, cyclodextrin, adenosine triphosphate (ATP), ethylenediaminetetraacetic acid (EDTA), creatine kinase, creatine phosphate, palladium, lipoic acid, hexaethylene glycol, trihydroxypropanephosphine, sodium ascorbate, or any combination thereof. An enzyme inhibitor as described herein includes any a molecule that binds to an enzyme and decreases its activity. A molecular probe as described herein includes, for example, digoxigenin, 8-Anilinonaphthalene-1-sulfonic acid ("ANS"), porphyrin, BODIPY, cyanine, or any combination thereof. A crowding agent as described herein includes any crowding agent known to those skilled in the art. Examples include, but are not limited to, polyethylene glycol, ficoll, dextran, and serum albumin. In one implementation, the composition includes about 5 wt. %, about 4 wt. 5%, about 3 wt. 5, about 2 wt. %, about 1 wt. %, less than about 1 wt. % of a crowding agent, for example, less than about 0.001 wt. %, about 0.001 wt. %, about 0.005 wt. %, about 0.01 wt. %, about 0.05 wt. %, about 0.1 wt. %, about 0.5 wt. %, about 1 wt. %, or any amount or range therebetween. In one implementation, there is no measurable content of crowding agent in the composition.

In one implementation, the composition includes glycerol. The amount of glycerol may vary, but in one implementation the composition includes less than about 1 wt. % glycerol. For example, the composition may include less than about 0.001 wt. %, about 0.001 wt. %, about 0.005 wt. %, about 0.01 wt. %, about 0.05 wt. %, about 0.1 wt. %, about 0.5 wt. %, about 1 wt. %, or any amount or range therebetween. In one implementation, there is no measurable content of glycerol in the composition.

Those skilled in the art of sequencing technologies will appreciate there are additional reagents that may be useful in the compositions, methods, kits, systems, and cartridges of the present disclosure that are not explicitly described herein.

The composition as described herein may, in one implementation, further include one or more additional agents such as a functional protein activator. In one implementation, the functional protein activator includes magnesium, a magnesium salt or other magnesium derivative, or a combination thereof.

In one implementation, the composition may include T4 Polynucleotide Kinase (T4 PNK), which is a homo tetramer that has two distinctive functions in DNA and RNA repair: the 5'-kinase activity and 3'-phosphatase activity. The N-terminal domain of the enzyme transfers phosphate from ATP to the 5-OH terminus of DNA and RNA. The phosphorylation reaction is reversible; in the presence of ADP, T4PNK cleaves 5' phosphate. In addition, T4PNK exhibits exchange activity to exchange an existing phosphate group presents at the 5' end of a DNA molecule with a phosphate from another phosphate donor. The C-terminal domain of the enzyme catalyzes the phosphatase activity, which removes phosphate group from the 3'-terminus of DNA and RNA.

In one implementation, the composition further includes a reducing agent. The reducing agent may include for example 2-mercaptoethanol, Tris(2-carboxyethyl)-phosphate hydrochloride (TCEP), or tris(hydroxypropyl)phosphine (THP), or a combination thereof.

In one implementation, the composition further includes tris(hydroxypropyl)phosphine (THP) and an alkanolamine. The composition, after being rehydrated, may be used as a cleavage composition. In one implementation, the cleavage composition may be used to remove a detectable label from a modified nucleotide and to regenerate a 3'-hydroxy protecting group. In one implementation, the alkanolamine includes ethanolamine, aminomethyl propanol, heptaminol, isoetarine, a propanolamine, sphingosine, methanolamine, dimethylethanolamine, or N-methylethanolamine. In some implementations, the alkanolamine includes ethanolamine.

Notably, a composition including THP—which is difficult to lyophilise—and ethanolamine—a volatile buffer that is not ideal for lyophilisation—can nevertheless be lyophilised, allowing the reagent to be shipped at ambient temperature. Moreover, after being lyophilised THP can retain its ability to facilitate a Staudinger reaction.

The compositions described herein may be used for multiple sequential co-assays comprising lysis, DNA analysis, RNA analysis, protein analysis, tagmentation, nucleic acid amplification, nucleic acid sequencing, DNA library preparation, SBS technology, assay for transposase accessible chromatic using sequencing (ATAC-seq), contiguity-preserving transposition (CPT-seq), single cell combinatorial indexed sequencing (SCI-seq), or single cell genome amplification, or any combination thereof performed sequentially. In one implementation, the composition is used for performing multiple co-assay reactions. The compositions, methods, kits, cartridges, and systems described herein may, in one implementation, improve sequencing quality, enable one-pot library prep, and simplify manufacturing. As used herein, the term "one-pot reaction" may also be referred to as "transfer-free reaction."

The compositions, methods, kits, cartridges, and systems described herein may be prepared for various stages of sequencing including, but not limited to, sample extraction, library preparation, enrichment, clustering, and sequencing. The composition may include any number of different reagents from those described herein or any reagent that may be useful in promoting utility of sequencing systems, for example, SBS technology.

In one implementation, a biological sample contacts the composition. A biological sample, may include, for example, whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. A biological sample can include nucleic acids, such as DNA, genomic DNA, RNA, mRNA or analogs thereof; nucleotides such as deoxyribonucleotides, ribonucleotides or analogs thereof such as analogs having terminator moieties such as those described in Bentley et al., "Accurate Whole Human Genome Sequencing Using Reversible Terminator Chemistry," *Nature* 456:53-59 (2008); WO/2013/131962; U.S. Pat. No. 7,057,026; WO/2008/042067; WO/2013/117595; U.S. Pat. Nos. 7,329,492; 7,211,414; 7,315,019; 7,405,281; and U.S. Patent Pub. No. 20080108082, all of which are hereby incorporated by reference in their entirety.

A second aspect relates to a method of rehydration. The method includes providing a composition including one or more modified nucleotide, wherein the modified nucleotide comprises a purine or pyrimidine base and a sugar moiety having a 3'-hydroxy blocking group, and a radical scavenger, wherein the composition is lyophilised; and mixing said composition with a rehydration solution under conditions effective to rehydrate the composition.

This aspect is carried out in accordance with the previously described aspect, in particular with regard to the characteristics of the compositions described.

A rehydration (or reconstitution) solution as used herein may include water, deionized water, saline solutions, acidic solutions, basic solutions, detergent solutions and/or buffers, and may be in accordance with rehydration solutions previously described. In one implementation, the rehydration solution is water, ethanolamine, or a combination thereof. In one implementation, reagents described herein having varying concentrations, types of enzymes, and different amounts of co-factors, salts, pHs, and more, can be rehydrated with water alone, or even atmospheric water capture. Additional additives as described herein may be provided in the rehydration solution to further improve control of release of microspheres.

In one implementation, a pH in the rehydration solution is between about 7.0 and about 10.0. A pH of the rehydration solution may be, for example, about 7.0, about 7.5, about 8.0, about 8.5, about 9.0, about 9.5, about 10.0, or any amount therebetween. Rehydration time will vary depending on composition content and reaction conditions (e.g., reagents, temperature, pH). In one implementation, rehydration time may be between 0.01 seconds and 5 hours. For example, rehydration time may be about 0.01 seconds, 0.1 seconds, 1 second, 10 seconds, 30 seconds, 45 seconds, 60 seconds, 5 minutes, 10 minutes, 12 minutes, 15 minutes, 20 minutes, 30 minutes, 40 minutes, 50 minutes, 60 minutes, 70 minutes, 80 minutes, 90 minutes, 2 hours, 5 hours, or any amount of time therebetween.

In one implementation, the method further includes using the rehydrated composition in a sequencing by synthesis process. In another implementation, the method further includes exposing the rehydrated composition to a sequencing primer, wherein incorporation of the one or more modified nucleotide in the sequencing primer generates an extended sequencing primer. In another implementation, the method further includes applying the rehydrated composition to a solid support comprising a nucleotide cluster, wherein the nucleotide cluster comprises a target polynucleotide.

A third aspect relates to a composition. The composition includes one or more functional protein; one or more functional protein activator; and one or more non-reducing sugar, wherein the composition is lyophilised.

This aspect is carried out in accordance with the previously described aspects, in particular with regard to the characteristics of the compositions described.

In one implementation, the functional protein comprises a polymerase, a recombinase, a DNA binding protein, or a combination thereof. In one implementation, the DNA binding protein is a single-stranded DNA binding protein.

In one implementation, the one or more non-reducing sugar is trehalose, sucrose, inositol, maltodextrin, or dextran, mannitol, raffinose, cyclodextrin, melezitose, sorbitol, or a combination thereof.

A fourth aspect relates to a method of rehydration. The method of rehydration includes providing a composition including one or more functional protein; one or more functional protein activator; and one or more non-reducing sugar, wherein the composition is lyophilised; and mixing said composition with a rehydration solution under conditions effective to rehydrate the composition.

This aspect is carried out in accordance with the previously described aspects, in particular with regard to the characteristics of the compositions described.

One method of bridge amplification is exclusion amplification (ExAmp), also known as kinetic exclusion amplification. ExAmp includes a recombinase-facilitated polymerase amplification (also referred to as RCA or RPA). See Pipenburg et al., "DNA Detection Using Recombination Proteins," *PLOS Biol.* 4(7):e204 (2006), which is hereby incorporated by reference in its entirety. ExAmp uses a patterned array and isothermal conditions to amplify a library. ExAmp discourages polyclonal clusters within a well of the patterned array; the fast amplification of the initial DNA template during cluster formation prevents other DNA templates from hybridizing in the well. In one implementation, the method further includes using the rehydrated composition in an exclusion amplification process.

A fifth aspect relates to a kit. The kit includes a composition including one or more modified nucleotide, wherein the modified nucleotide comprises a purine or pyrimidine base and a sugar moiety having a 3'-hydroxy blocking group, and a radical scavenger, wherein the composition is lyophilised; and a composition including one or more functional protein; one or more functional protein activator; and one or more non-reducing sugar, wherein the composition is lyophilised.

This aspect is carried out in accordance with the previously described aspects, in particular with regard to the characteristics of the compositions described.

A sixth aspect relates to a cartridge. The cartridge includes a flow cell comprising: a reagent reservoir, wherein the reagent reservoir comprises a composition including one or more modified nucleotide, wherein the modified nucleotide comprises a purine or pyrimidine base and a sugar moiety having a 3'-hydroxy blocking group, and a radical scavenger, wherein the composition is lyophilised.

This aspect is carried out in accordance with the previously described aspects, in particular with regard to the characteristics of the compositions described.

Exemplary cartridges and configurations are described in, for example, U.S. Pat. Nos. 8,637,242; 8,951,781; 9,116, 139; 9,193,996; 9,387,476; 9,410,977; 9,650,669; 9,777, 325; 9,782,770, and U.S. Publication No. 2017/0246635, all of which are hereby incorporated by reference in their entirety. Exemplary flow cells are described, for example, in U.S. Pat. Nos. 8,241,573 and 8,951,781, both of which are hereby incorporated by reference in their entirety.

Additionally or alternatively, a cartridge can include separate reservoirs and fluidic systems used to carry out amplification methods and to carry out detection methods. Examples of integrated sequencing systems that are capable of creating amplified nucleic acids and also determining the sequence of the nucleic acids include, without limitation, the MiSeq™ platform (Illumina, Inc., San Diego, CA) and devices described in U.S. Pat. No. 8,951,781, which is hereby incorporated by reference in its entirety.

A seventh aspect relates to a cartridge. The cartridge includes a flow cell comprising: a reagent reservoir, wherein the reagent reservoir comprises a composition including one or more functional protein; and one or more functional protein activator; and one or more non-reducing sugar, wherein the composition is lyophilised.

This aspect is carried out in accordance with the previously described aspects, in particular with regard to the characteristics of the compositions described.

An eighth aspect relates to a cartridge. The cartridge includes a flow cell comprising: a first reagent reservoir, wherein the first reagent reservoir comprises a composition including one or more modified nucleotide, wherein the modified nucleotide comprises a purine or pyrimidine base and a sugar moiety having a 3'-hydroxy blocking group, and a radical scavenger, wherein the composition is lyophilised; and a second reagent reservoir, wherein the second reagent reservoir comprises a composition including one or more functional protein; one or more functional protein activator; and one or more non-reducing sugar, wherein the composition is lyophilised.

This aspect is carried out in accordance with the previously described aspects, in particular with regard to the characteristics of the compositions described.

It should be appreciated that all combinations of the foregoing concepts and additional concepts discussed in greater detail herein (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

In the present disclosure, reference is made to the accompanying drawings that form a part hereof, and in which is shown by way of illustration specific implementations which may be practiced. These implementations are described in detail to enable those skilled in the art to practice the disclosure, and it is to be understood that other implementations may be utilized and that structural, logical and electrical changes may be made without departing from the scope of the present disclosure. The following description of example implementations is, therefore, not to be taken in a limited sense.

The present disclosure may be further illustrated by reference to the following examples.

EXAMPLES

The following examples are intended to illustrate, but by no means are intended to limit, the scope of the present disclosure as set forth in the appended claims.

Example 1—Stabilization of Nucleotides with Use of Radical Scavengers

The problem of deblocking during lyophilisation is solved by addition of excipients such as radical scavengers.

The AZM (azidomethyl) group in fully functional nucleotides (ffNs) in the sequencing platform serves to allow single incorporation during sequencing by synthesis (SBS). This functional group is then cleaved by a reducing agent such as THP to form a 3'OH group, in which the next nucleotide can then be incorporated.

The AZM group is also prone to hydrolysis in water, resulting in its cleavage and subsequent formation of 3'OH group. This process is also termed deblocking. Deblocking is observed when solution of ffN containing incorporation mix, or solely ffNs, are heat stressed. Current specifications for amount of 3'OH in incorporation mix for each ffN is set at <0.2%. There are efforts to stabilize the ffNs through the process of lyophilisation. However, deblocking is still seen after exposure to elevated temperatures. Increase in 3'OH can cause increase in prephasing in the sequencing metrics and lower the Q30 score. Presence of deblocking will be a challenge to fulfill ambient shipping requirements, therefore, alternative methods are explored to reduce deblocking in ffNs, one of which is the use of radical scavengers.

It is proposed that the problem of deblocking can be reduced with the use of radical scavengers, thereby allowing to reach the goal of ambient shipping and storage.

Figure 2:
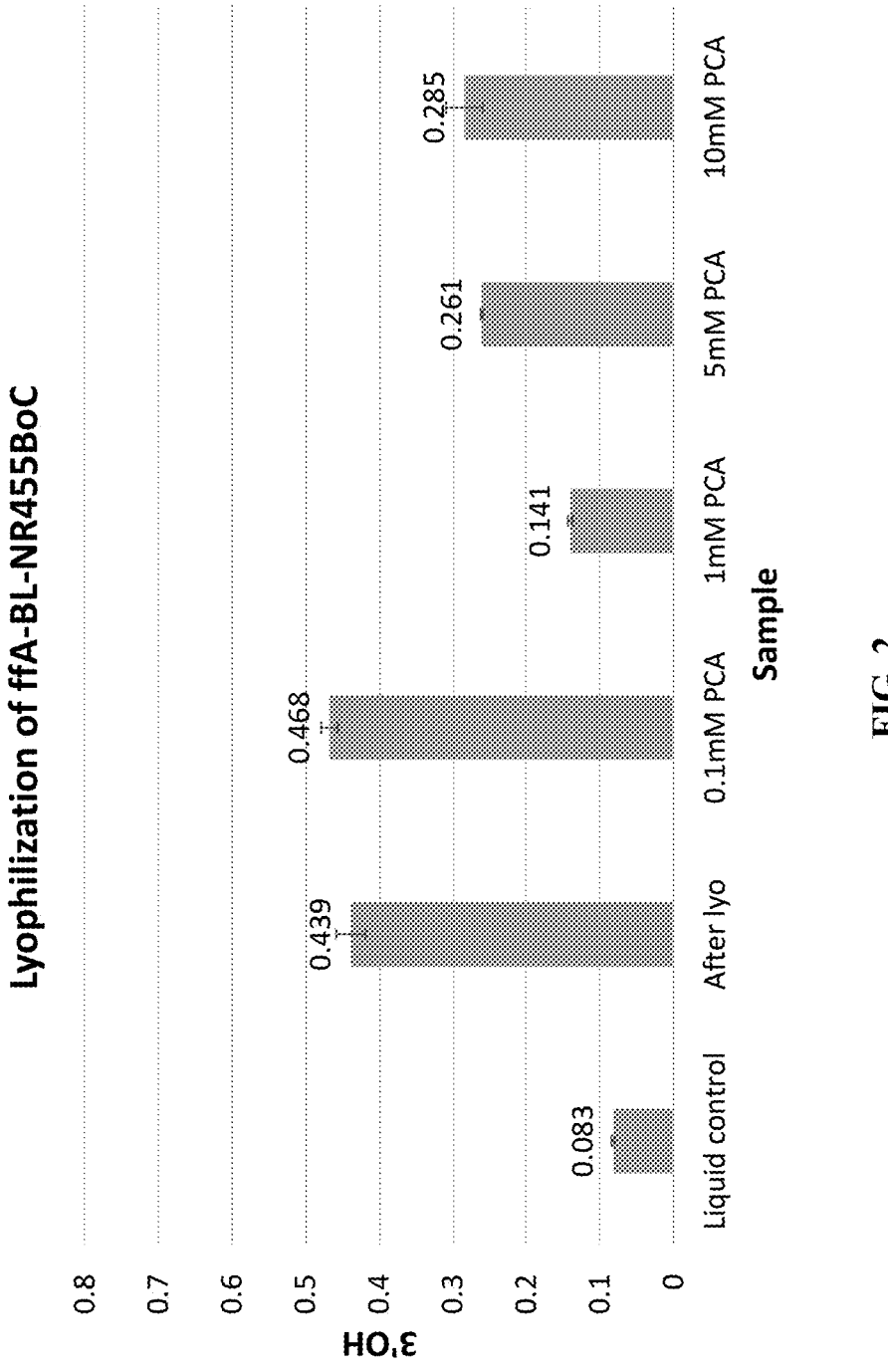
FIG. 2 shows lyophilisation of functionalized nucleotides with PCA radical scavenger at various concentrations.
Figure 3:
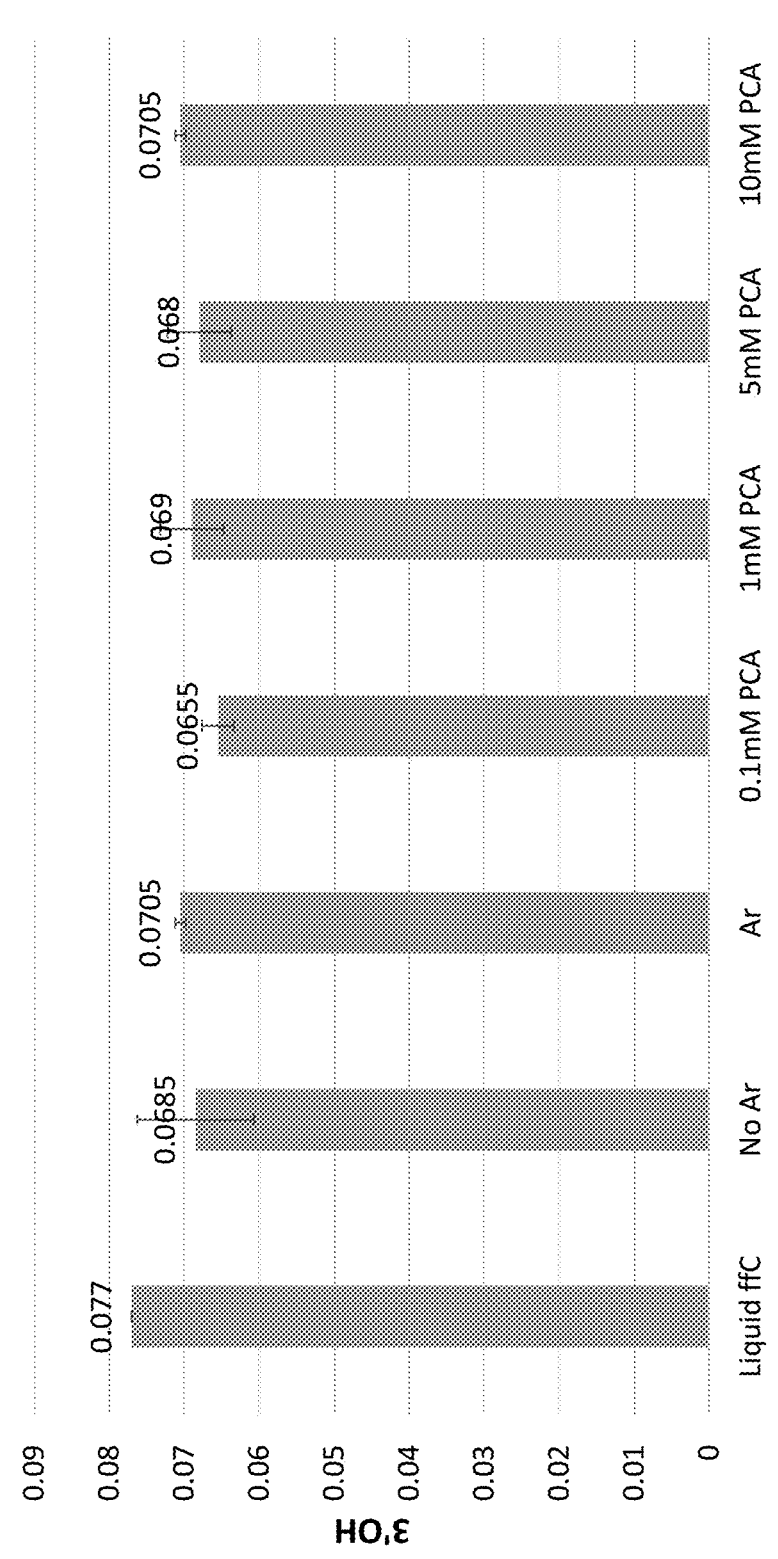
FIG. 3 shows lyophilisation of 10× Blue MiSeg™ cakes with PCA radical scavenger at various concentrations.

Lyophilisation of blue ffNs with radical scavengers lowered 3'OH formation. It was observed that lyophilisation of blue ffNs can cause huge increase in 3'OH formed. The amount of 3'OH formed can be reduced with the addition of radical scavengers such as gallic acid (GA), hydroxyethyl-gallate (HEG), protocatechuic acid (PCA) or catechin in single blue ffN as well as mixture of ffNs (FIGS. 1-3). Addition of radical scavengers brought down the 3'OH close to prelyo control. These radical scavengers are effective because the lyophilisation process itself can cause the formation of radical species, and these radicals can cause deblocking, leading to increase in 3'OH.

Figure 4:
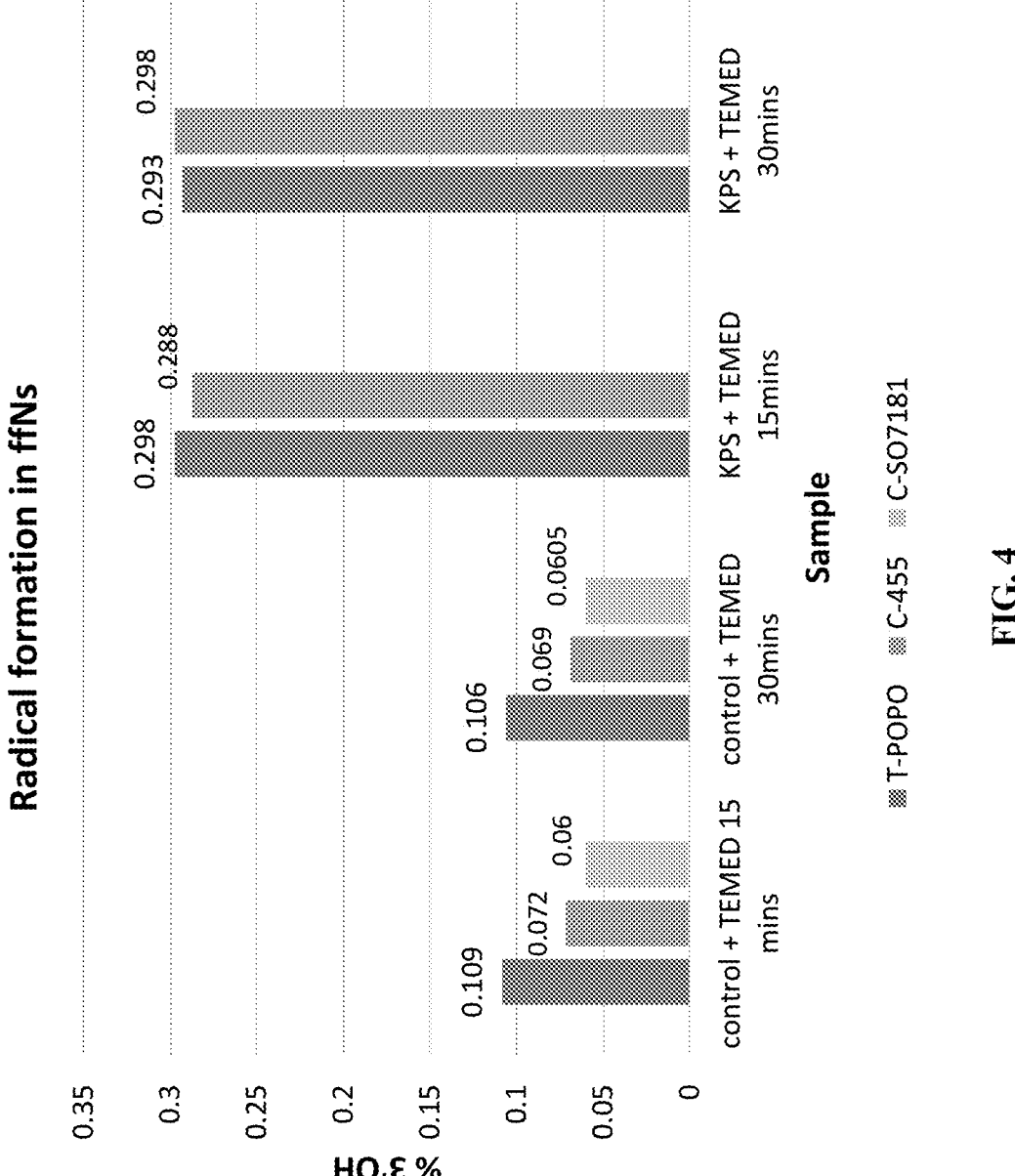
FIG. 4 shows that KPS-TEMED reaction indicated radicals cause deblocking.
Figure 5:
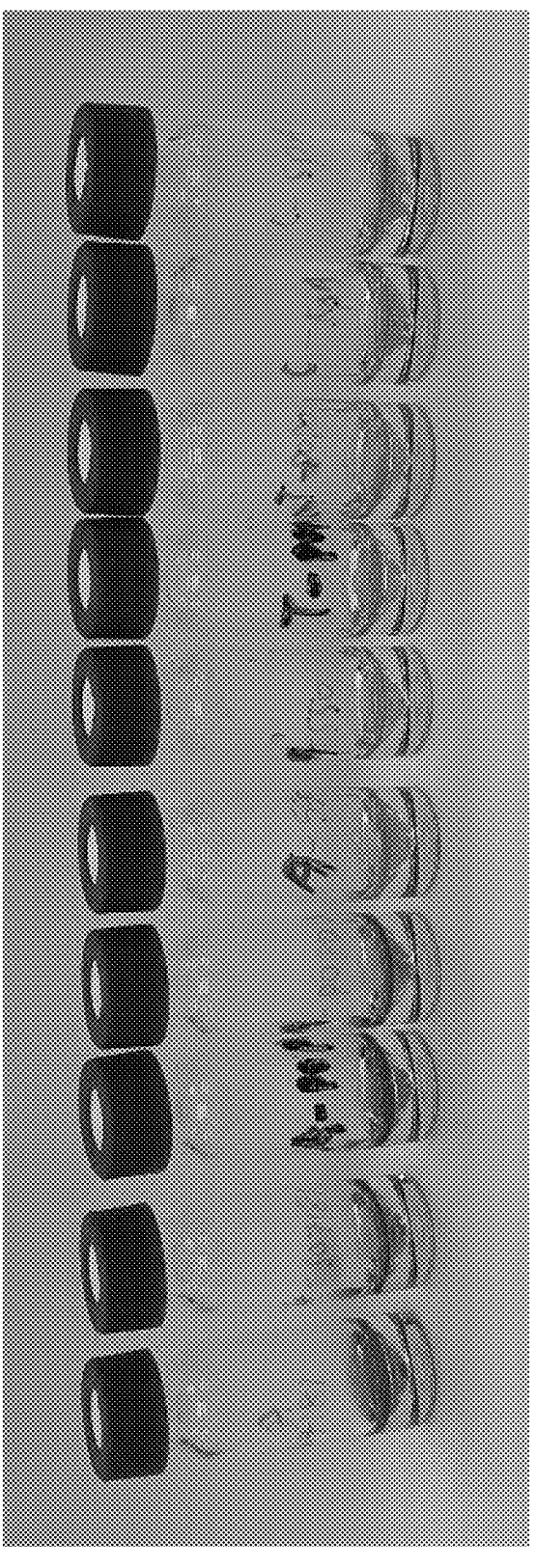
FIG. 5 shows that KPS-TEMED reaction caused intensity drop in some dyes in functionalized nucleotides. Left side shows the control and right side shows after addition of KPS-TEMED.

Radicals cause deblocking in ffNs. It was confirmed that radicals can cause deblocking through the addition of radical initiator such as potassium persulfate (KPS) and Tetramethylethylenediamine (TEMED) (FIG. 4). In the experiment, different blue, green and red dyes were tested as well as in NextSeq™/MiniSeq™ and it was found that there is increase in 3'OH upon reaction with radicals generated from KPS. There is also decrease in intensity in some dyes in which the 3'OH can't be measured due to disappearance of the absorbance peak (FIG. 5).

Figure 6:
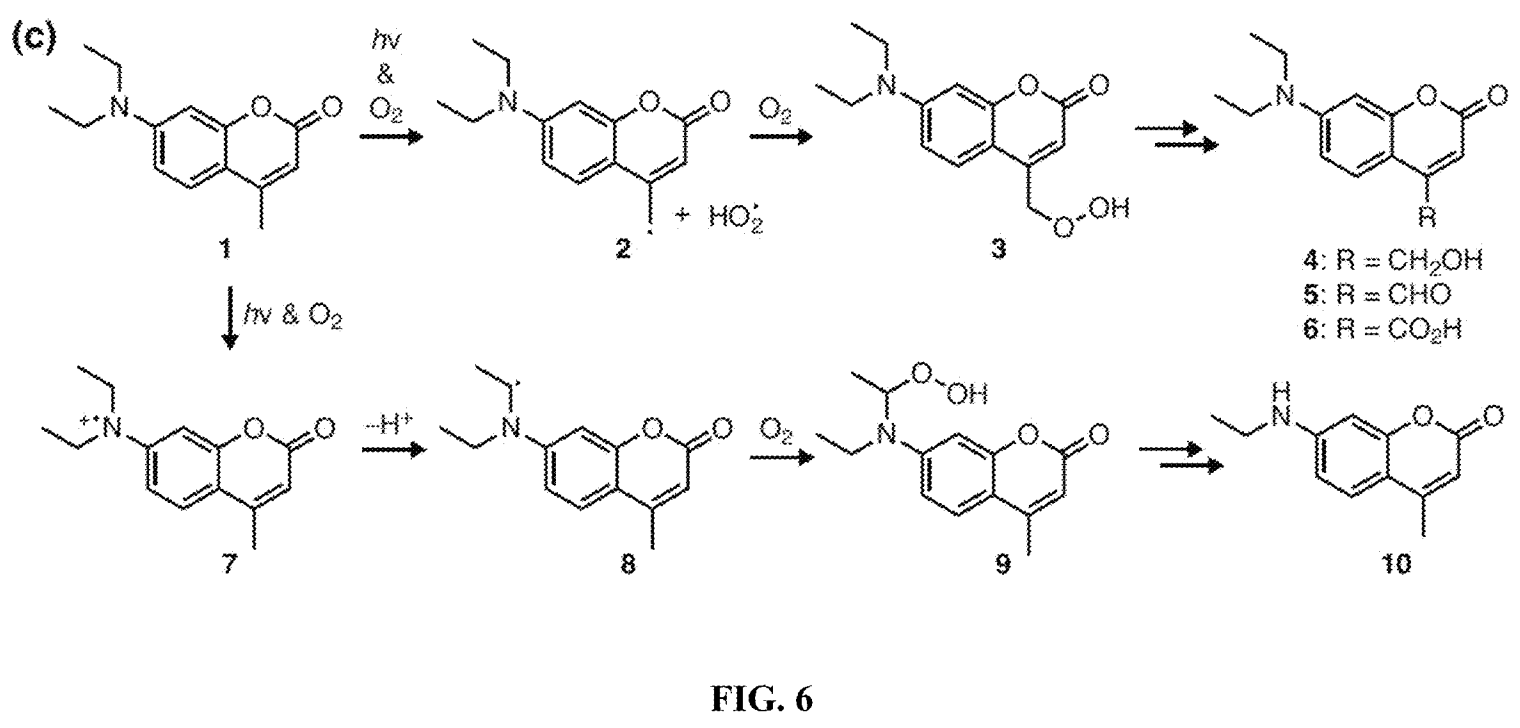
Figure 7:
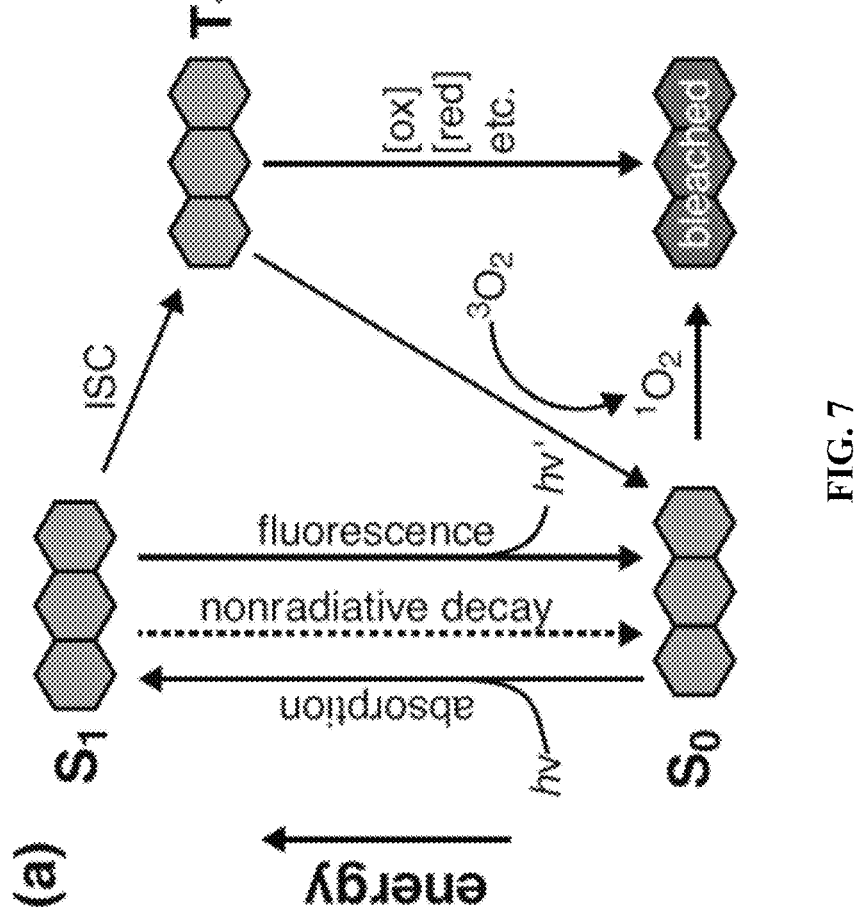
FIG. 7 shows the role of light and oxygen in photobleaching effect.

Mechanism of formation of radicals in blue ffN during lyophilisation. FIG. 6 shows the possible sites of formation of radicals within the coumarin dye. These radicals are generated by the action of heat and/or light together with oxygen. During the lyophilisation process, these blue ffNs with coumarin containing dye are susceptible to any presence of light. Lyophilisation itself also concentrates dissolved oxygen as the compound dries due to reduced water content, therefore contributing to the formation of radicals. FIG. 7 shows the role of light and oxygen for a molecule at excited S1 singlet state crossing over to excited T1 triplet state and reacting with molecular oxygen in a photobleaching process.

Figure 8:
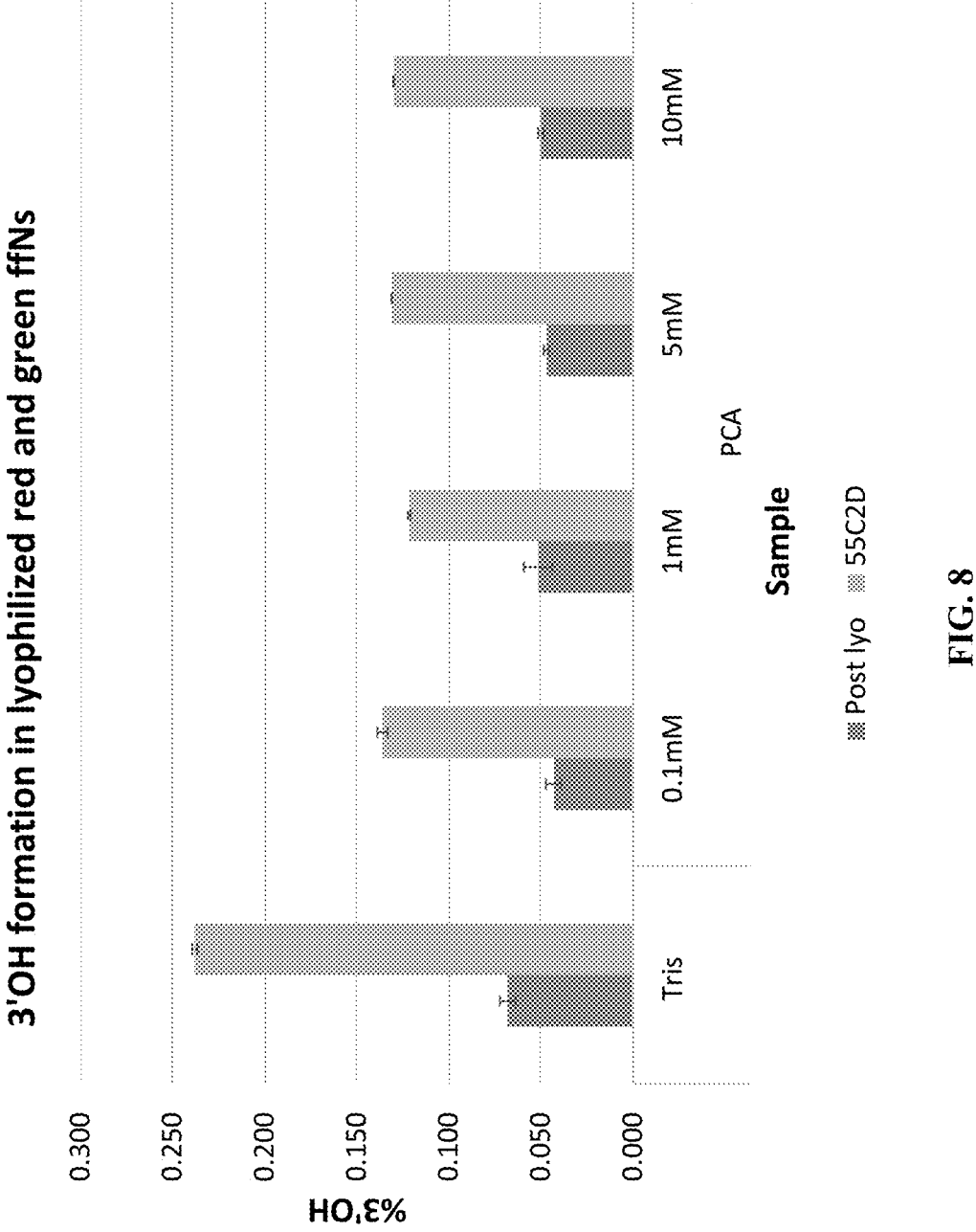
FIG. 8 shows lyophilisation of red and green ffNs in MiniSeg™ with radical scavenger.
Figure 9:
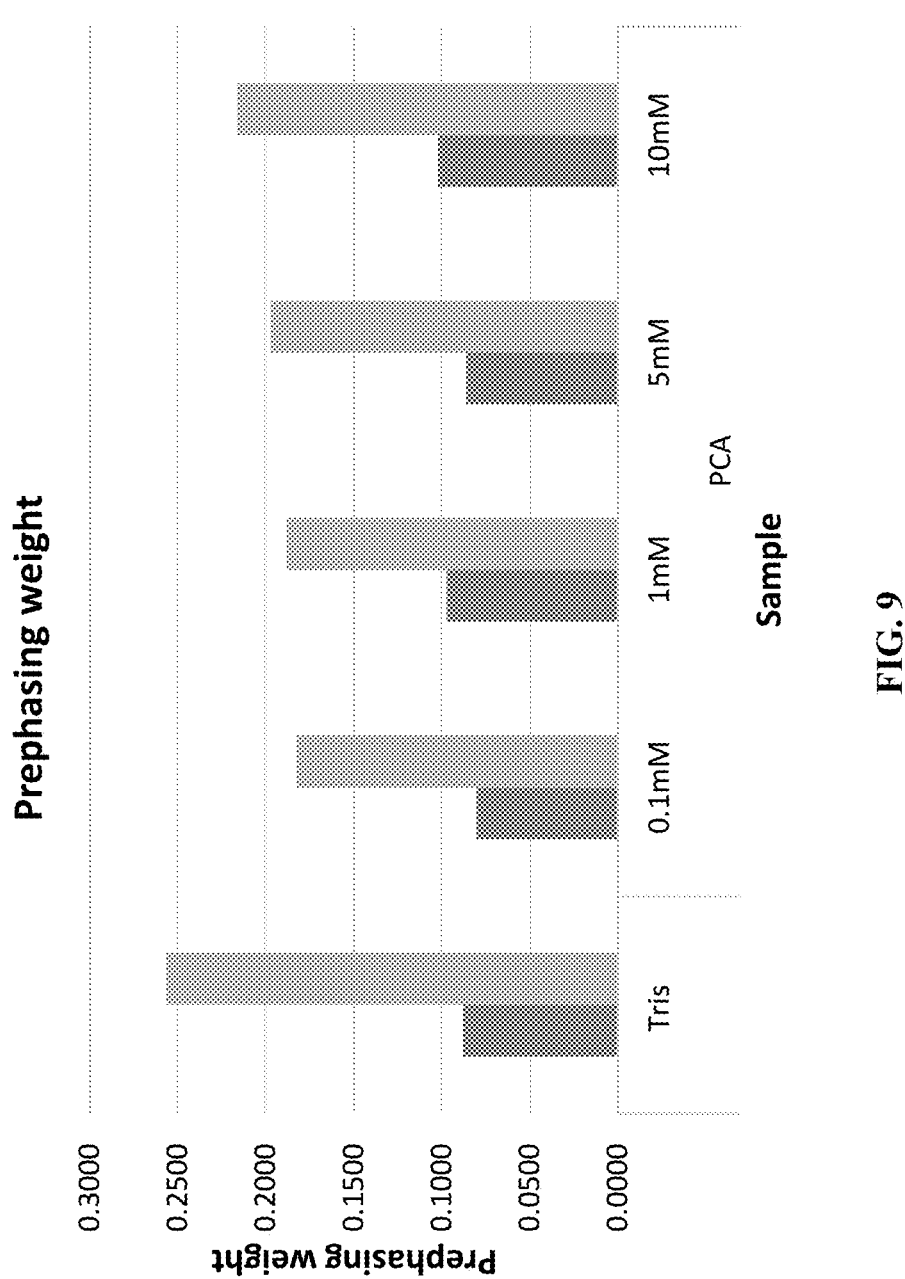
FIG. 9 shows that the addition of radical scavengers lowers prephasing.

Lyophilisation of red and green ffNs with radical scavengers. Addition of radical scavengers were also explored during lyophilisation of red and green ffNs in existing MiniSeq™ NextSeq™ cartridges. Radical scavengers such as PCA also reduced 3'OH formation (FIG. 8), as well as reduce % prephasing during sequencing (FIG. 9).

Figures 10A, 10B:
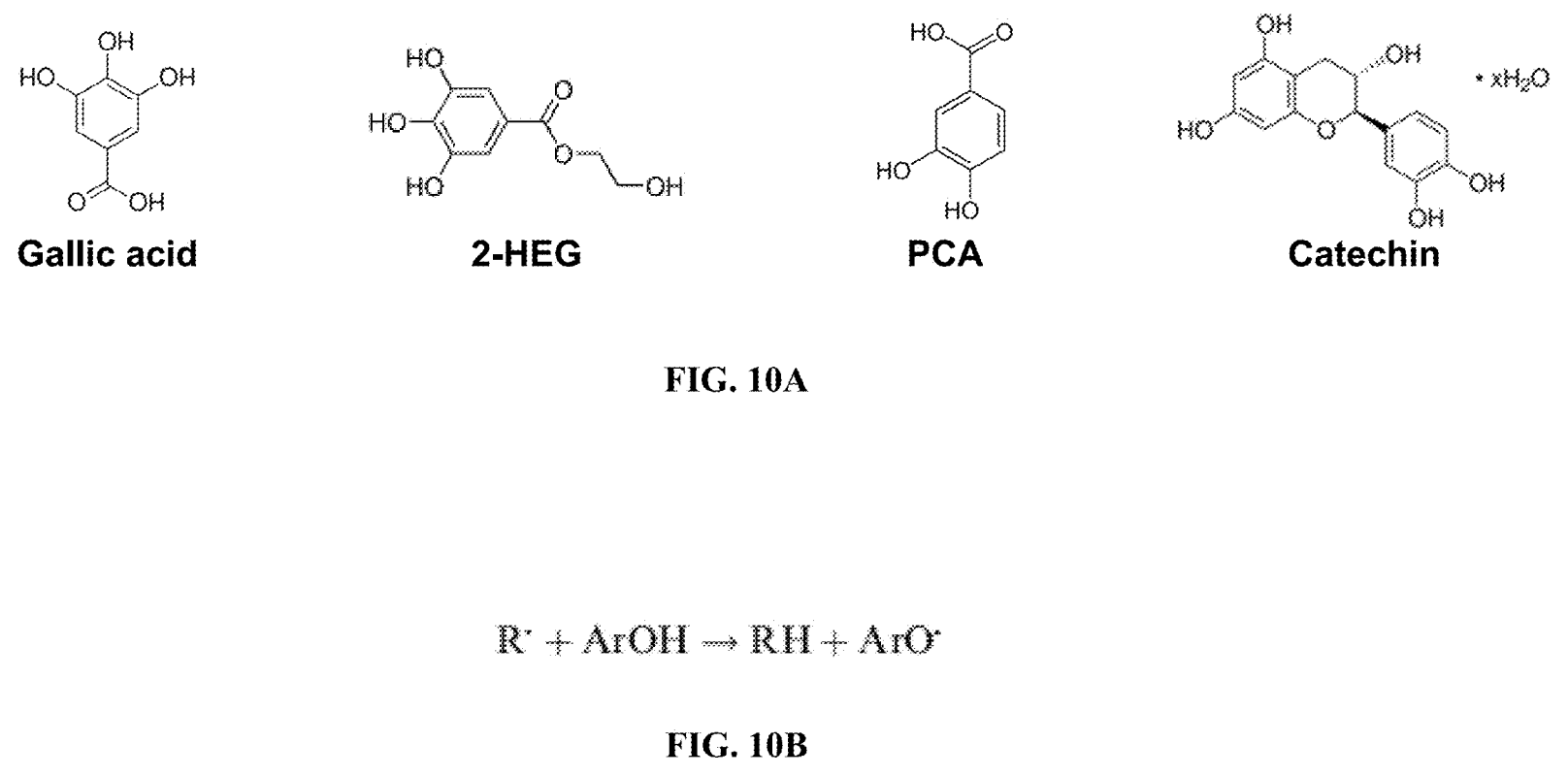

Mechanism of radical scavengers. Radical scavengers are substances that act as antioxidants, thereby terminating or inhibiting the formation of radicals. The most common type of radical scavengers are the phenolic type (FIG. 10A), in which they act as good hydrogen donors due to the presence of an OH group. The radical removes the hydrogen atom from the phenolic antioxidant that itself becomes a radical (FIG. 10B).

Example 2—Stabilized SBS Reagents for Sequencing Applications—Lyophilisation of Incorporation Mix (ICM)

Figure 11:
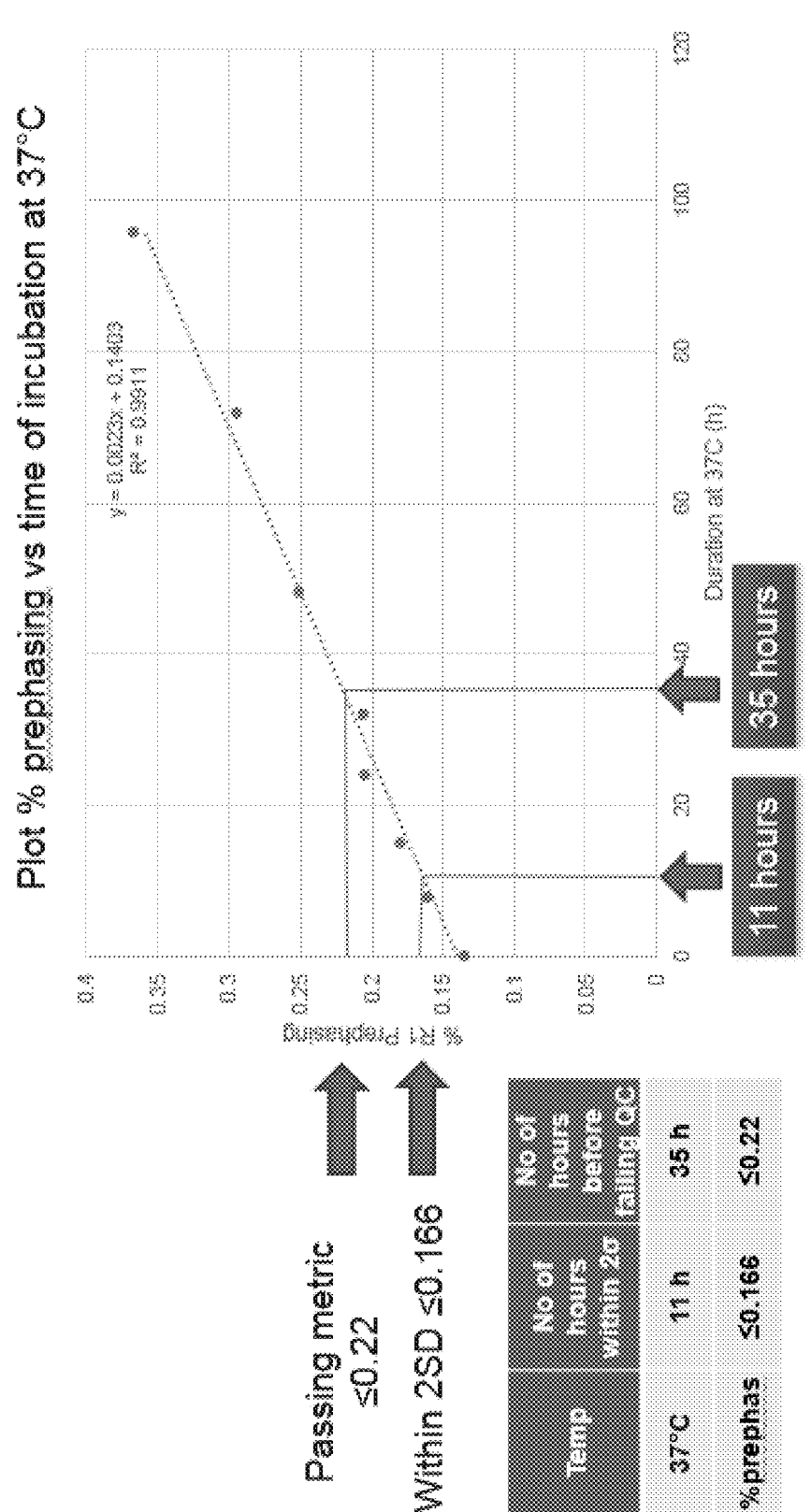
FIG. 11 shows stability of current incorporation mix (ICM) at 37° C.

The stability of the current incorporation mix was tested at 37° C. Incorporation mix was heated at 37° C. for various durations, then sequencing was performed. The % prephasing metric was found to be most sensitive metric to heat stress. % Prephasing increased with increasing duration of heat stress at 37° C. It only stays within 2 standard deviations of the mean (mean value was derived from Final Instrument Test data which aggregates the data from more than 300 instruments and sequencing runs) for 11 hours. % Prephasing, as well as Q30 fails the QC metrics after 35 h of heat stress at 37° C., as shown in FIG. 11.

In order to realize ambient shipping, the reagents will need to be stable for at least 4 days at 37° C., following the ISTA 7D shipping standards. However, internal shipping data has shown that 13% of packages take more than 7 days to arrive. Thus, to realize ambient shipping, the reagents will need at least 14 days of stability at 37° C. To achieve this, it is sought to stabilize incorporation mix via freeze drying or lyophilisation.

Current incorporation mix formulation contains 10% glycerol, which prevents the lyophilisation of ICM. Here, several excipient reformulations are described using a combination of two non-reducing sugars that produces a stable lyophilised cake and remains fully functional upon re-solubilization.

Besides the addition of suitable excipients, the formulation includes increasing the amount of glycerol-free polymerase to account for the decrease in polymerase activity after lyophilisation.

Excipient Screen for full Incorporation Mix (ICM). First, an excipient screen was performed for suitable cryoprotectants of incorporation mix (ICM). Sucrose and trehalose are non-reducing sugars which perform the best among more than 20 excipients tested. A sucrose and trehalose titration was performed for incorporation mix to determine the optimal ratio of sugars required for lyophilisation.

Various sucrose and trehalose excipient ratios were formulated and aged at 37° C. for 4 days and 14 days. Several sucrose-trehalose excipient ratios were able to maintain the structural rigidity of the lyophilised ICM. To identify if an excipient was successful in maintain the mechanical rigidity of lyophilised ICM, the first criteria is that the lyophilised cake should remain mechanically stable and not collapse after heat stress.

Figure 12A:
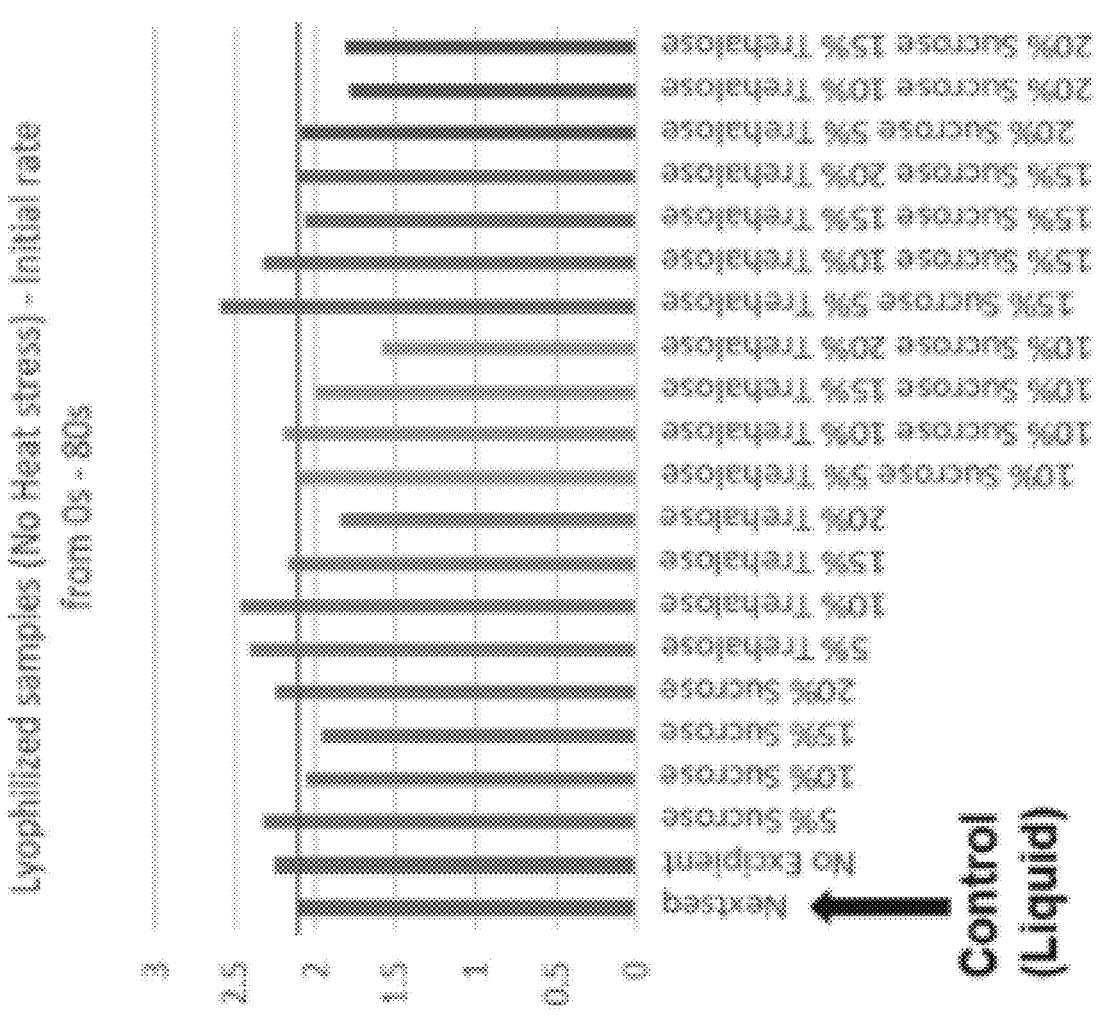
FIGS. 12A-12C shows polymerase activity of lyophilised ICM that underwent two different aging studies at 37° C.
Figure 12B:
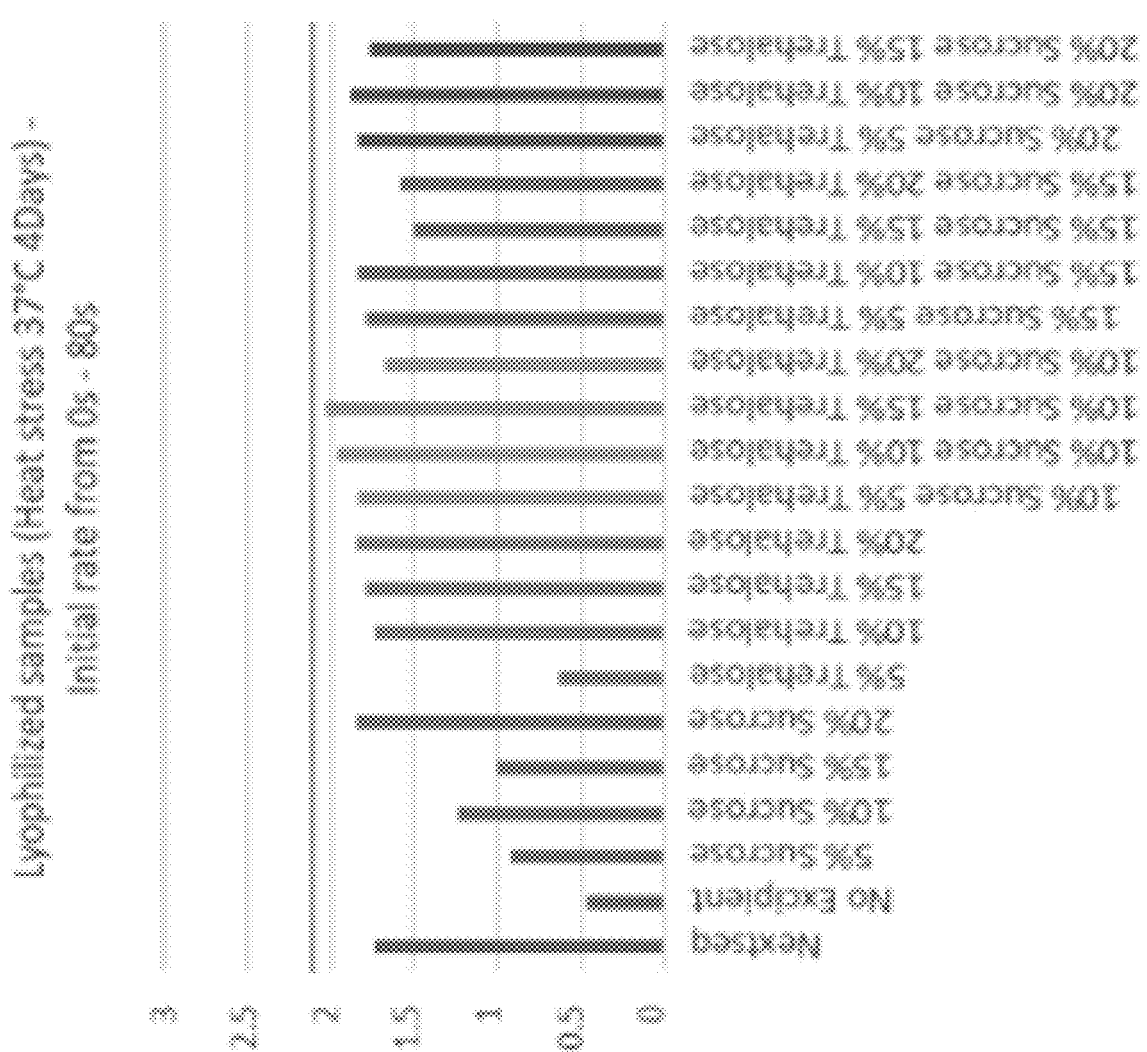
Figure 12C:
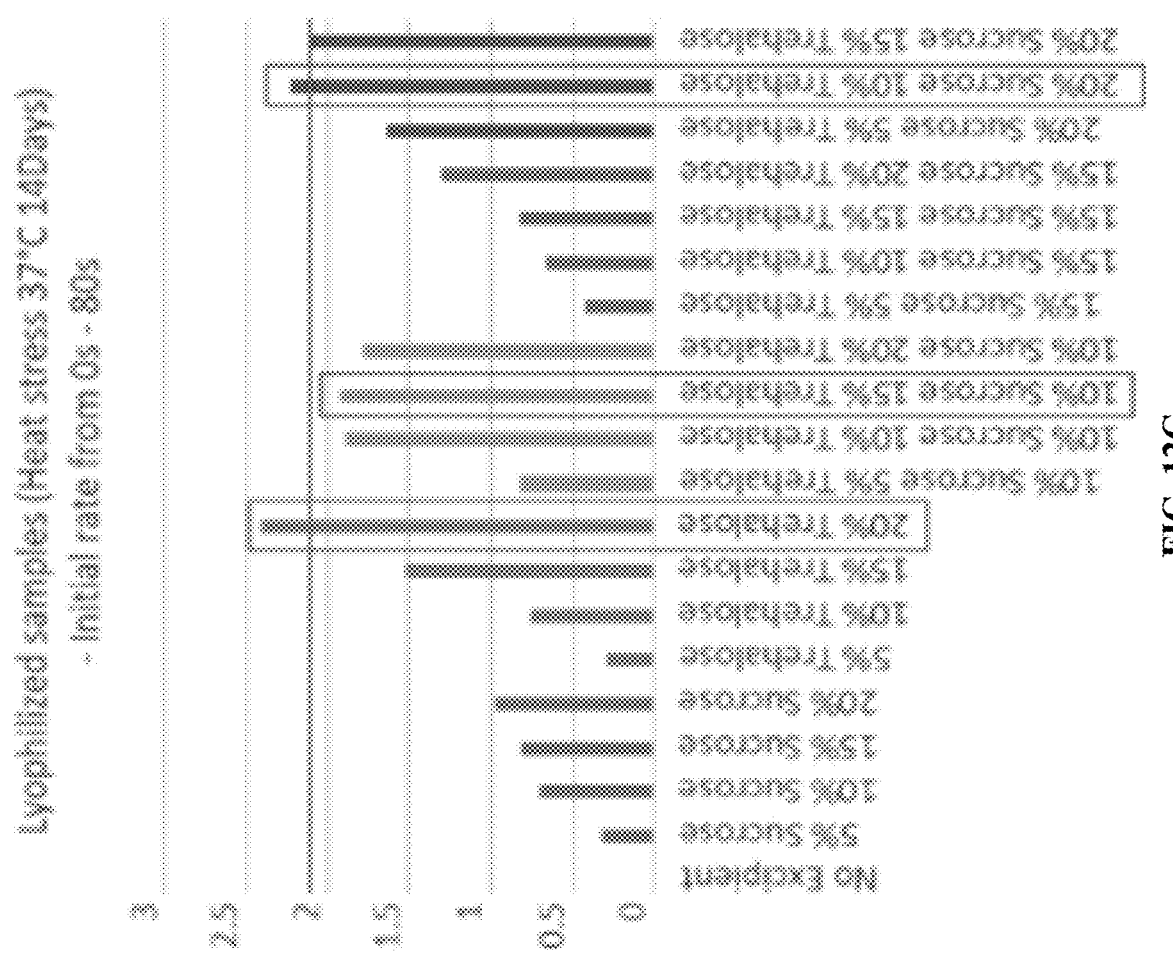
Figure 13A:
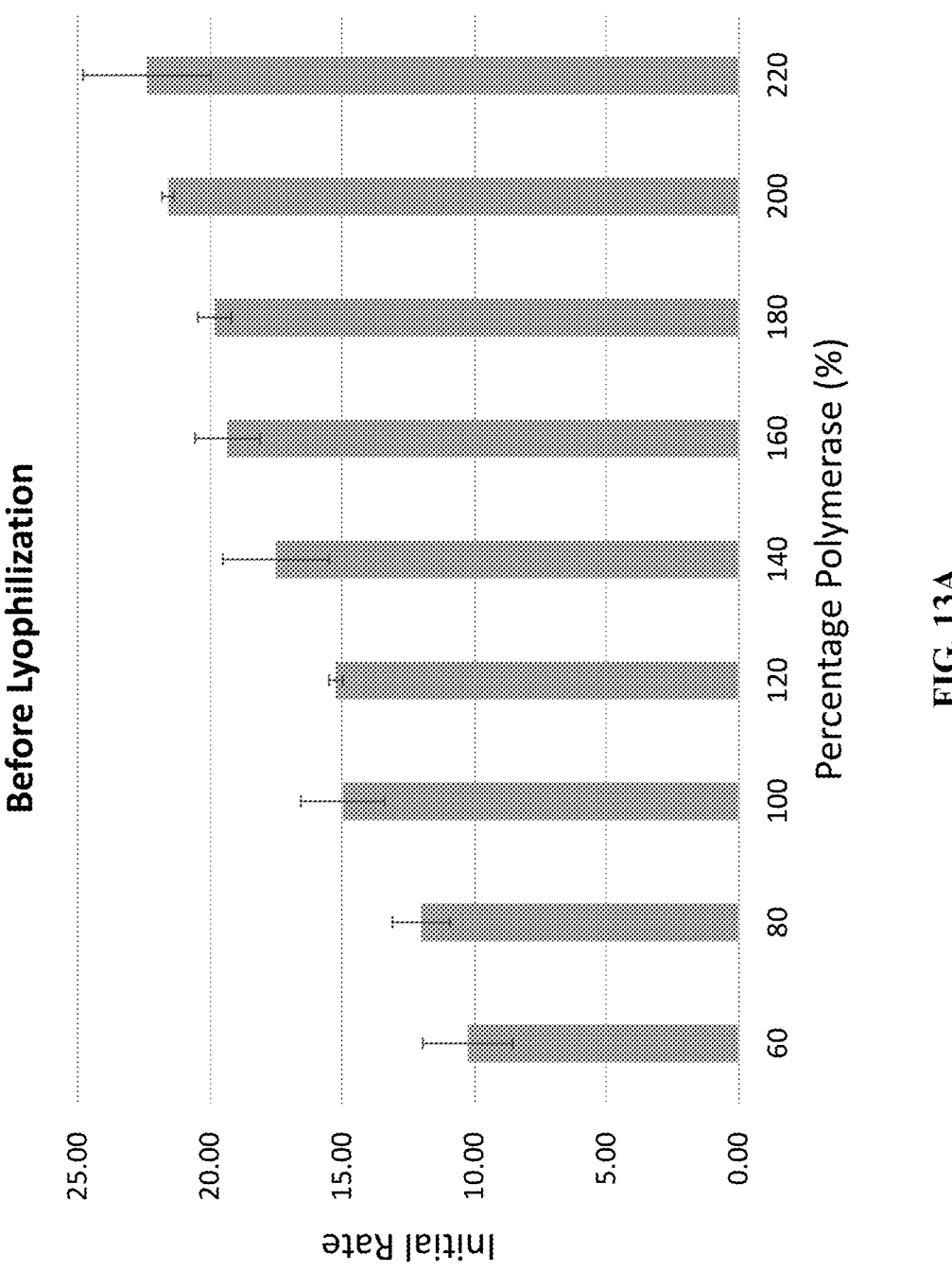
FIGS. 13A-13B shows polymerase activity before and after lyophilisation.
Figure 13B:
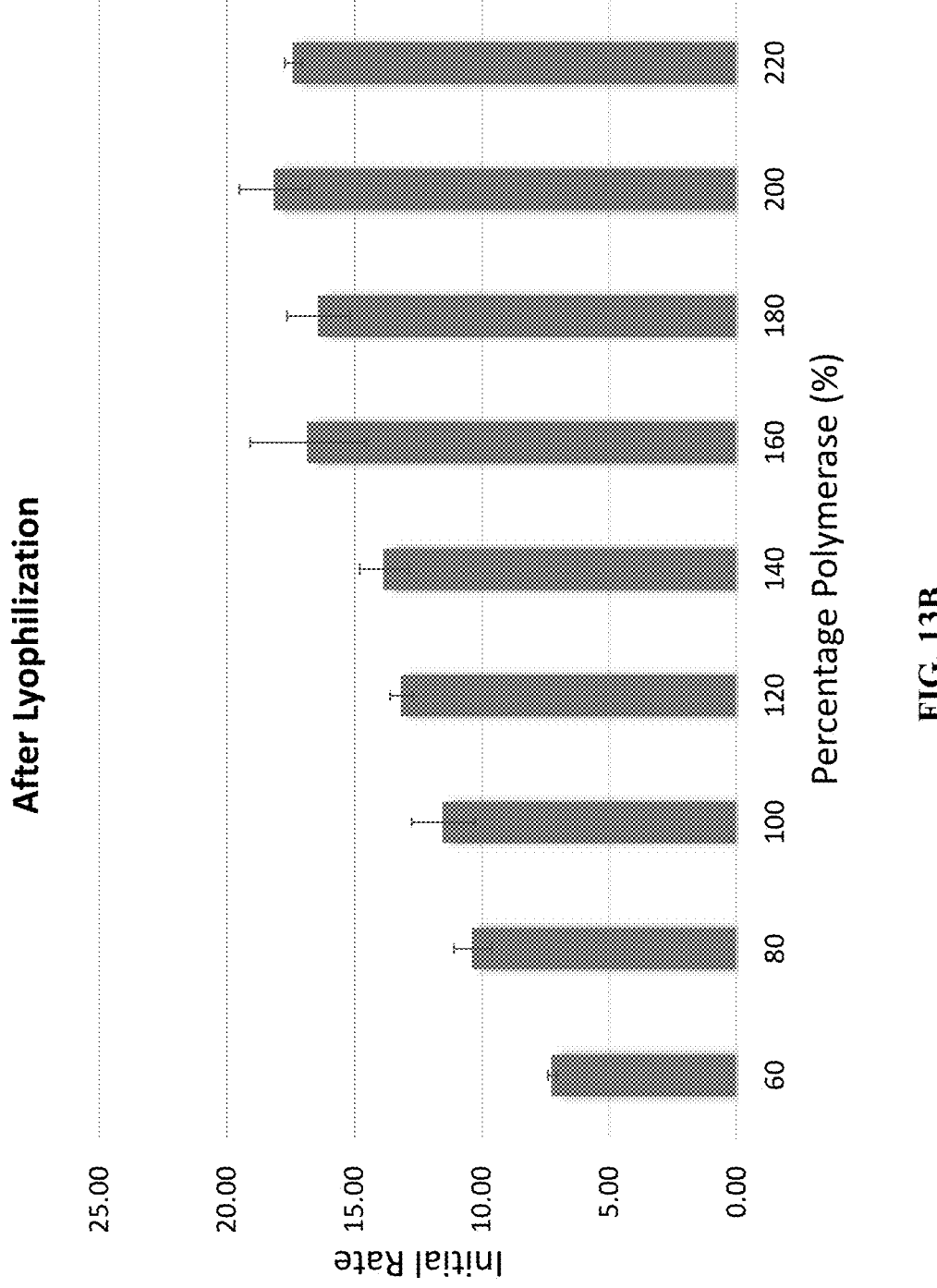

To assess the activity of polymerase after lyophilisation and heat stress, fluorescence resonance energy transfer (FRET) assay was performed on the lyophilised samples. From FIGS. 12A-12C, it can be seen that 20% trehalose, 10% sucrose+15% trehalose and 20% sucrose+10% trehalose are the best excipients in their respective categories, that exhibited the highest polymerase activity after 14 days of heat stress at 37° C. FIGS. 13A-13B shows polymerase activity before and after lyophilisation.

It can be seen from FIG. 11 that a minimum of 150% polymerase is required for the polymerase activity of lyophilised ICM to match with 100% polymerase before lyophilisation.

10% sucrose and 15% trehalose was successfully lyophilised in a 2× concentration of ICM. The lyophilised ICM was reconstituted with ethanolamine buffer and sequenced on a Miniseq™.

Lyophilisation of ffN solution. The possibility of lyophilising only the unstable components of incorporation mix, instead of the full incorporation mix was also explored. In this section, only the fully functional nucleotides were lyophilised.

Another excipient screen had to be performed for the ffNs, since the buffer conditions are different from the full incorporation mix. A sucrose and trehalose titration was carried out for ffNs only to determine the optimal ratio of sugars required for lyophilisation of ffN.

Various sucrose and trehalose excipient ratios were formulated and aged at 37° C. for 3 days. Selected excipient formulations were lyophilised in 5 mL glass vials. The mechanical rigidity of all excipient formulation were maintained and all samples were dried (based on visual inspection). These lyophilised cakes maintained its mechanical rigidity even after heat stress and none were collapsed.

Bead lyophilisation of ffN solution. An alternative format of lyophilising ffNs was also attempted, to form lyophilised beads of ffNs. Two ffN only formulations containing 50% trehalose and 20% sucrose were prepared. ffN beads were generated by dispensing drops of ffN only solution into liquid nitrogen. Beads with individual bead volume between 16 μL to 60 μL were generated. The beads generated using a peristaltic pump gave the most consistent beads so far.

ffN and Pol were formulated separately and lyophilised. Formulation with 15% sucrose and 25% trehalose appeared to be wet at the base. A possible hypothesis is due to overloading of the sample. Sequencing was performed.

Example 3—Stabilization of Second Linearization Mix (BLM2)

Current BLM 2 formulation contains 2.4% glycerol, which prevents the lyophilisation of BLM 2. Here, several excipient reformulations that produce a stable lyophilised cake and remain fully functional upon re-solubilization are described.

Figure 14:
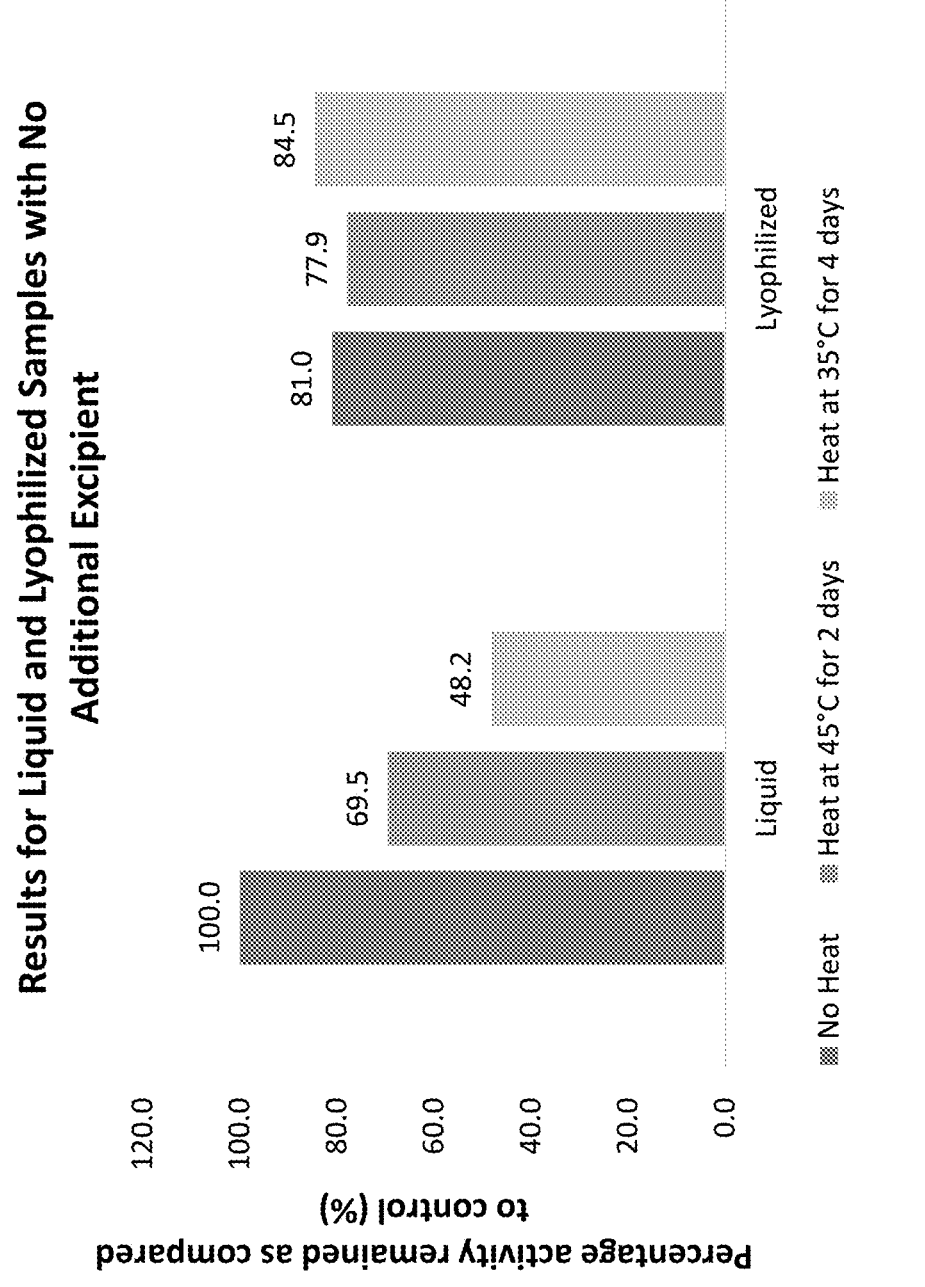
FIG. 14 shows that lyophilisation is necessary to retain activity of BLM2 after heat stress.
Figure 15A:
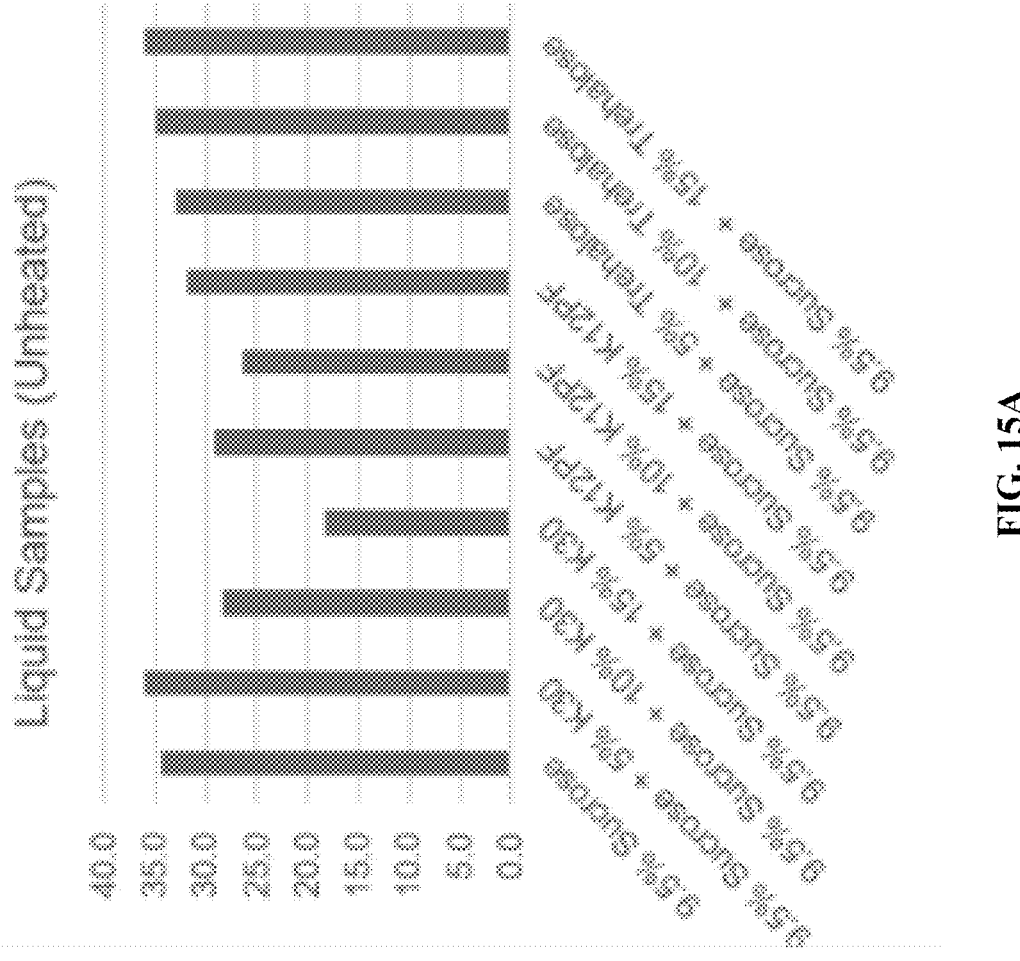
FIGS. 15A-15C shows percentage activity of liquid samples after aging experiment at different temperatures.
Figure 15B:
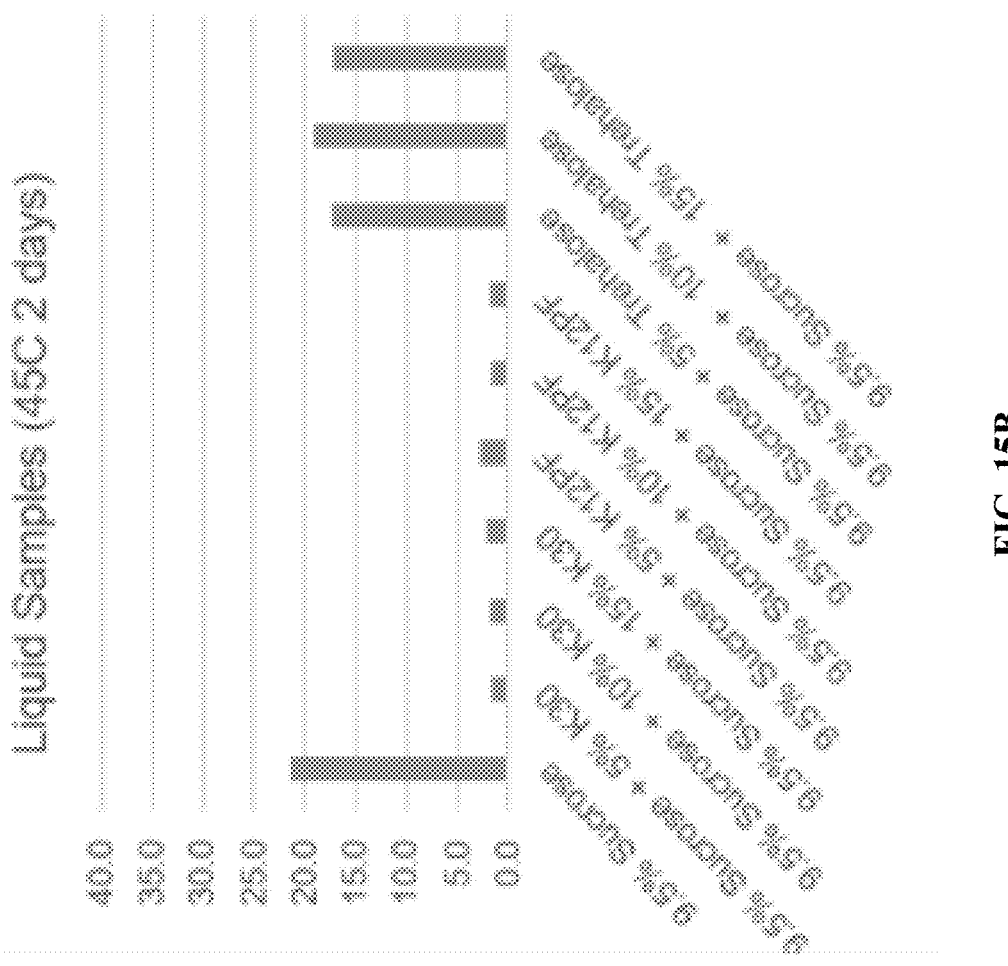
Figure 15C:
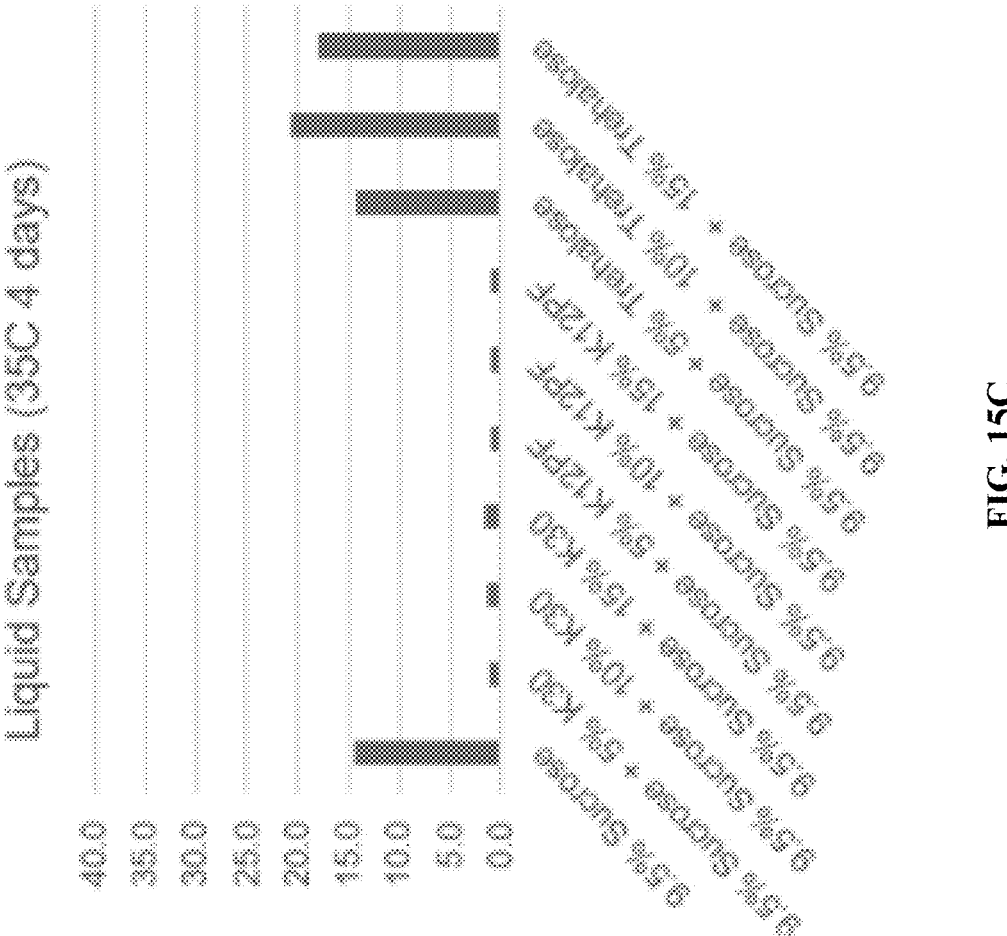
Figure 16A:
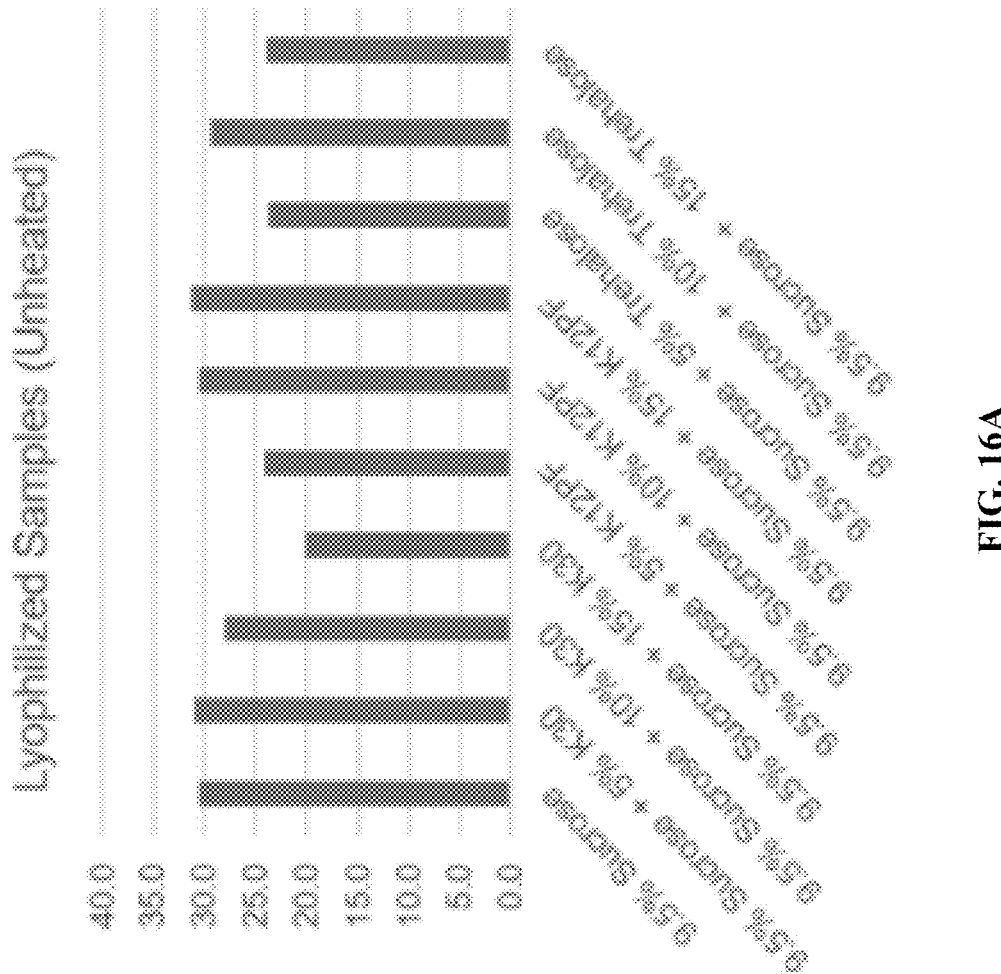
FIGS. 16A-16C shows percentage activity of lyophilised samples after aging experiment at different temperatures.
Figure 16B:
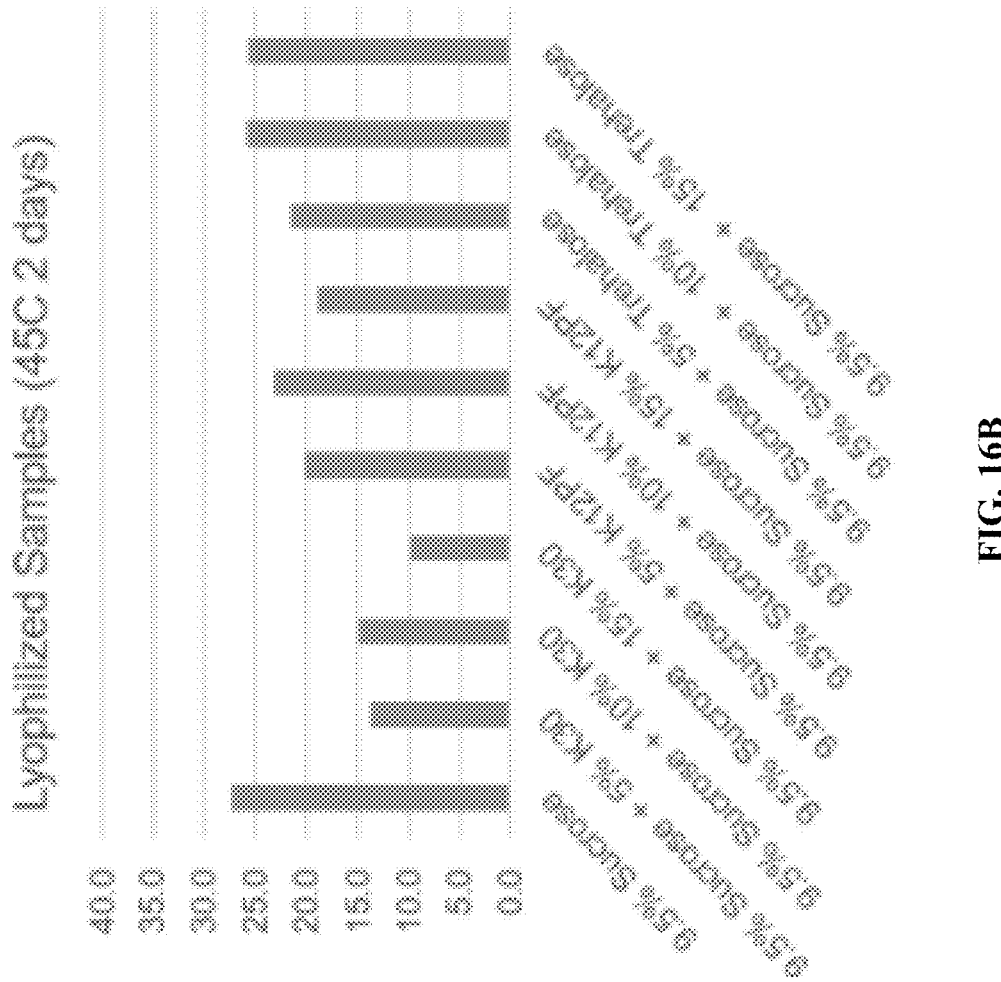
Figure 16C:
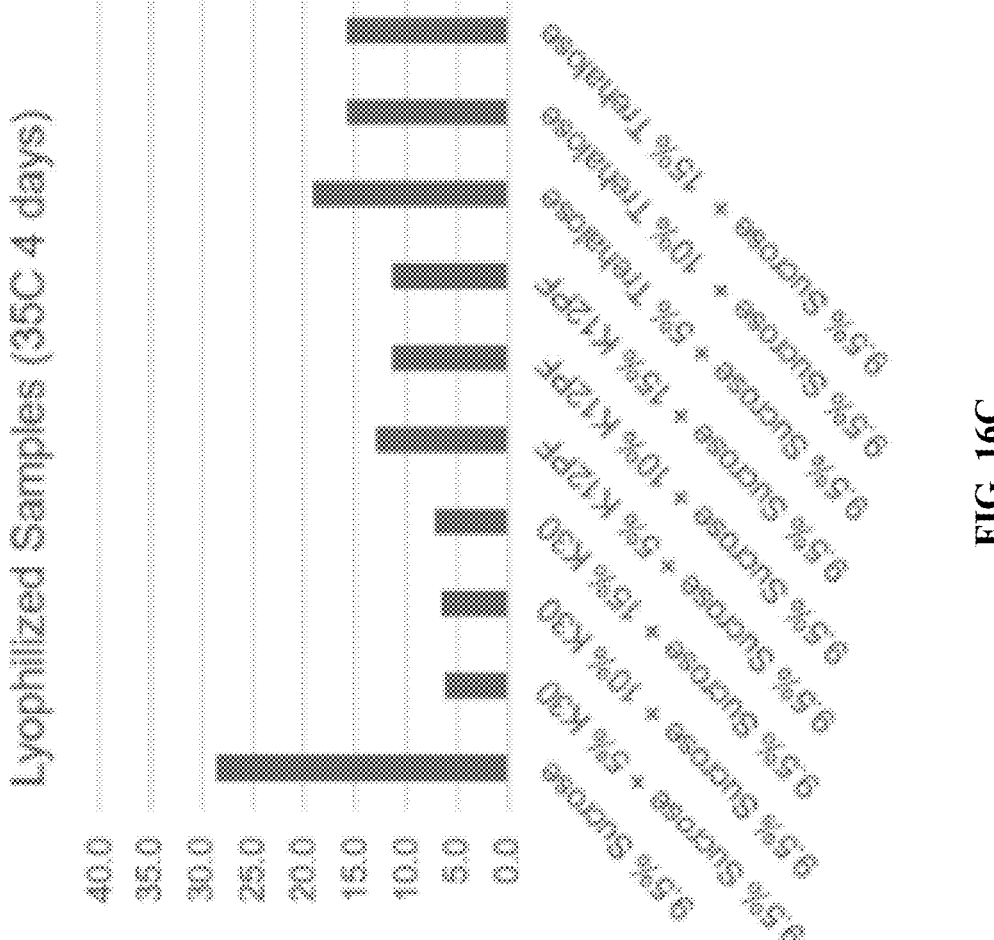

From FIG. 14, it can be seen that after aging BLM 2 for 4 days at 35° C., BLM2 has lost more than half of its activity. However, lyophilisation was able to retain BLM2 activity with only 15.5% lost.

After aging BLM 2 at two different temperatures, the excipients were able to maintain the mechanical rigidity of the sample with exception of 9.5% sucrose, which shows an anticipated shrinkage of cake.

Comparing FIGS. 15A-15C and FIGS. 16A-16C, it can be seen that 9.5% sucrose is the best excipient that retains the maximum activity of BLM 2. 9.5% sucrose+10% trehalose also maintains the mechanical rigidity and exhibits the high activity.

Example 4—Lyophilisation of Resynthesis Mix (BRM)

T4 Polynucleotide Kinase (T4 PNK) is a homo tetramer enzyme that has two distinctive functions in DNA and RNA repair: the 5'-kinase and 3'-phosphatase activities.

T4 PNK utilizes both functions in two main uses in workflows. First, during ILMN library prep, T4PNK phosphorylates the 5' ends of the DNA fragments, which have blunt end repaired by polymerase, enabling the DNA piece for ligation. Second, during SBS sequencing, T4PNK removes 3' phosphoryl group from the surface-bound P5 primers, allowing the subsequent strand resynthesis.

Currently, BRM solution shows instability at 37° C. within 5 days. Here, a method of stabilizing this enzyme both in liquid form as well as freeze dried form is described. The content of the solution in which this enzyme resides include 10% glycerol, imidazole buffer, sucrose, magnesium chloride and 2-mercaptoethanol, constituting the Resynthesis Mix (BRM).

This method of stabilization will be an important milestone towards achieving the goal of ambient shipping and storage of sequencing cartridges.

As BRM formulations with 10% glycerol cannot be lyophilised to dryness, BRM was formulated without glycerol. Excipients such as trehalose, Kollidon 12PF, and Kollidon 30 were also added in 5 to 15 wt/v %. BRM was lyophilised in the same way as the Incorporation Mix. Various tubes formats of BRM was lyophilised successfully. Trehalose as an excipient was added.

BRM formed a nice cake after lyophilisation with and without excipient. An assay was measured using HPLC to detect any dephosphorylation activity of the enzyme both in liquid as well as freeze dried form. Activity was measured after 5 minutes.

Figure 17:
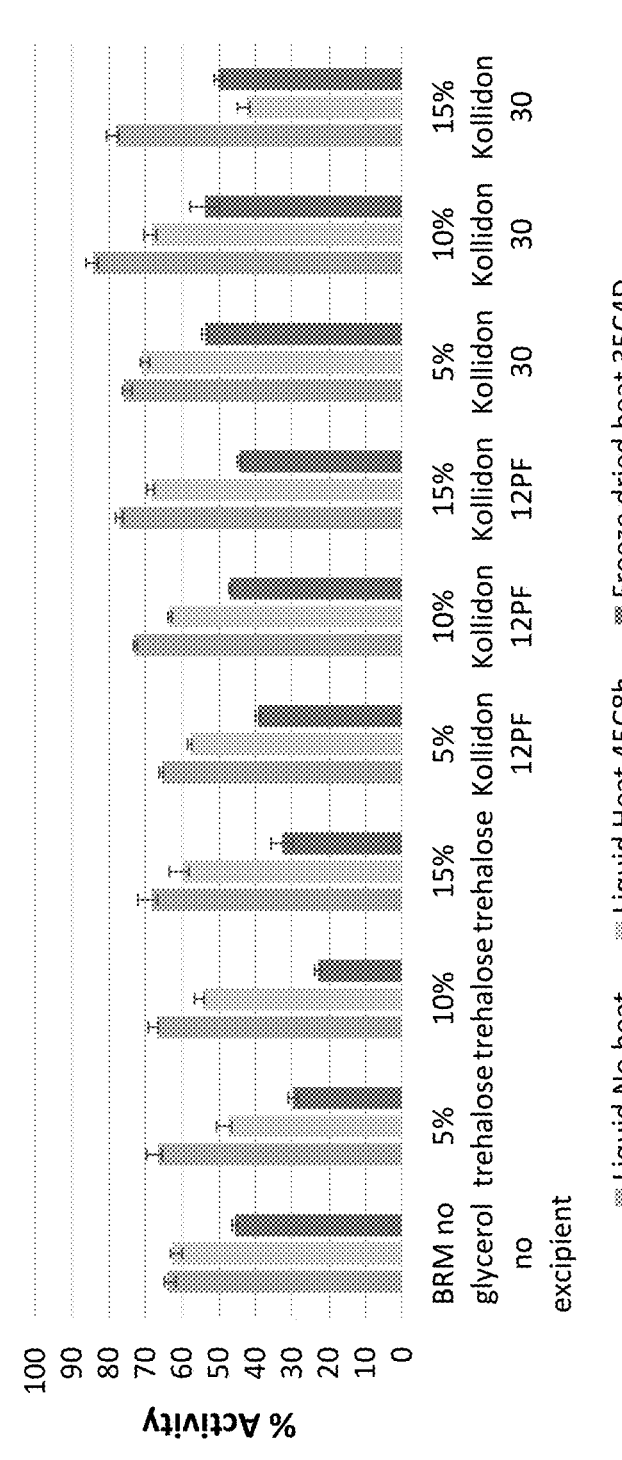
FIG. 17 shows liquid and freeze dried BRM pre- and post-heat stress.

FIG. 17 shows that addition of trehalose, Kollidon 12PF and Kollidon 30 helped to stabilize BRM in liquid form after heat stress. The amount of stability conferred depends on the amount of excipient used. After heat stress at 45° C. for 8 hours, 15% Kollidon 12PF, 5% and 10% Kollidon 30 were able to maintain the activity of BRM.

Freeze drying of BRM resulted in about 20% activity loss, however addition of excipient such as 10% Kollidon 12PF and Kollidon 30 were able to maintain or improve the activity after heat stress.

Example 5—Lyophilisation of Other Reagents

The lyophilisation methods also include drying on a manifold lyophiliser at −51° C. Reagents that were lyophilised successfully include Scan Mix (SRM), Cleavage Mix (CMS), Amplification Mix (BMS), Sequencing primers (BP10 and BP11) and Indexing primers (BP14) that have low glycerol content of less than 1%. All lyophilised materials were sequenced on NextSeq™ instrument and Q30 score was above passing metrics of 83%.

Example 6—Lyophilised Single Tube ExAmp Mix Using Water for Resuspension

Current commercialized lyophilised RPA mixes from TwistDx, are formulated in a two tube format, with enzymes/substrates in one tube, and PEG+Magnesium separated in a second tube.

The present formulation, in contrast, includes the following non-obvious findings: (1) lyophilisation of a PEG-free ExAmp mixture, and (2) lyophilisation of an ExAmp mixture with the inclusion of Mg in the same solution in which several Mg-dependent enzymes are present (e.g., recombinase, polymerase).

Figure 18:
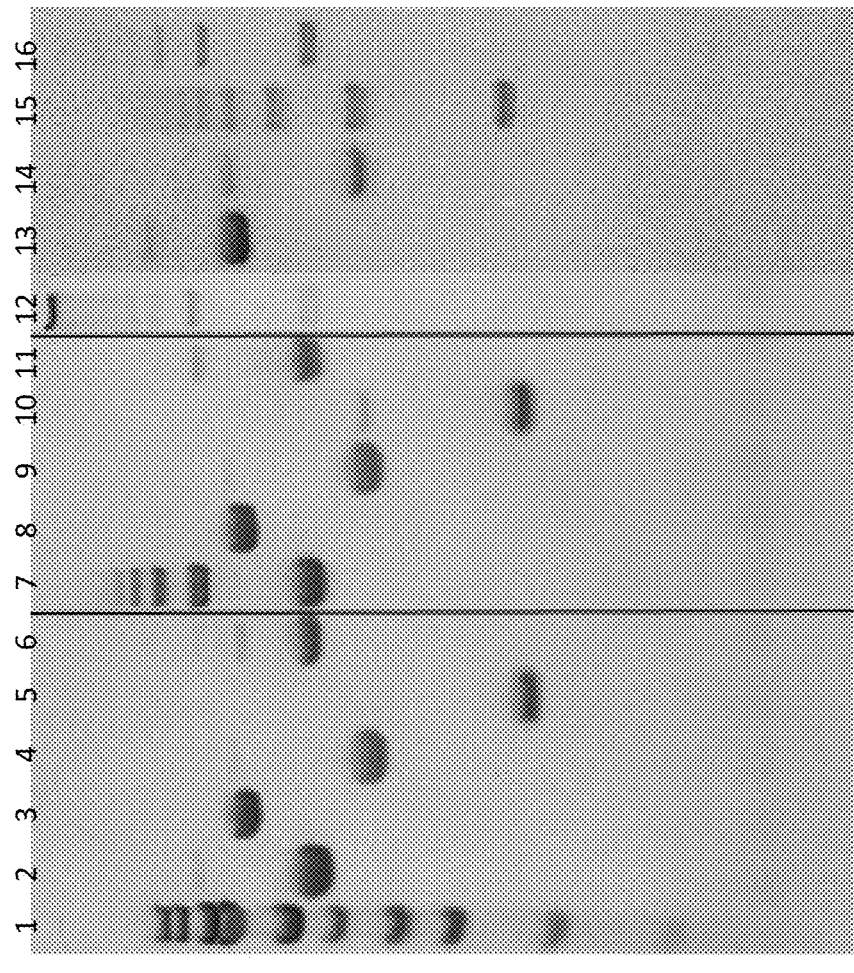
FIG. 18 shows individual ExAmp protein incubated with and without Mg at elevated temperatures.

In solution, Mg accelerates the structural changes that lead to the assembly/oligomerization of several ExAmp components, such as gp32, UvsY, recombinase, or creatine kinase. When DNA is present, this leads to successful DNA strand recombination and subsequent amplification. However, in the absence of DNA, this protein oligomerization leads to instability by way of non-functional protein aggregation over time. Individual ExAmp protein incubated with and without Mg at elevated temperatures are shown in FIG. 18.

All samples were lyophilised in duplicate. After lyophilisation, one replicate set was immediately resuspended in 150 uL water and mixed by pipette to assess activity of the sample after the lyophilisation process. The second replicate set of samples was either stored at 37° C. overnight or up to five days to assess stability of the lyophilised cake at elevated temperature over time.

To assess activity, the resuspended Ras6T sample was used to cluster on a HiseqX™ v2.5 standard flow cell. This entails flowing single stranded DNA (from a TruseqNano™ human library prep) onto the flow cell at elevated temperatures and allowing the flow cell to cool so the DNA can hybridize to complement primers on the flow cell. This is followed by two thirty minute pushes of the resuspended lyophilised Ras6T mix over the flow cell to generate and amplify localized copies, using RCA technology, of the hybridized single stranded DNA (clustering). Post clustering, the flow cell was sequenced on a HiseqX™ instrument using standard SBS sequencing. Activity of the clustering mix was assessed by comparing the cluster intensity of each sample to a non-lyophilised freshly mixed Ras6T control. If the enzymes in the Ras6T formulation are unstable/inactive, there would be no amplification of the clusters which would appear as dim or no signal intensity.

Figure 19A:
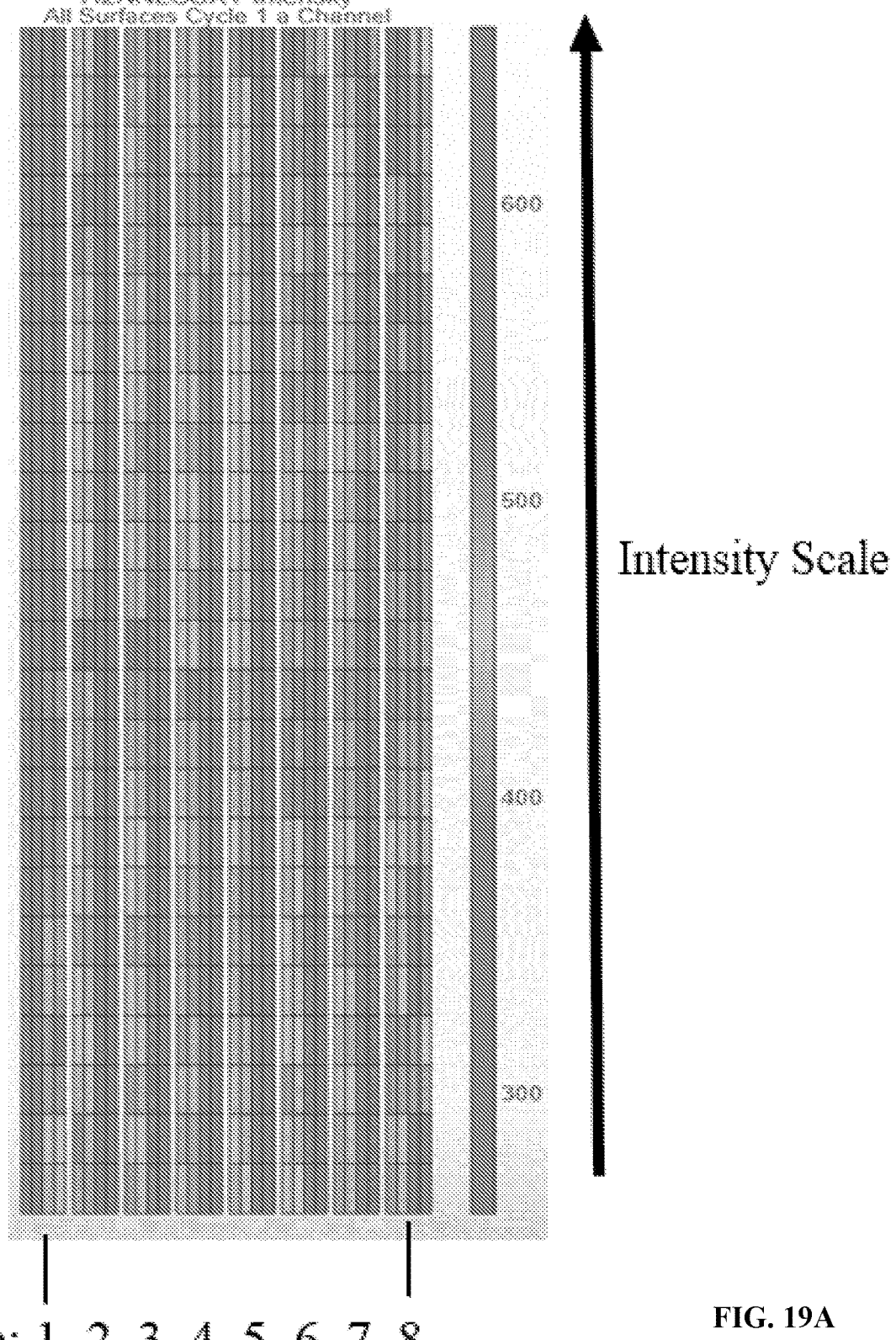
FIGS. 19A-19B show lyophilised PEG free Ras6T clustering activity immediately upon freeze-drying (FIG. 19A) and after incubation of the pellet at 37° C. 16 hours (FIG. 19B). All lyophilised formulations have activity after lyophilisation. However, once the cake has been incubated at 37° C. for 16 hours, the resuspended lyophilised pellets without non-reducing sugars produced very dim clusters (dark blue lanes 2-4). All lanes containing sucrose or trehalose in the lyophilisation mix retains activity (yellow to orange).
Figure 19B:
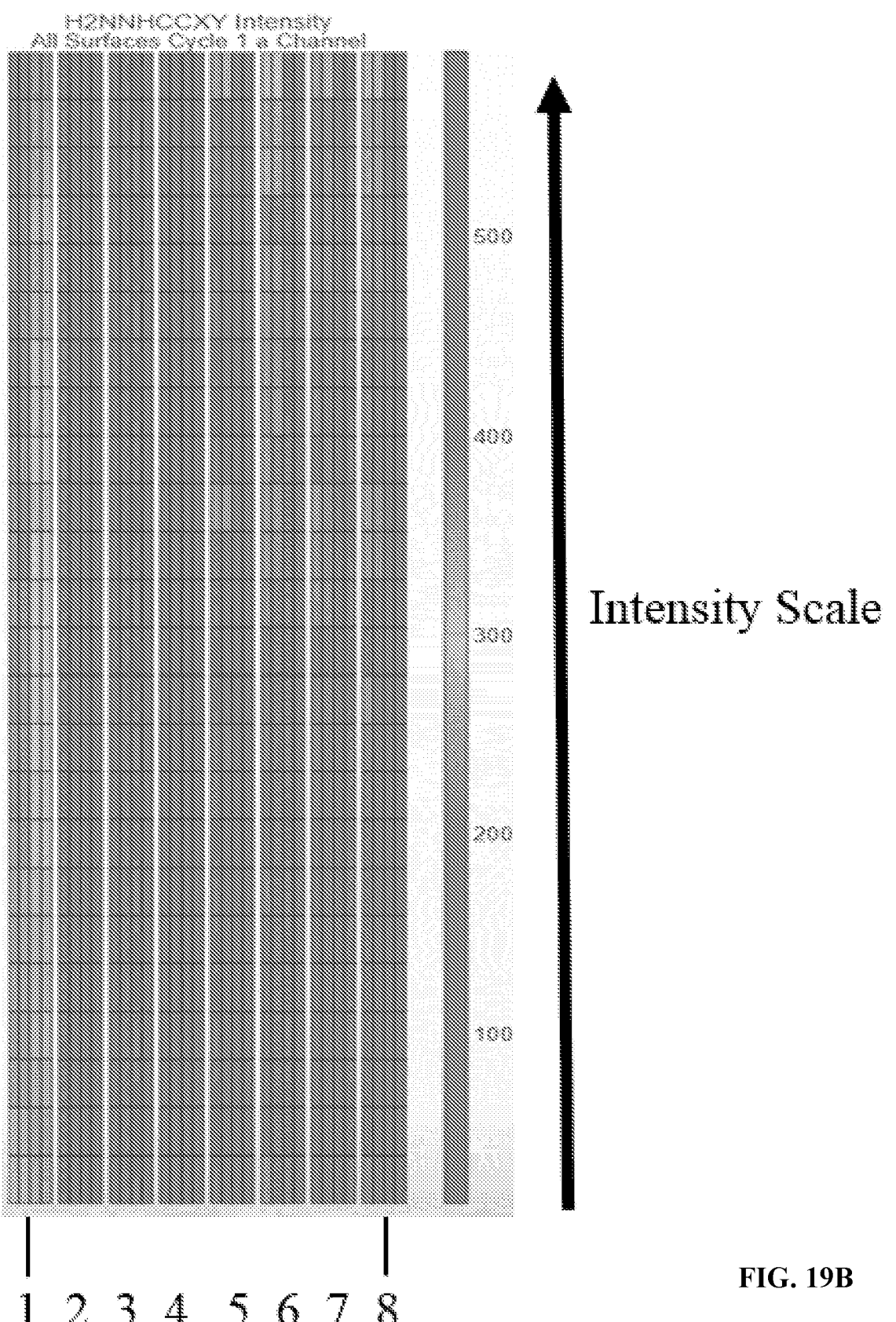

FIGS. 19A-19B show the requirement of a non-reducing sugar, either trehalose or sucrose to stabilize the lyophilised enzymes. Lyophilised PEG free Ras6T clustering activity immediately upon freeze-drying (FIG. 19A) and after incubation of the pellet at 37° C. 16 hours (FIG. 19B). All lyophilised formulations have activity after lyophilisation. However, once the cake has been incubated at 37° C. for 16 hours, the resuspended lyophilised pellets without non-reducing sugars produced very dim clusters (dark blue lanes 2-4). All lanes containing sucrose or trehalose in the lyophilisation mix retains activity (yellow to orange).

TABLE 1

| Lane assignments for Flowcell Intensity images measuring activity of ExAmp mix in FIG. 19. | |
| --- | --- |
| Lane | Sample Type |
| 1 | EPX123 not-lyophilised (Control) |
| 2 | Ras6T Lyophilised |
| 3 | Ras6T lyophilised + Triton X-100 0.005% |
| 4 | Ras6T lyophilised + Triton X-100 0.01% |
| 5 | Ras6T lyophilised + Trehalose 100 mM |
| 6 | Ras6T lyophilised + Trehalose 200 mM |
| 7 | Ras6T lyophilised + Sucrose 100 mM |
| 8 | Ras6T lyophilised + Sucrose 200 mM |

Figure 20:
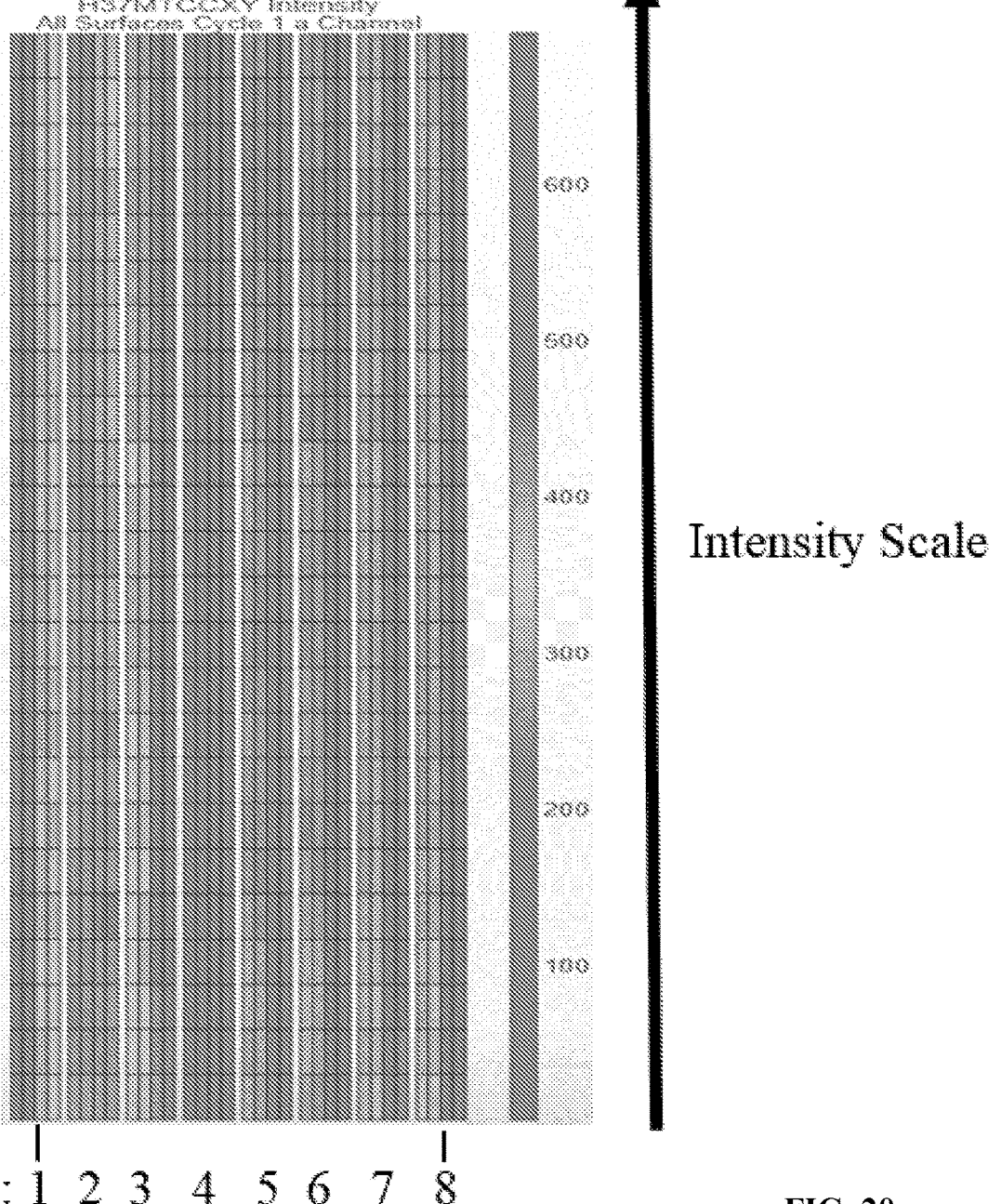
FIG. 20 shows stability of lyophilised Ras6T after 37° C. incubation for 5 days. Lyophilisation of PEG free Ras6T with magnesium (lane 8) requiring only water for resuspension.

Stability of lyophilised Ras6T after 37° C. incubation for 5 days. Lyophilisation of PEG free Ras6T with magnesium (lane 8) requiring only water for resuspension is shown in FIG. 20.

TABLE 2

| Lane assignments. Flow Cell Intensity images measuring activity of Ras6T mix in FIG. 20. | | | |
| --- | --- | --- | --- |
| Lane | Sample Type | Lyophilised | Resuspension buffer |
| 1 | EPX123 (Control) | No | None |
| 2 | EPX123 (Control) | No | None |
| 3 | Ras6T (Control) | No | None |
| 4 | Ras6T − TCEP − Mg | Yes | TCEP/Mg solution |
| 5 | Ras6T − TCEP − Mg +100 mM Sucrose | Yes | TCEP/Mg solution |
| 6 | Ras6T − TCEP + Mg +100 mM Sucrose | Yes | TCEP solution |
| 7 | Ras6T + TCEP − Mg +100 mM Sucrose | Yes | Mg solution |
| 8 | Ras6T + TCEP + Mg + 100 mM Sucrose | Yes | water |

It was surprising that during the process of freeze-drying in the presence of Mg, the proteins did not aggregate to the point of being inactive and were still able to maintain activity in the lyophilised state at elevated temperatures.

These findings are surprising in view of publications that found binding of Mg decreases the thermal stability of RecA (Kim et al., "RecA Requires Two Molecules of $Mg^{2+}$ Ions For Its Optimal Strand Exchange Activity In Vitro," *Nucleic Acids Research* 46:2548-59 (2018), which is hereby incorporated by reference in its entirety), and findings that aggregation of RecA protein as a function of Mg (Roman et al., "Relationship of the Physical and Enzymatic Properties of *Escherichia coli* RecA Protein to Its Strand Exchange Activity," *Biochemistry* 25:7375-85 (1986), which is hereby incorporated by reference in its entirety).

Example 7—ExAmp Formulations Per Platform do not Vary Significantly by Component, Just Concentrations of Each Component Current commercialized lyophilised RPA mixes from TwistDx, are formulated in a two tube format, with enzymes/substrates in one tube, and PEG+Magnesium separated in a second tube. Relatively the same components are contained in ExAmp formulations, however the biggest differences are in the concentrations and those are optimized for the particular flow cell used.

Lyophilising the raw component alone like Bsu or ATP and then mixing the dry components microspheres together in the appropriate amounts allows for development of a lyophilisation method once for each component which then does not need to change with each interactive platform, the raw microspheres would just need to be filled with a different amount of component. This also allows the flexibility to leave out some components that are not needed like PEG or UvsY for some formulations.

Example 8—Complex Reagent Formulations are a Compromise Between the Stability and Activity of Each Individual Component Creatine Kinase (CK) and Phosphocreatine (PC) in ExAmp. Components CK and PC in ExAmp or optimally active and stable at different pHs. Combining the components in liquid form for liquid formulation or lyophilisation in full reagents (complex reagent) cakes or microspheres requires using a pH that is between the optimum of both components.

Complex reagent formulations still may require separated components only to be combined immediately before chemistry due to interactions that cause increased degradation in the liquid form (liquid staging of complex reagents in manufacturing before lyophilisation can occur).

Figure 21:
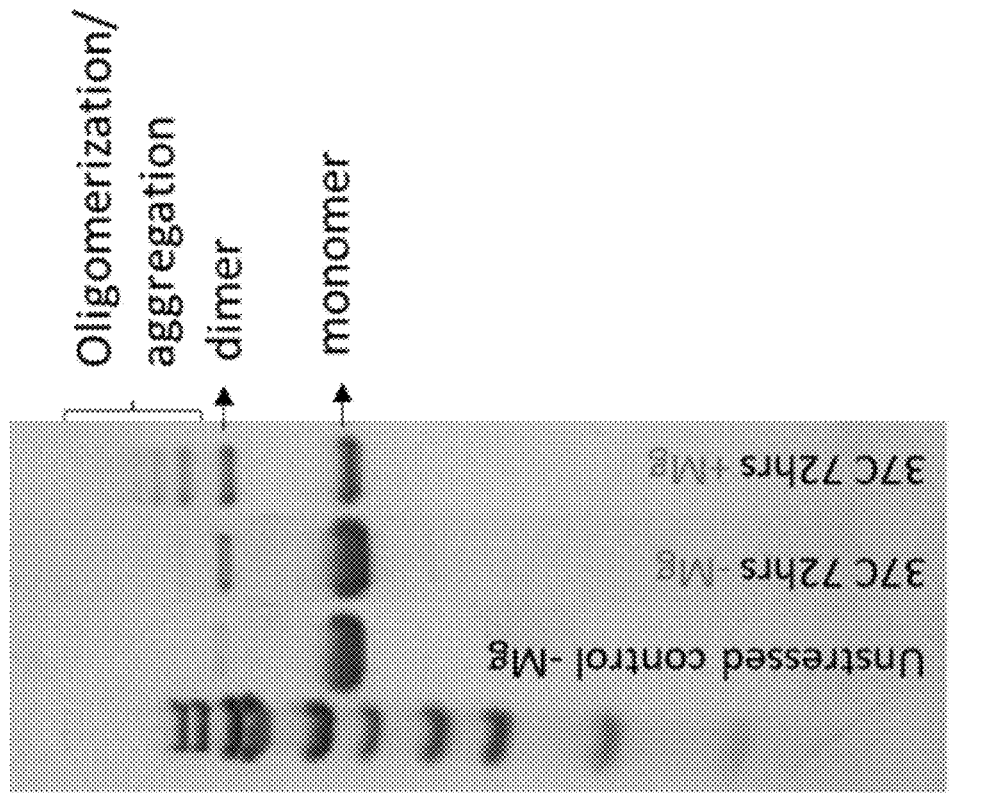
FIG. 21 shows a comparison of recombinase in stressed conditions that mimic accelerated storage conditions with and without magnesium on SDS-PAGE reduced IVIES gel.

Recombinase and Mg. Magnesium, a cofactor that is required to catalyze enzyme reactions, will cause oligomerization or aggregation of some enzymes like recombinase when stored together in liquid form, which during storage stress can yield an inactive enzyme over time (FIG. 21). Because of this, a magnesium solution is traditionally formulated in a separate vial only to be combined with enzymes immediately before the reaction. Once lyophilised, combining dry components together in the same vial should not exhibit any interactions as the lack of water reduces molecular movement significantly

Example 9—Microspheres Enable Formulating for Optimal Activity

It is common for enzymes to have storage conditions that are optimum for stability and a different condition for optimum activity. One benefit of raw component microspheres is being able to formulate the active component in stable conditions for storage and also generating a microspheres that contains a different buffer, salt, etc., that changes the formulation environment to yield highest performance immediately upon resuspension of the mixture that contains both active component microsphere and the "activity buffer" microsphere.

Figure 22:
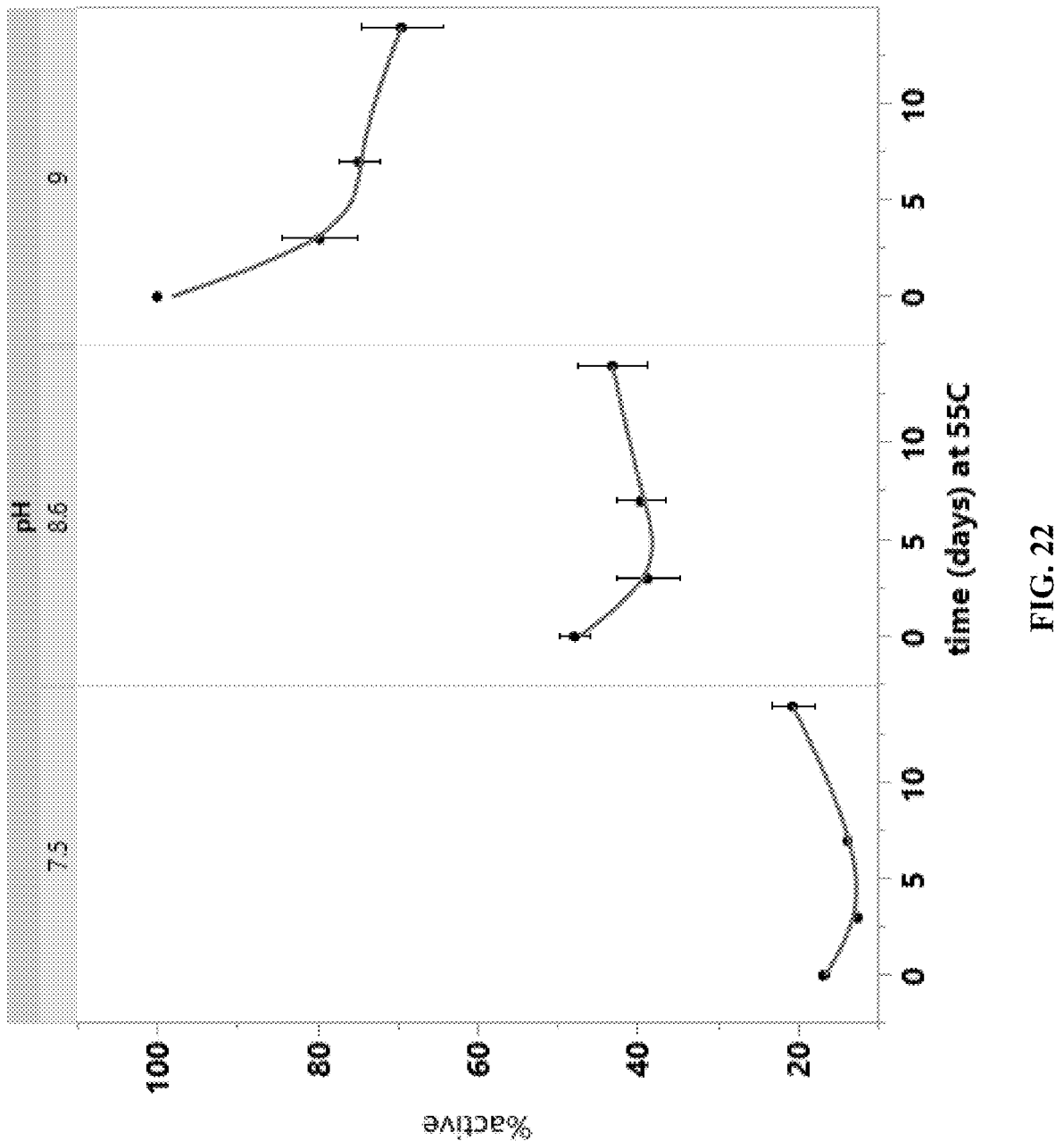
FIG. 22 shows that exo enzyme has high stability at pH 7.5, but only 20% activity relative to at pH 9. However at pH 9, the rate of degradation over time is significantly increased.
Figure 23:
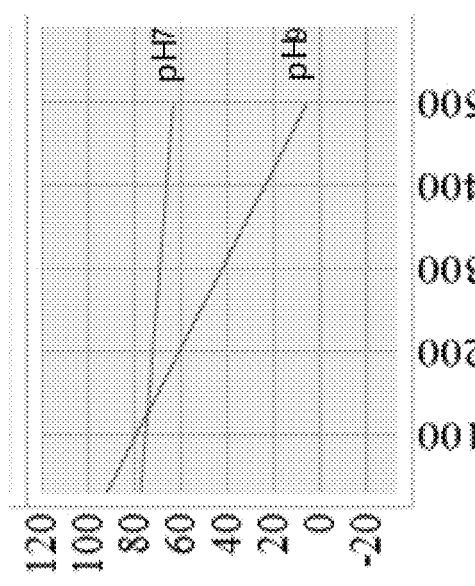
FIG. 23 shows Tm (melting temperature) of a protein is one of the indicator of protein stability (higher Tm=higher stability). OGG has a higher Tm in higher salt conditions, but lower activity in higher salt conditions. OGG as described herein is 8-Oxoguanine DNA Glycosylase enzyme—a thermostable enzyme extracted from *Methanococcus janaschii*.
Figure 23:
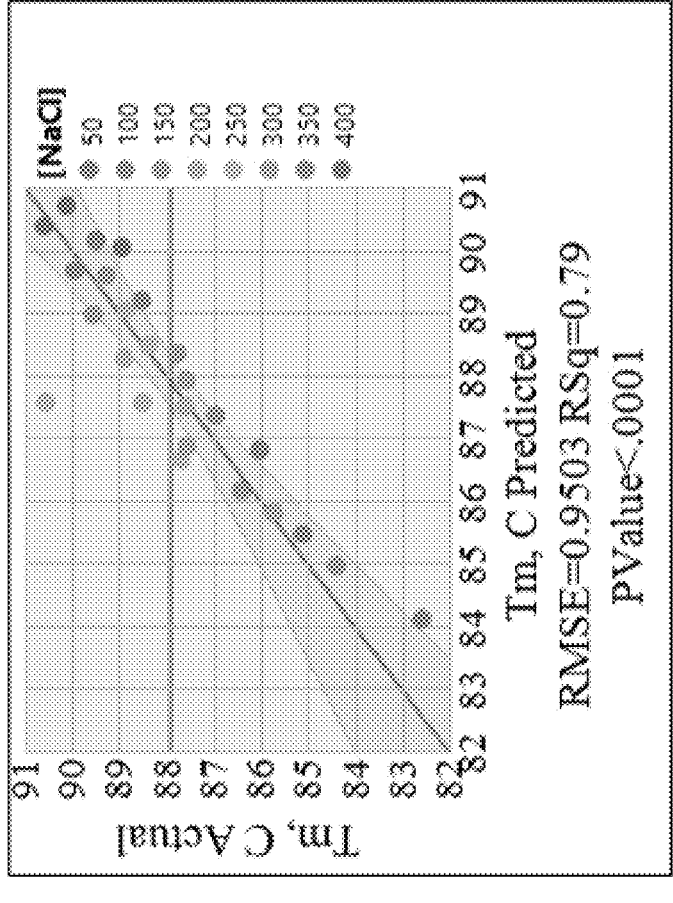

FIG. 22 shows that exo enzyme has high stability at pH 7.5, but only 20% activity relative to at pH 9. However at pH 9, the rate of degradation over time is significantly increased. FIG. 23 shows that Tm (melting temperature) of a protein is one of the indicator of protein stability (higher Tm=higher stability). OGG has a higher Tm in higher salt conditions, but lower activity in higher salt conditions.

Figure 24:
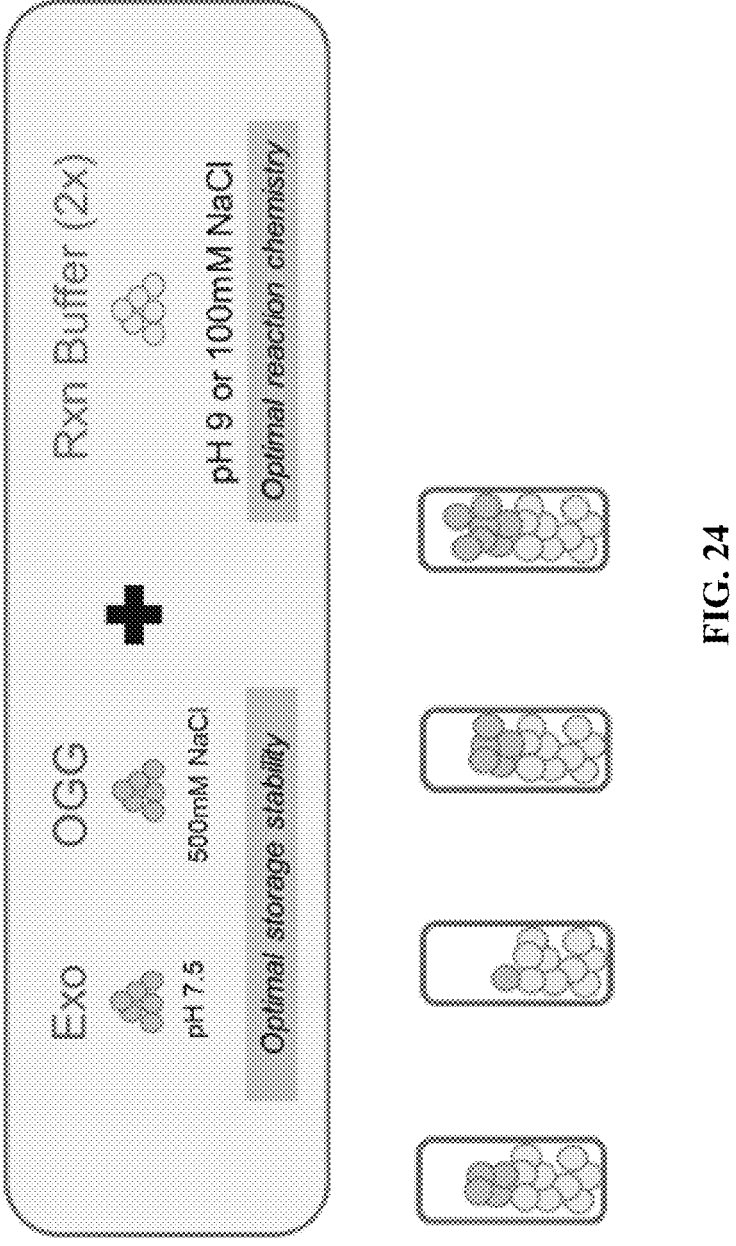
FIG. 24 shows use of raw component microspheres formulated at optimum storage conditions and then utilizing a reaction buffer microspheres added to the same container so that upon resuspension, the reaction buffer will change the formulation environment that is optimal for activity.

FIG. 24 shows the use of raw component microspheres formulated at optimum storage conditions and then utilizing a reaction buffer microspheres added to the same container so that upon resuspension, the reaction buffer will change the formulation environment that is optimal for activity. FIG. 24 also shows the flexibility of varying concentration amounts of an active component or even combining several active components that are traditionally separated in individual vials due to storage formulation incompatibility.

Example 10—Microsphere Generation Process

In this example, the feasibility of a bulk format of lyophilisation via microbeads and microspheres, to stabilize sequencing reagents is demonstrated. Microsphere generation is made possible with the concept of spray freeze drying. Spray freeze drying is a two-step process whereby liquid reagent is first sprayed into a vertical cold tower through nozzles to form frozen microspheres. Subsequently, these frozen microspheres are dried through tray lyophilisation or other freeze drying equipment to obtain dry microspheres. Microbeads can also be made by dropping sequencing reagents directly into liquid nitrogen to form frozen microbeads, and subsequently freeze drying them in lyophilisers.

The typical size for microspheres can range from 200-800 um in size depending on the size of the nozzle used to generate the droplets.

Formulation considerations. There are a few key considerations when developing the formulations for sequencing reagents microspheres. The active components of the sequencing reagents need to be stabilized sufficiently using excipients and thermal stabilizers. In addition, it is also important for the dry microspheres to have sufficient mechanical strength to withstand any vibrational stress.

Figure 25:
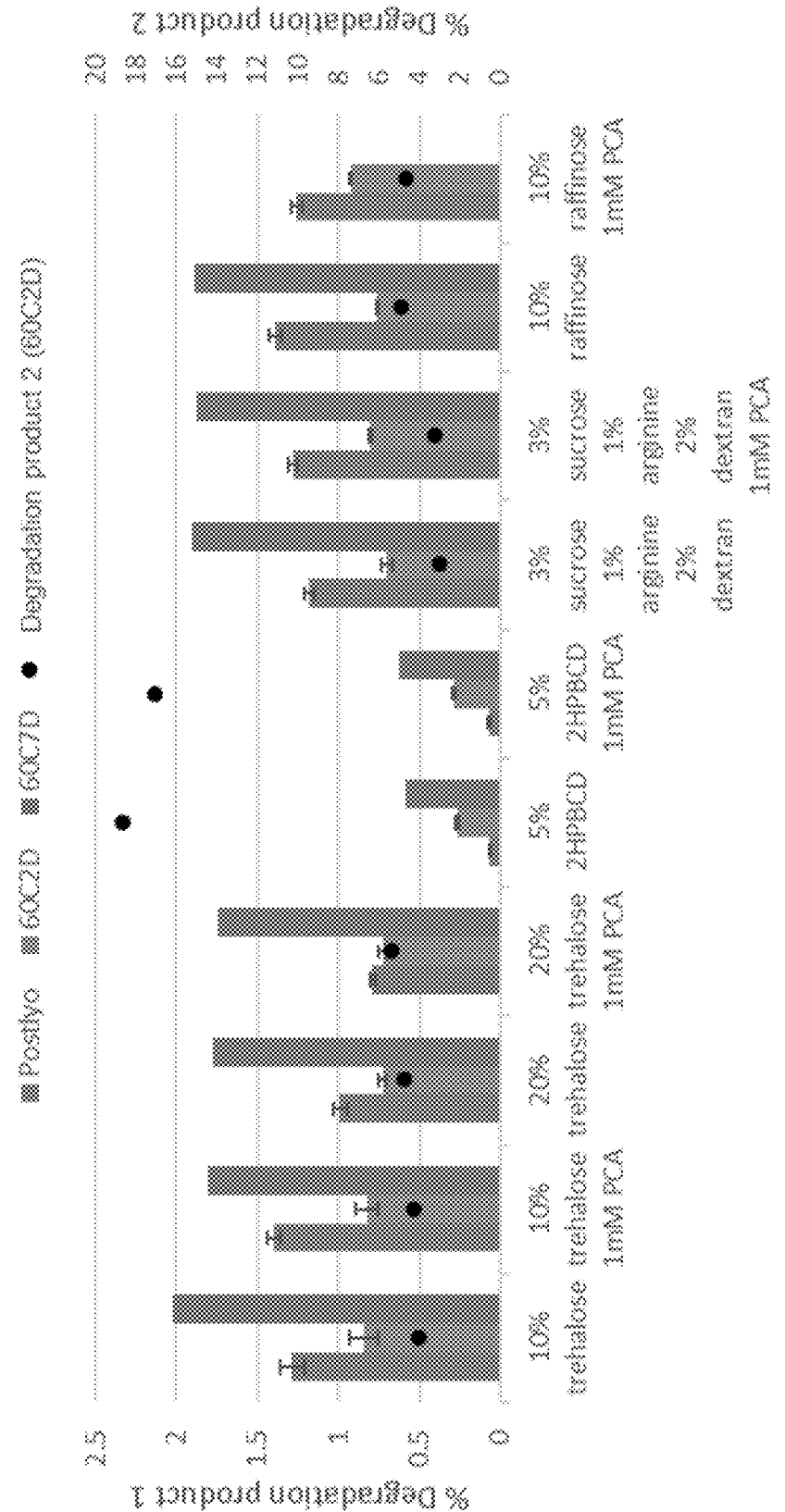
FIG. 25 shows analytical results of nucleotide degradation products for lyophilised cake of different formulations.
Figure 26:
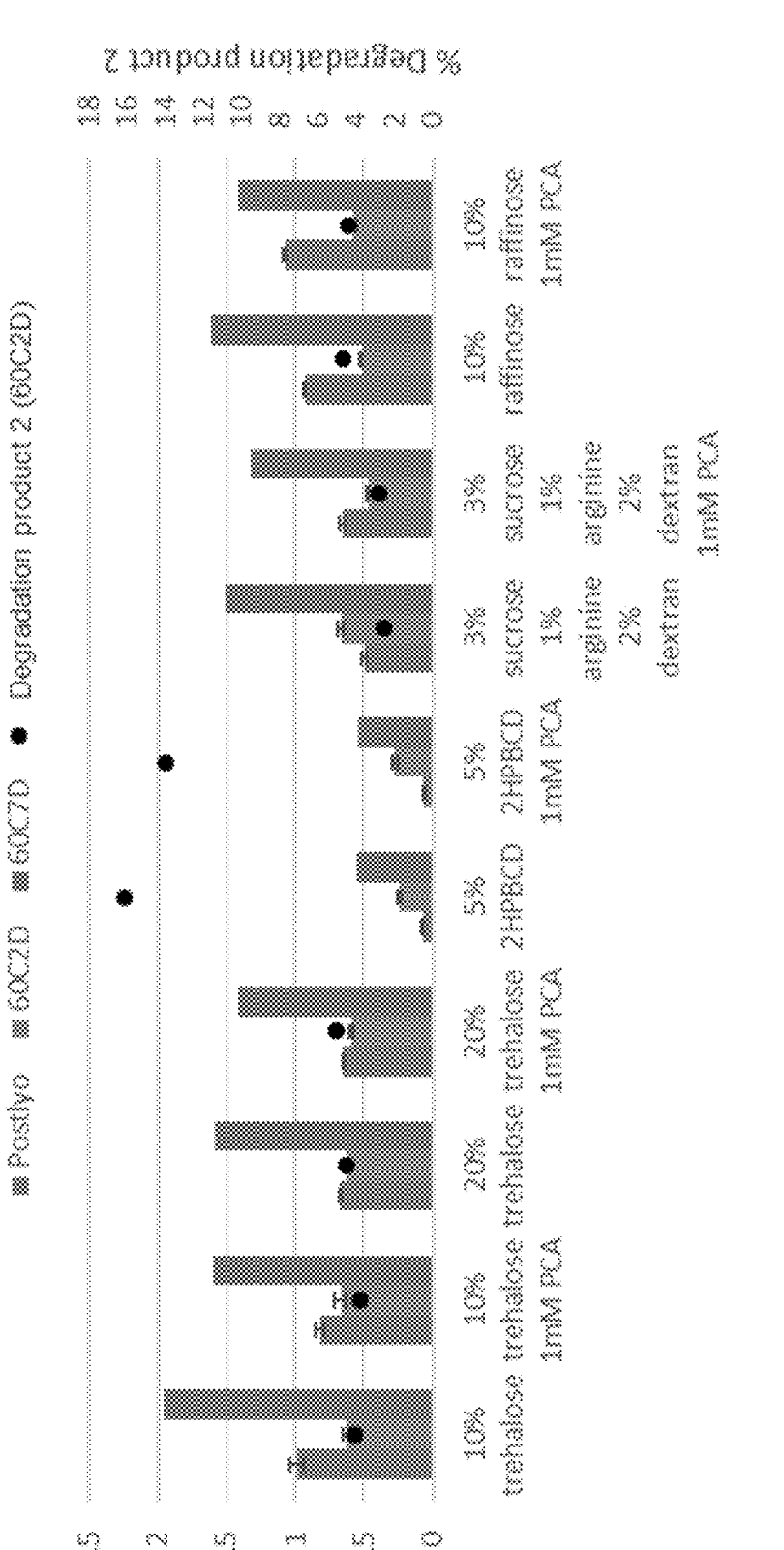
FIG. 26 shows analytical results of nucleotide degradation products for lyophilised beads of different formulations.
Figure 27:
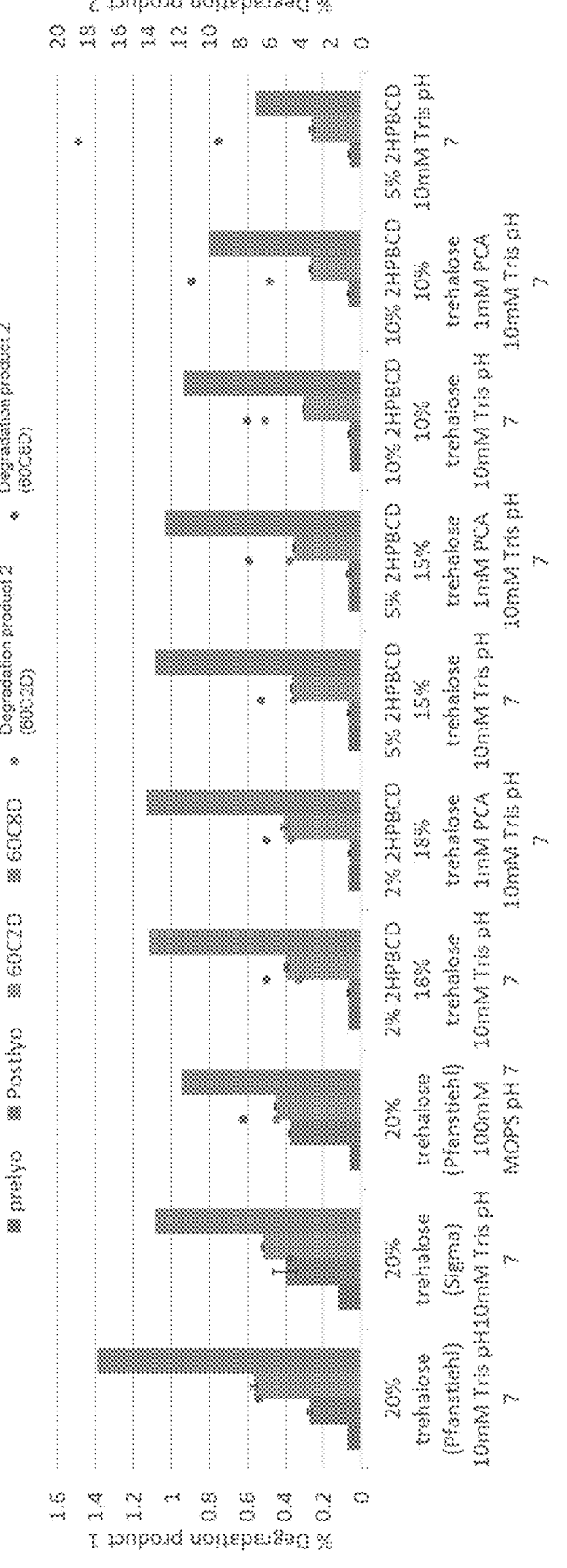
FIG. 27 shows analytical results of nucleotide degradation products formation for lyophilised beads at higher excipient concentrations.

Incorporation mix. Different excipients were screened for stabilizing modified nucleotides used in sequencing, for both lyophilised cake and beads. As seen in FIGS. 25 and 26, lyophilised beads exhibits lower formation of the degradation products 1 and 2. FIG. 27 shows analytical result of nucleotide degradation products formation for lyophilised beads at higher excipient concentrations.

Figure 28B:
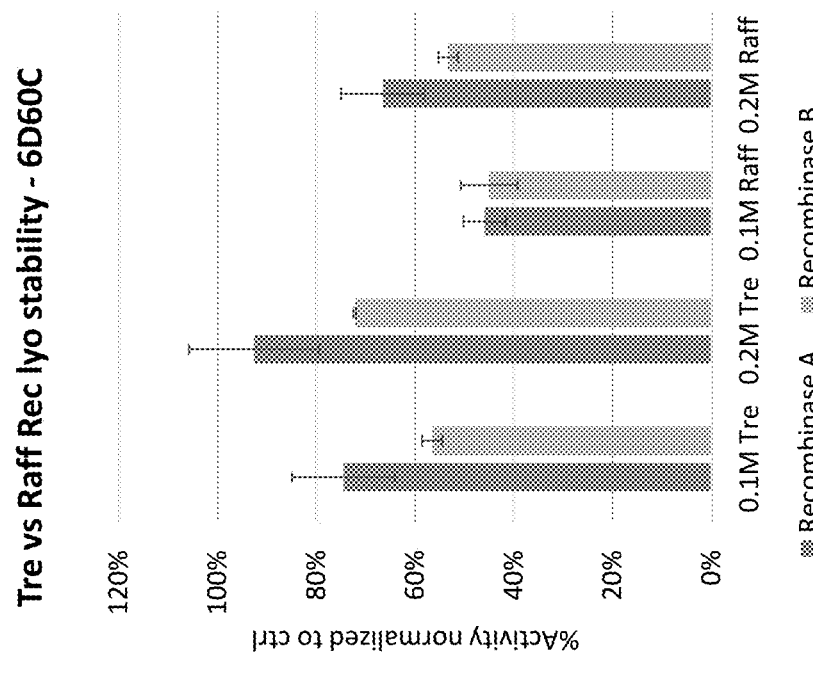
FIGS. 28A-28B show lyophilised recombinase stability in the presence of Trehalose or Sucrose (FIG. 28A) and lyophilised recombinase A and recombinase B stability in the presence of Trehalose or Raffinose (FIG. 28B).
Figure 28A:
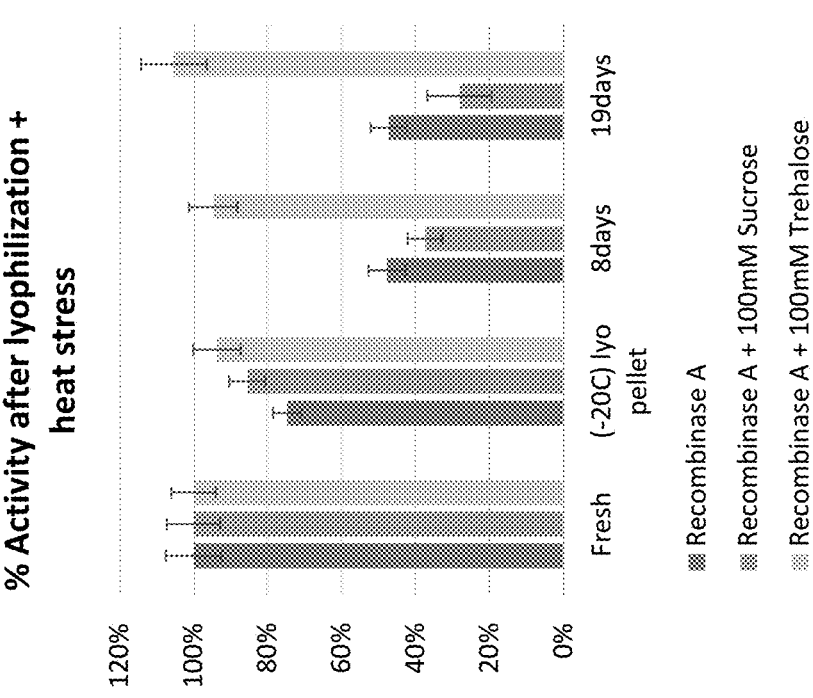

Clustering enzymes. The recombinase for enzymatic clustering, was initially screened for lyophilisation stability in the presence of a non-reducing sugar stabilizers (trehalose, sucrose, and raffinose). Trehalose conferred the highest stabilization of the enzyme after lyophilisation and heat stress as shown in FIGS. 28A-28B.

Due to the surface charge of the recombinase enzyme, high salt concentrations are needed to prevent enzyme precipitation in high protein concentration formulation. However, high salt solution are more difficult to freeze, produce a lower Tg' and are less efficient in water removal during the lyophilisation process. This dependency on [NaCl] and enzyme solubility can be alleviated in the presence of a non-reducing sugar such as trehalose particularly for the Recombinase B.

Clustering mix. The clustering mix formulation, contain significant small molecule components (salts and substrate) to depress the Tg' of the formulation below what is feasible for manufacturing. Further excipient screening to increase the Tg' of the clustering mix include trehalose, sucrose, hydroxypropyl-beta-cyclodextrin, polyvinylpyrrilidone, dextran, maltodextrin, and mannitol. It was found that formulations containing mannitol showed a lower % of aggregation amongst the tested mixtures as shown in FIG. 29.

Analytical and function test on microspheres—Mechanical stability. The mechanical stability of lyophilised material was determined through monitoring the modulus or toughness (integral of the Young's Modulus up to the first crack (i.e., failure)) and fracture stress (max stress at failure) using the Micropress. The Micropress (Biopharma) uses a linear actuator to gently compress the lyophilised material while a load cell accurately measures the force applied.

Figure 29:
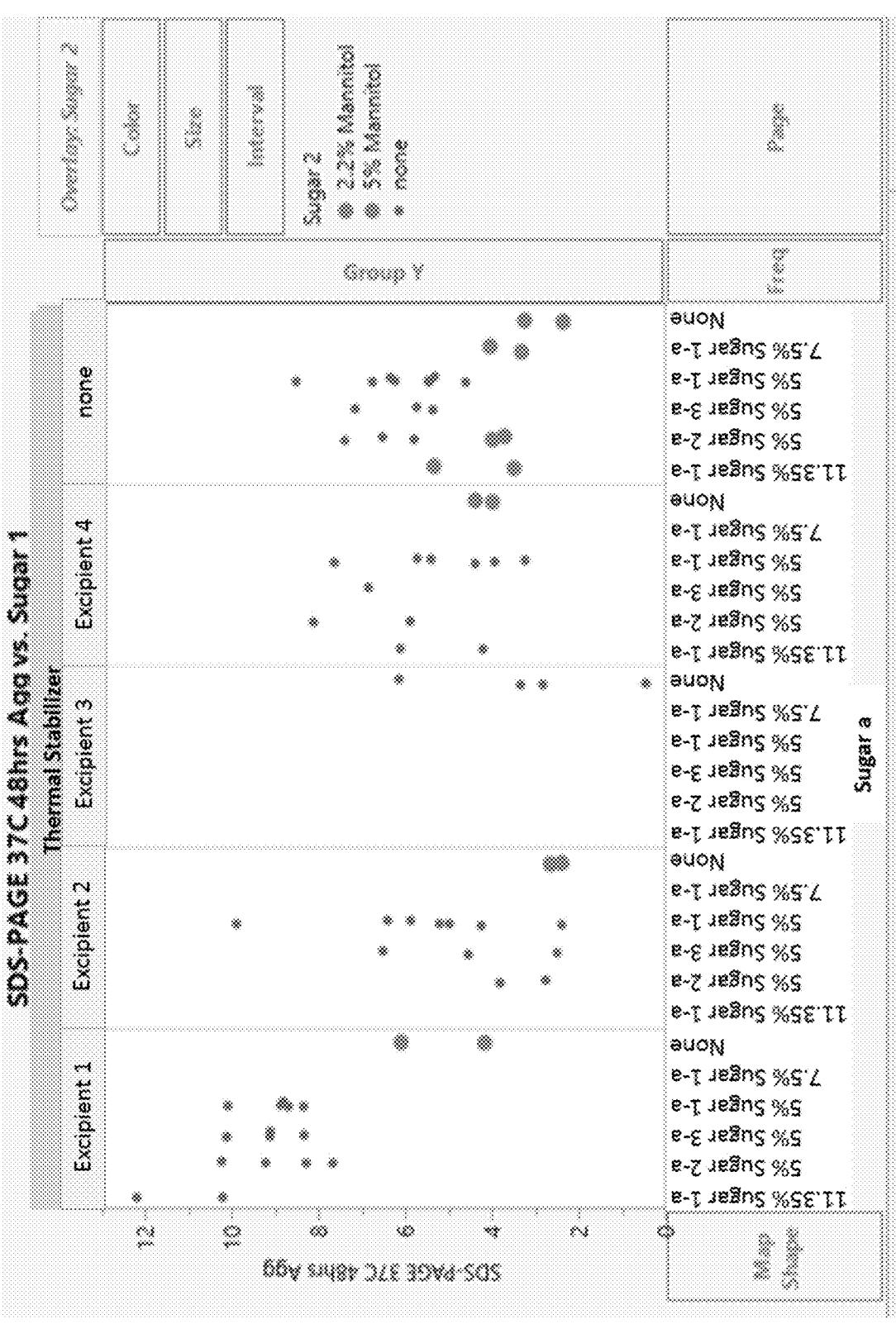
FIG. 29 shows relative aggregate formation of heat stressed liquid clustering mix at 37° C. in a formulation screen.
Figure 30:
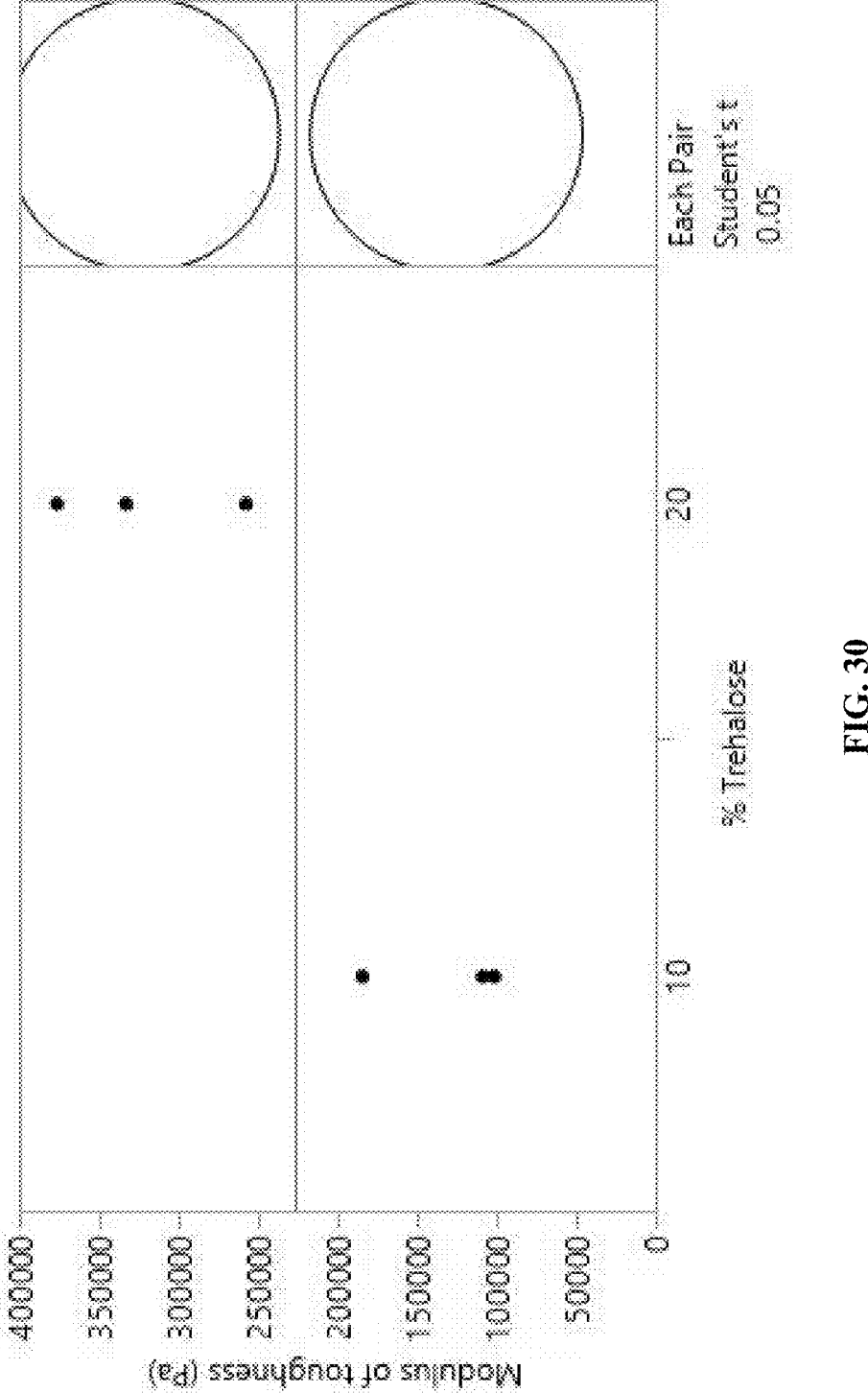
FIG. 30 shows modulus of toughness (integral of Young's modulus to $1^{st}$ fracture) for 10% and 20% trehalose content in microspheres.

As seen in FIGS. 29 and 30, an increase in excipient content results in higher modulus of toughness and fracture stress in microspheres.

Figure 31:
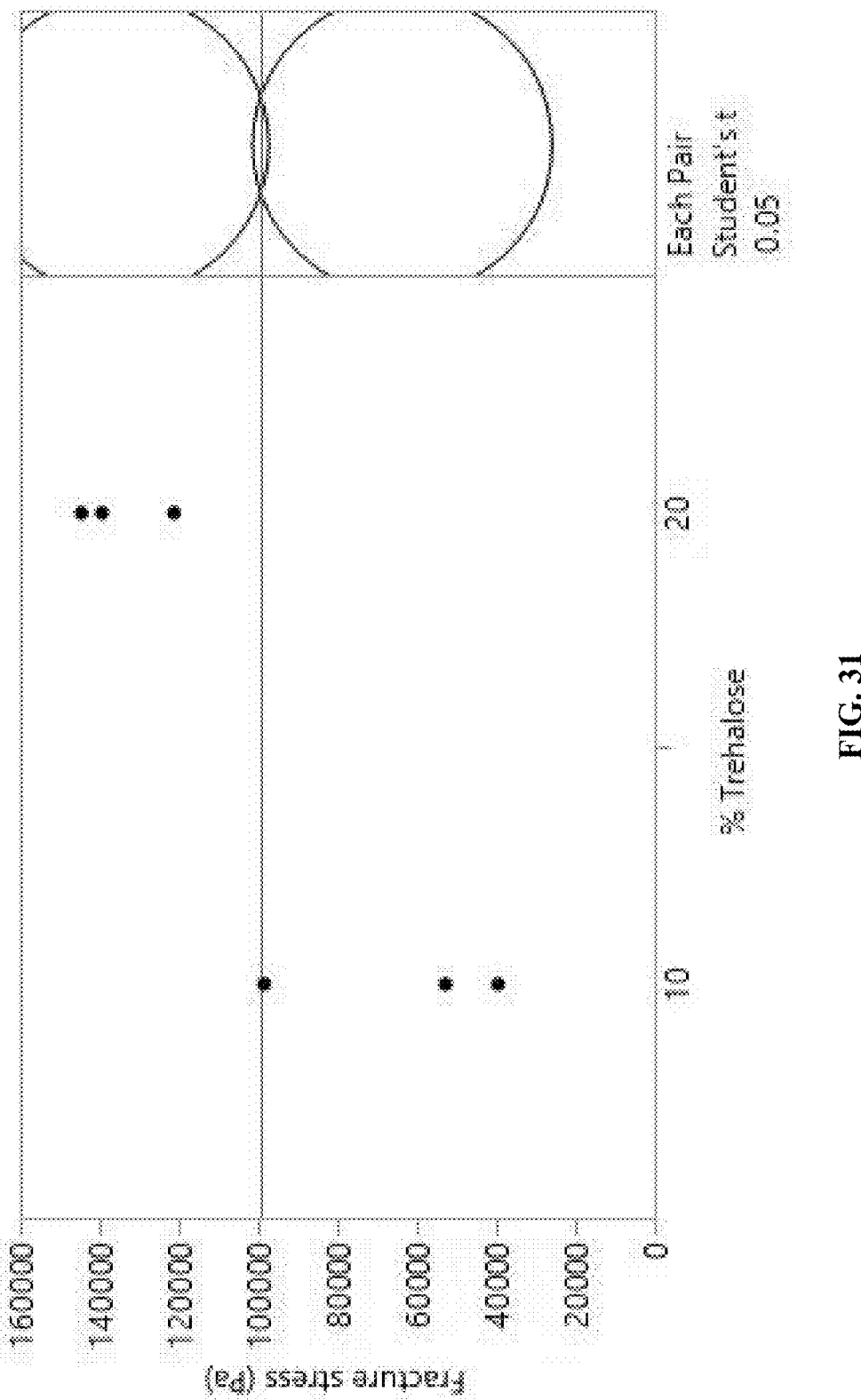
FIG. 31 shows fracture stress (maximum stress measured before the $1^{st}$ fracture) for 10% and 20% trehalose content of microspheres.
Figure 32:
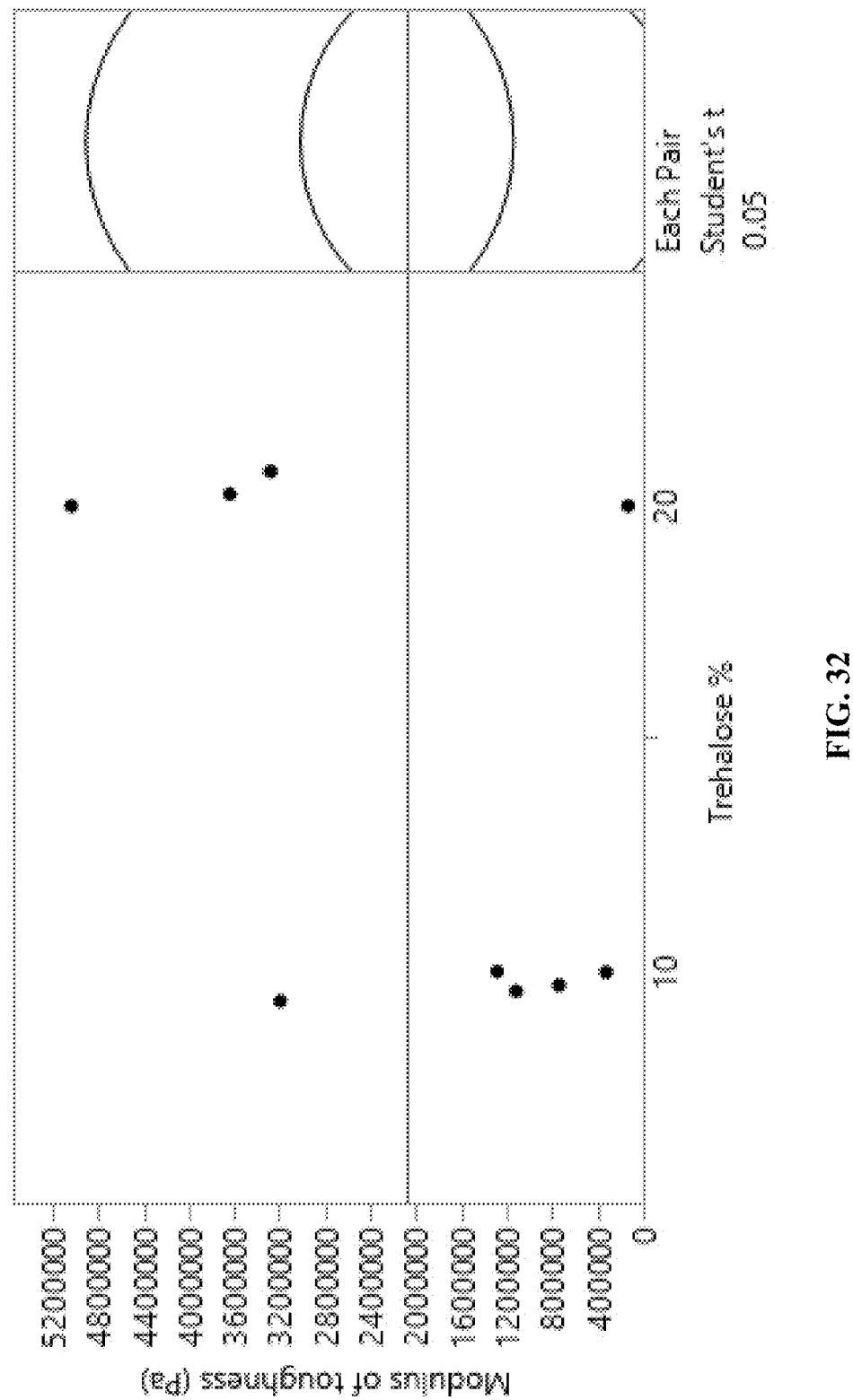
FIG. 32 shows modulus of toughness (integral of Young's modulus to $1^{st}$ fracture) for 10% and 20% trehalose content in lyophilised cake.
Figure 33:
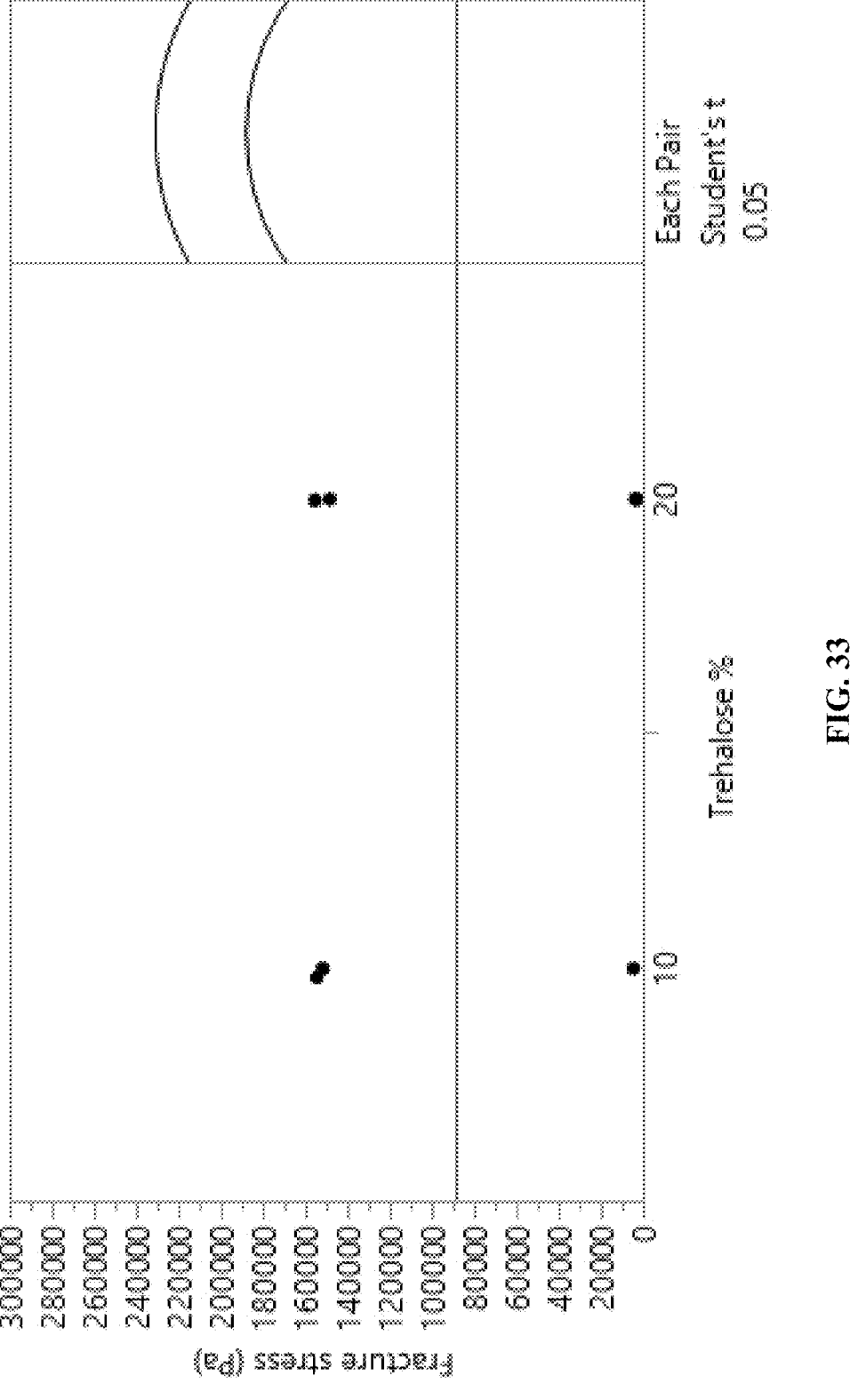
FIG. 33 shows fracture stress (maximum stress measured before the $1^{st}$ fracture) for 10% and 20% trehalose content of lyophilised cake.

Lyophilised cake possess greater modulus of toughness as compared to microspheres (FIGS. 30 and 32). Similarly, lyophilised cakes exhibit greater fracture stress as compared to microspheres (FIGS. 31 and 33).

Static charge. Due to the nature of microspheres, static charge may result from the presence of an excess of positive or negative charges confined within a small volume. As such, it is important to understand the extend of static charge generated by the microspheres.

Figure 34:
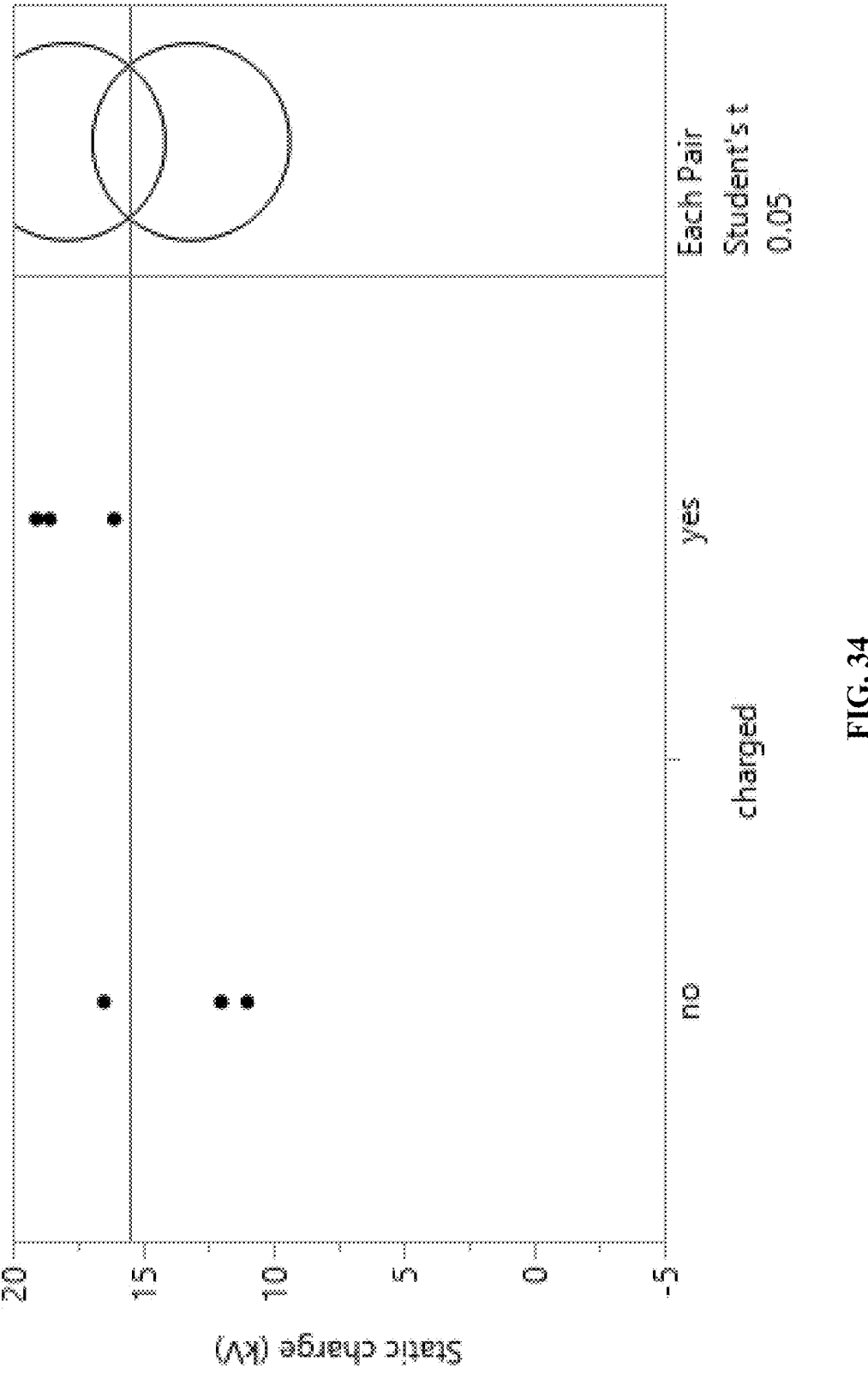
FIG. 34 shows static charge of 10% trehalose microspheres.
Figure 35:
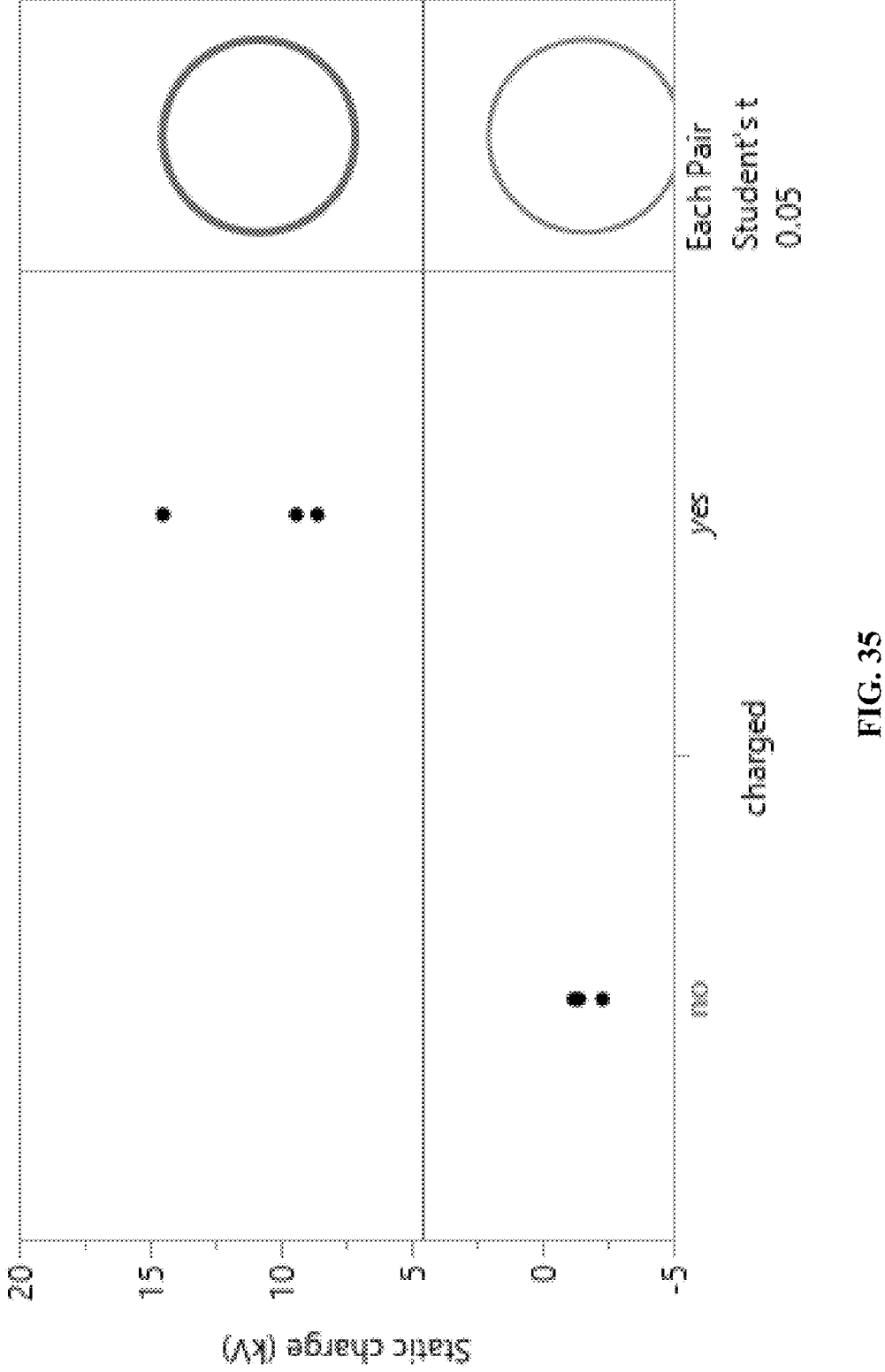
FIG. 35 shows static charge of 20% trehalose reagent microspheres.

The SMC IZH10 is a non-contact electrostatic meter which measures the charge of objects. FIGS. 34 and 35 show the change in measured static charge of 10% trehalose and 20% trehalose reagent microspheres respectively. To induce a change in charge, the microspheres in their containing glass vials were rolled for 15 minutes at 100 rpm. In both cases, resulting from the friction of the microspheres on the glass, the static charge increased. It is also interesting to note that the presence of the reagent as well as the components present in their storage media result in a much lower charge of the microspheres in their native state.

Rehydration. An in-house system was developed to compare the rehydration efficiency of microspheres and lyophilised cake.

Rehydration from the bottom of the vial led to significant microspheres floating on the rehydration solution. In addition, due to the contact of sipper with the microspheres, the static charge from the microspheres resulted in them being attracted to the sipper. Despite these observations which can be alleviated by dispensing the rehydration buffer above the microspheres and installing a wait time in the recipe.

Figure 36:
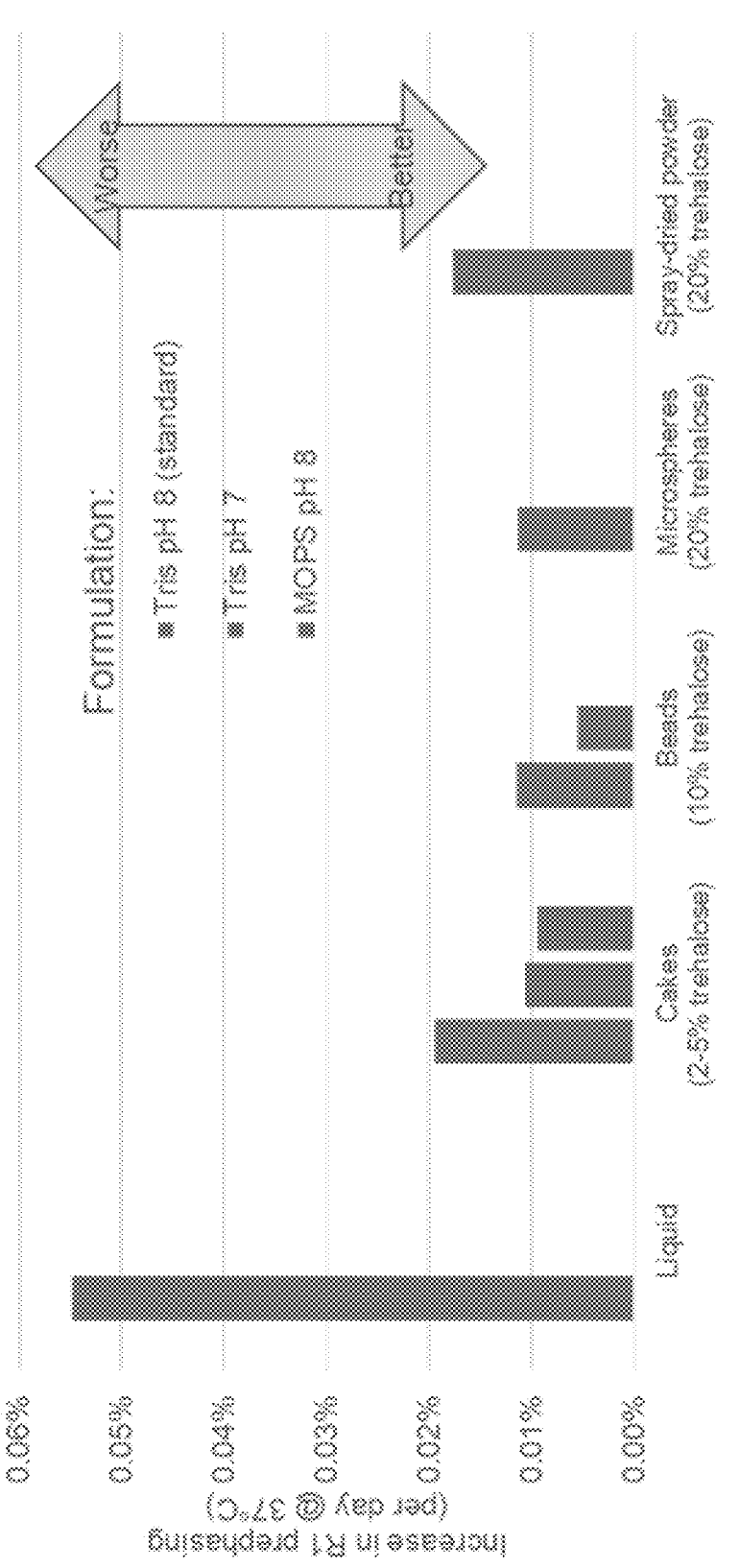
FIG. 36 shows an increase in R1 prephasing per day at 37° C. for ffNs of different lyophilised format.

Sequencing. Microspheres and lyophilised cakes were sequenced on the Miniseg™ and the increase in R1 prephasing per day at 37° C. is shown on FIG. 36. From FIG. 36, it shows that microspheres have the lowest increase in R1 prephasing as compared to lyophilised cakes.

Example 11—Lyophilisation of Sequencing Reagents into Beads as a Bulk Format The introduction of lyophilisation into products will focus on lyophilising in the cake format. Stability of lyophilised reagent such as ffNs, polymerase and Ras6T has shown to be more superior in cake format than in liquid form.

While most experiments are currently looking into fine tuning the stability of reagents in lyophilised cake format, there is also an ongoing effort to lyophilise reagents in the bead format.

In this example, an alternative format to lyophilisation is disclosed, bead format, to further stabilize reagents from the existing lyophilised cake. The SBS reagents that were successfully lyophilised in bead format are ffN solution, polymerase and Ras6T from ExAmp. Library preparation reagents were also lyophilised into beads and have shown comparable results to the control. An in-house vibrational stress test was also designed to assess the mechanical stability of the beads.

Bead lyophilisation process. To lyophilise in the bead format, reagents would first have to be dripped (forming droplets) into a pool of liquid nitrogen. This allows the droplets to freeze into spheres. Once the droplets are frozen, they are transferred into glass vials and placed into the lyophiliser.

Four different methods of dripping reagent into liquid nitrogen were explored—manual pipetting, peristaltic pump, dropper and an auto pipet. Peristaltic pump and auto pipet result in the most consistent bead size. Auto pipet was chosen to create droplets as it allows the flexibility to manipulate the volume of beads.

The different volume of lyophilised beads was explored using the auto pipet. Larger bead volume at 35 uL and above had resulted in the cracking and breaking of beads. Hence, to maximize the volume of reagent while minimizing the number of beads, 25 uL bead volume was selected to be the most optimal size.

Example 12—Bead Lyophilisation of ffN Solution

Bead lyophilisation of ffN solution was first performed using 1×ffN solution, where formulation was prepared with respect to the ffNs ratio present in Incorporation Mix. Excipient was then added into the formulation. Excipient chosen was based on earlier excipient screen of trehalose and sucrose on lyophilised ffN cakes.

50% trehalose and a combination of 20% trehalose and 20% sucrose resulted in low 3'OH formation.

10% trehalose is the current best excipient for lyophilising ffN beads.

Figure 37:
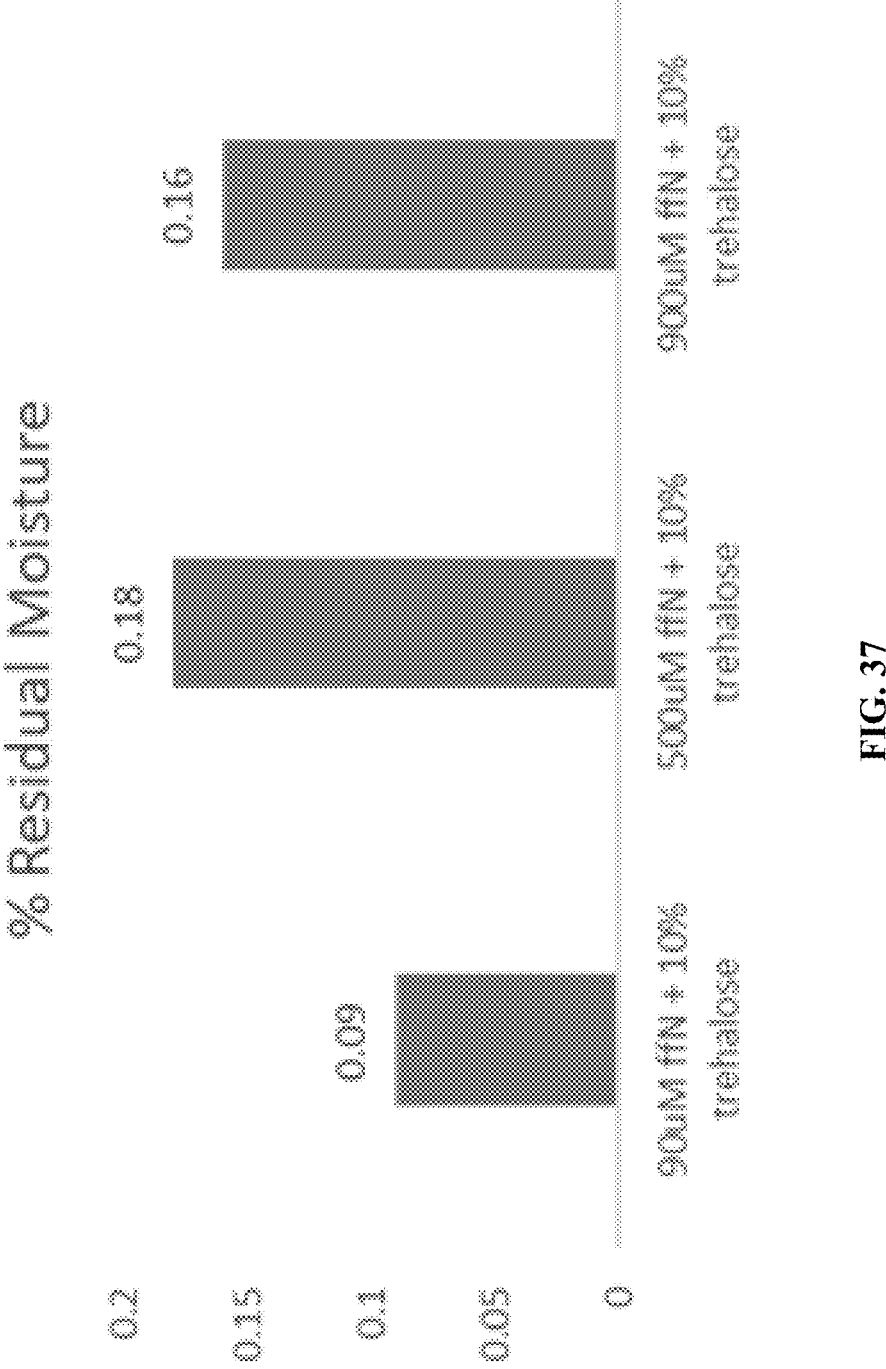
FIG. 37 shows lyophilised ffN beads of 1× and 10×ffN solution. Residual moisture for all lyophilised beads are below 0.2%.

Besides lyophilising at 1×ffN solution, lyophilising ffN beads at higher concentration of ffN, 10×ffN solution, was explored. As seen in FIG. 37, 10× beads are evenly shaped and has no difference with 1×ffN beads in terms of appearance. The residual moisture of the beads are low (<0.2%), signifying that freeze drying process was successful.

Stability of 10×ffN lyophilised beads up to 7 days at 37° C. is demonstrated, where the % R1 prephasing of 10×ffN lyophilised beads staged at 37° C. for 7 days is within 2 standard deviation to liquid control.

Figure 38:
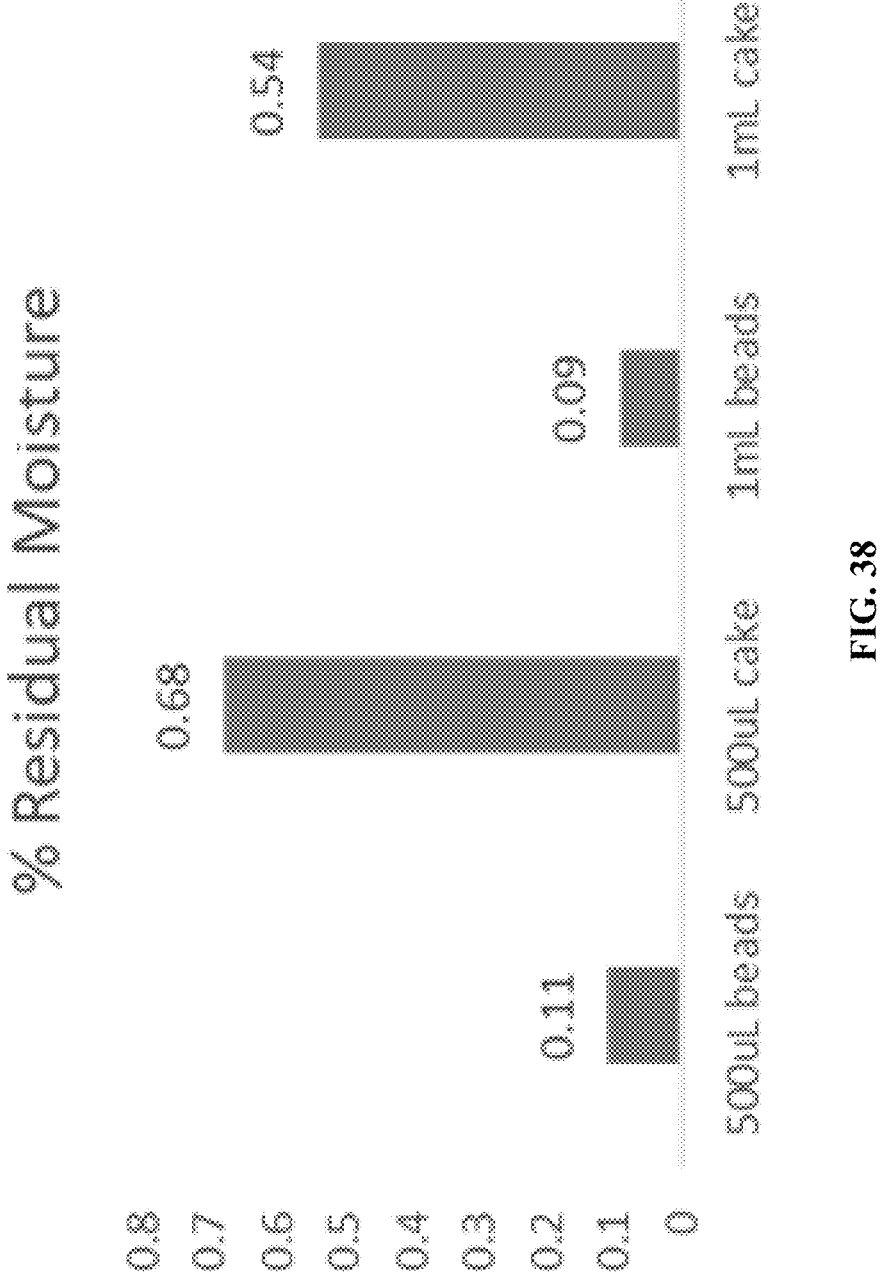
FIG. 38 shows a comparison of lyophilised ffN cake and lyophilised ffN beads for a 1×ffN solution.
Figure 39:
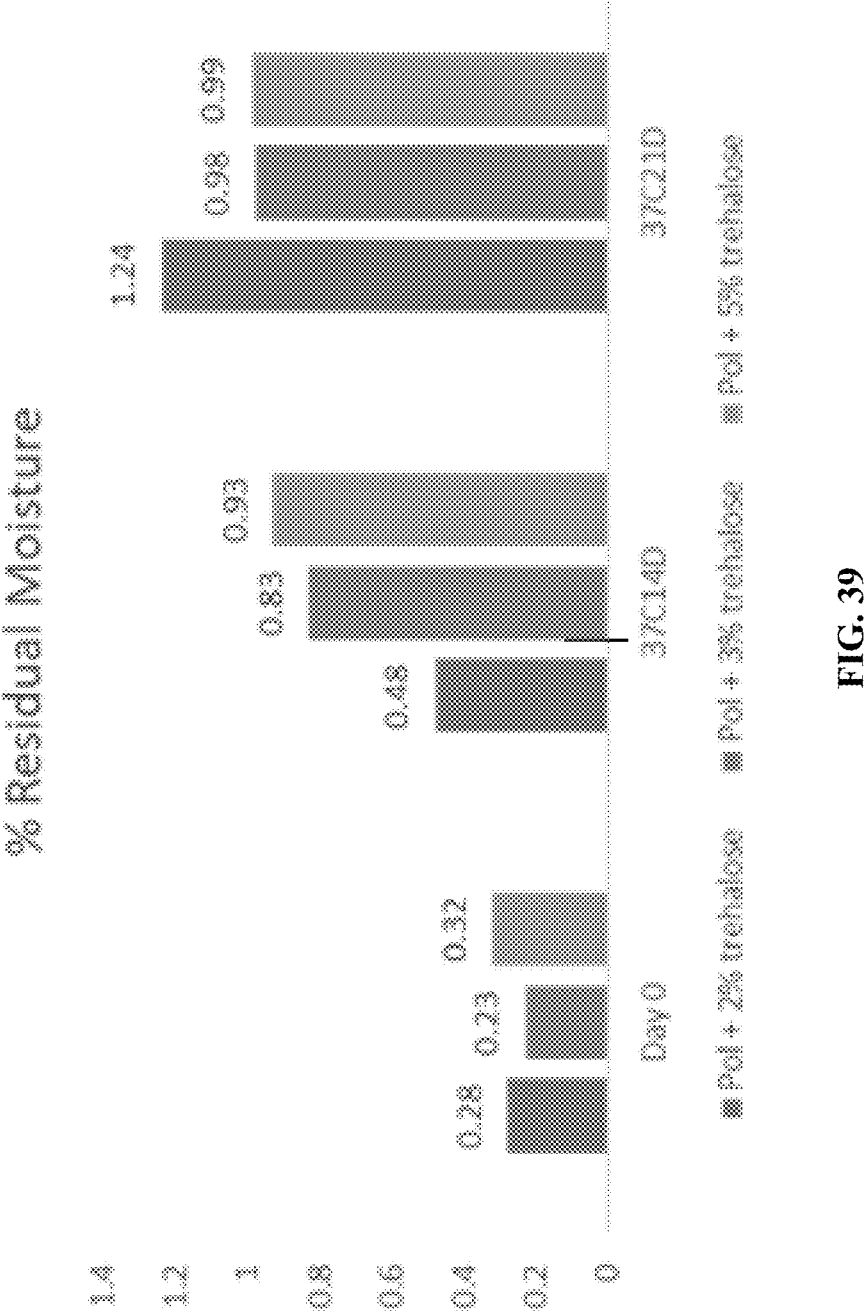
FIG. 39 shows Pol 812 lyophilised beads with 2%, 3% and 5% trehalose.

Comparing lyophilised cake and bead of ffN solution. The residual moisture of lyophilised ffN cake is higher than lyophilised ffN beads for the same lyophilisation cycle (FIG. 38).

Sequencing was also performed to compare the sequencing metrics between lyophilised ffN cakes and beads. Lyophilisation of ffN cakes and beads were performed on two lyophilisation cycles and results from both cycles showed that ffN cakes exhibited higher prephasing metrics as compared to ffN beads.

Example 13—Bead Lyophilisation of Polymerase

Polymerase lyophilisation was performed in the absence of glycerol. Excipient chosen for polymerase (e.g., Pol 812) lyophilisation was based on an earlier excipient screen of trehalose and sucrose on lyophilised Pol 812 cakes. Lyophilised Pol 812 with 30% trehalose exhibited the highest FRET activity after staging.

Lower concentration of trehalose was explored and Pol 812 was lyophilised at 7.5 mg/mL with 2%, 3% and 5% trehalose. Despite increasing residual moisture after staging at 37° C., most all sequencing metrics are still within 2 standard deviation of the liquid control.

A proof of concept study was performed where lyophilised 10×ffN beads and Pol 812 beads were prepared in Singapore and ambient shipped to the UK for NextSeq™ sequencing. It took a total of 4 days for samples to reach the UK.

NextSeg™ sequencing of ambient shipped lyophilised beads was successful and key sequencing metrics, such as phasing, prephasing and Q30 are all comparable to frozen control.

Example 14—Bead Lyophilisation of PEG-Free ExAmp

Figure 40:
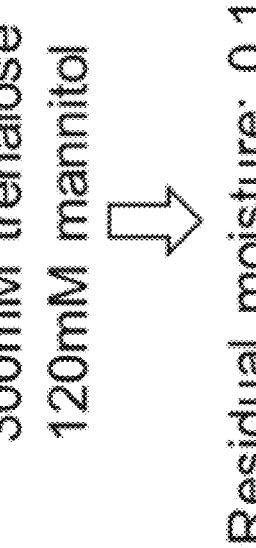
FIG. 40 shows lyophilised Ras6T beads with 200 mM Trehalose+120 mM Mannitol and 300 mM Trehalose+120 mM Mannitol.

PEG-free ExAmp, for example, Ras6T, cake lyophilisation was performed. Excipient screening was done for Ras6T and 200 mM Trehalose+120 mM Mannitol and 300 mM Trehalose+120 mM Mannitol are the top two excipients. Bead lyophilisation was performed with these excipients. Bead lyophilisation of Ras6T was successful with low residual moisture as seen in FIG. 40.

Figure 41:
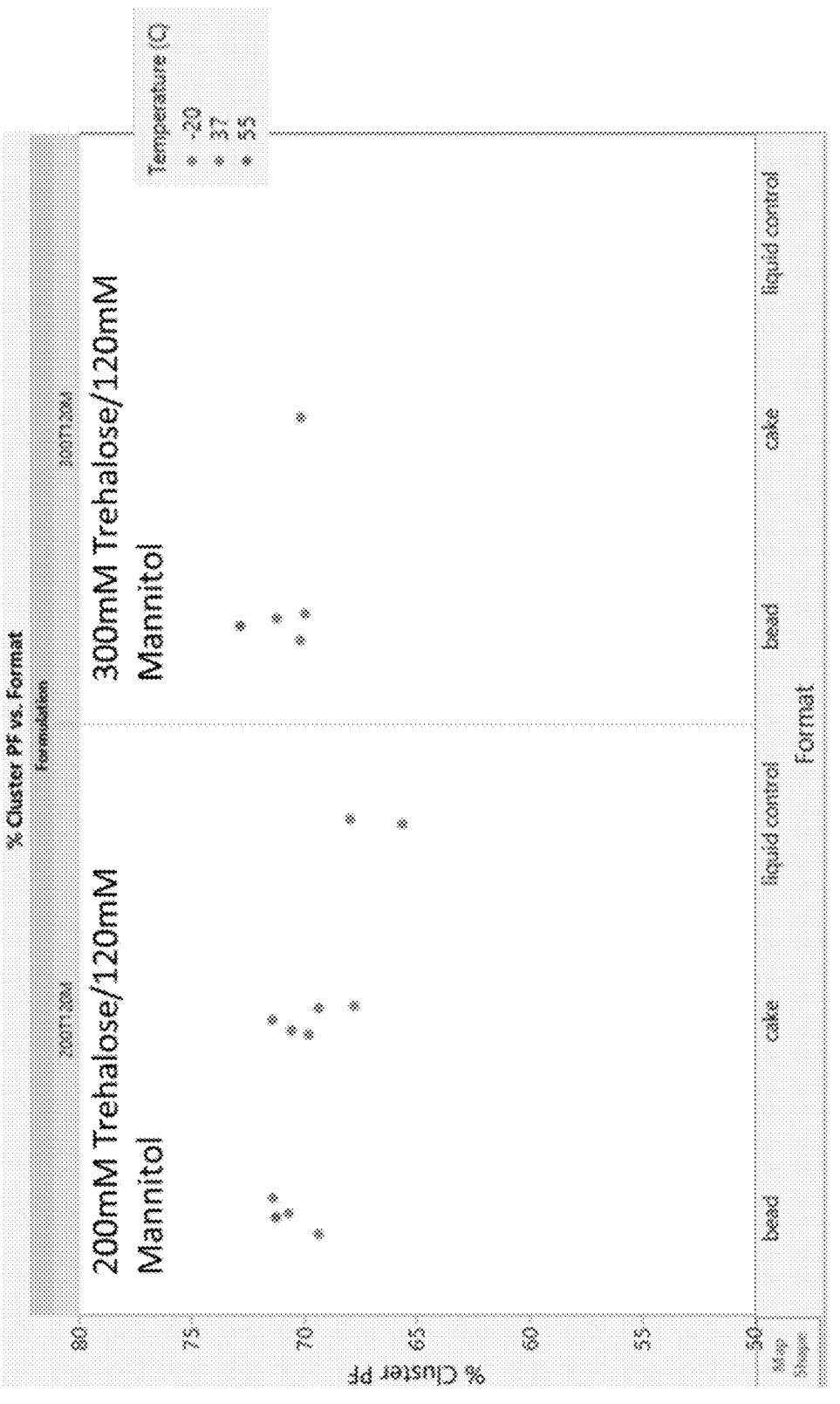
FIG. 41 shows % cluster passing filter for both lyophilised Ras6T cakes and beads with two different excipients.
Figure 42:
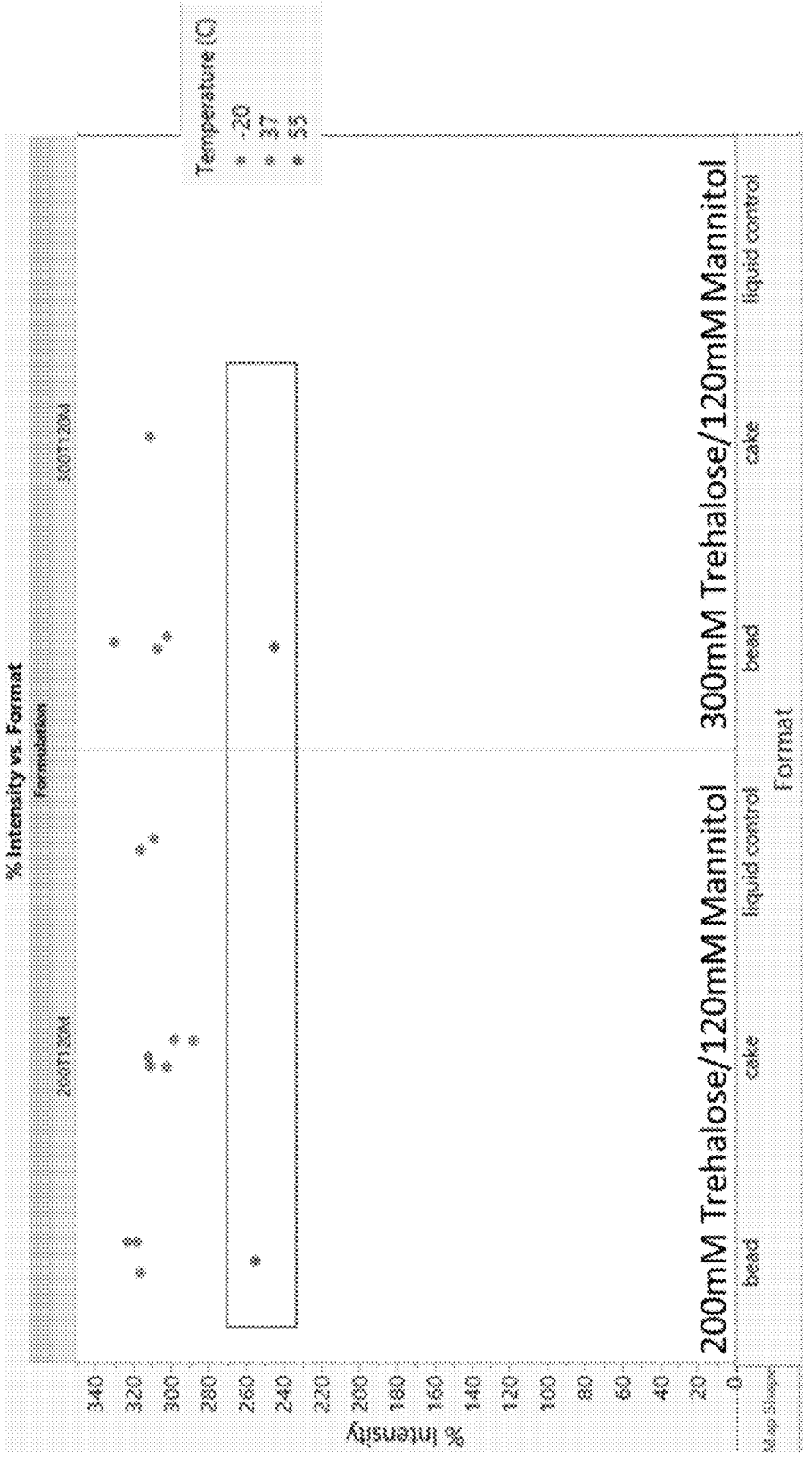
FIG. 42 shows intensity for both lyophilised Ras6T cakes and beads with two different excipients. Lower intensity is seen when samples are staged at 55° C., most likely due to dephosphorylation at higher temperatures It should be appreciated that all combinations of the foregoing concepts and additional concepts discussed in greater detail below (provided such concepts are not mutually inconsistent) are contemplated as being part of the inventive subject matter disclosed herein and may be used to achieve the benefits and advantages described herein.

Comparing lyophilised cake and bead of Ras6T. Residual moisture for lyophilised Ras6T cakes are slightly higher that lyophilised beads (Cakes: 0.3-0.6% vs Beads: 0.17-0.23%). There is no significant difference in sequencing between lyophilised cake and beads for Ras6T. Sequencing metrics comparing between lyophilised Ras6T cakes and beads are found in FIGS. 41 and 42.

In summary, there is no significant difference in between lyophilised cake and beads for Ras6T. Both cake and beads are able to withstand staging at 37° C. for 26 days.

Example 15—Bead Lyophilisation of Library Preparation Reagent

Library preparation reagents were lyophilised into beads. The following were the buffers where the library preparation reagent were lyophilised in: (1) a first reagent with SSB without glycerol; (2) a second reagent with SSB without glycerol; (3) a first reagent with BB6 tagmentation buffer; or (4) a second reagent with BB6 tagmentation buffer. Excipient screening was performed on the following excipients: (1) 3% Trehalose; (2) 10% Trehalose; (3) 1% Dextran 40; or (4) 0.375% Glycine.

Samples with 10% trehalose result in the formation of beads, while samples with the other excipients did not form any beads. Lyophilised beads of a the first reagent and the second reagent with 10% trehalose and the different buffers were shipped to determine its activity.

Residual moisture of samples with 10% trehalose ranges from 1%-2%. Although it is not within the expected range of residual moisture for lyophilised beads, it still shows comparable activity with control even after staging at 37° C. This shows that both the first and second reagents retained activity after lyophilisation and it stabilizes activity over time.

To further improve the aesthetics and mechanical rigidity of the beads, higher trehalose content is proposed when lyophilising these library preparation reagents. Both the first and second reagents were determined to be stable with the addition of trehalose up to 80%.

Example 16—Mechanical Rigidity of Lyophilised Beads

To assess the mechanical rigidity of the lyophilised beads, an in-house vibrational stress test was developed. Samples are place on a vortex mixer with speed adjusted to 900 rpm. Test sample was vortexed for 10 seconds and the degree of shedding. Alternatively, a control can be run and samples can be compared against it.

Excipient screen to determine mechanical stability of lyophilised beads. Several excipients were explored to determine the mechanical stability of lyophilised beads. The following excipients were experimented (at various concentrations):

| | |
|---|---|
| Ficoll 400 | Ficoll 400 + Trehalose |
| Ficoll 400 + Ficoll 70 | Ficoll 400 + Ficoll 70 + Trehalose |
| Dextran 40 | Dextran 40 + Trehalose |
| PEG 4K | PEG 4K + Trehalose |
| Melezitose | Melezitose + Trehalose |
| Maltodextrin 4-7 | Maltodextrin 4-7 + Trehalose |
| Maltodextrin 13-17 | Maltodextrin 13-17 + Trehalose |

Although preferred implementation have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A composition comprising:
one or more nucleotides comprising a purine or pyrimidine base and a sugar moiety having a 3'-hydroxy blocking group, and
a radical scavenger, wherein the radical scavenger comprises gallic acid (GA), hydroxyethyl gallate (HEG), protocatechuic acid (PCA), catechin, or a combination thereof, and
wherein the one or more nucleotides and the radical scavenger are lyophilised together and nucleotide stability is increased by reducing lyophilisation-induced deblocking of nucleotides.

2. The composition of claim 1, further comprising:
one or more non-reducing sugars.

3. The composition of claim 2, wherein the one or more non-reducing sugars is trehalose, sucrose, inositol, maltodextrin, or dextran, mannitol, raffinose, cyclodextrin, melezitose, sorbitol, or a combination thereof.

4. The composition of claim 2, wherein the composition comprises at least about 5 wt. % non-reducing sugar.

5. The composition of claim 2, wherein the composition comprises about 5 wt. % or less non-reducing sugar.

6. The composition of claim 1, further comprising:
a polymerase.

7. The composition of claim 1, further comprising:
a functional protein activator.

8. The composition of claim 7, wherein the functional protein activator comprises magnesium, a magnesium salt, or combination thereof.

9. The composition of claim 1, wherein the 3'-hydroxy blocking group is a reversible blocking group.

10. The composition of claim 1, wherein the one or more nucleotides is linked to a detectable label.

11. The composition of claim 10, wherein the detectable label comprises a fluorophore.

12. The composition of claim 1, wherein the one or more nucleotides is linked to a detectable label via a cleavable linker.

13. The composition of claim 1, wherein the composition is a microsphere, a cake, or a combination thereof.

14. The composition of claim 13, wherein the composition has a cross-section of between about 0.1 mm and about 25 mm.

15. The composition of claim 13, wherein, when the composition is a microsphere, the microsphere is spherical, elliptical, or toroidal.

16. The composition of claim 1, wherein the composition comprises less than about 1 wt. % glycerol.

17. The composition of claim 1, wherein the composition comprises about 5 wt. % or less of a crowding agent.

18. The composition of claim 17, wherein the crowding agent comprises polyethylene glycol (PEG), polyvinyl pyrrolidone, dextran, maltodextrin, ficoll, polyacrylamide, or a combination thereof.

19. The composition of claim 1, further comprising a moisture content below about 10 wt. %.

* * * * *